United States Patent
Maehata et al.

(10) Patent No.: US 11,161,843 B2
(45) Date of Patent: Nov. 2, 2021

(54) FUSED HETEROCYCLIC COMPOUND AND COMPOSITION CONTAINING SAME

(71) Applicant: Sumitomo Chemical Company, Limited, Tokyo (JP)

(72) Inventors: Ryota Maehata, Takarazuka (JP); Masaru Shimomura, Tokyo (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 343 days.

(21) Appl. No.: 16/480,011

(22) PCT Filed: Jan. 23, 2018

(86) PCT No.: PCT/JP2018/001914
§ 371 (c)(1),
(2) Date: Jul. 23, 2019

(87) PCT Pub. No.: WO2018/139436
PCT Pub. Date: Aug. 2, 2018

(65) Prior Publication Data
US 2019/0389858 A1 Dec. 26, 2019

(30) Foreign Application Priority Data

Jan. 24, 2017 (JP) .............................. JP2017-010118

(51) Int. Cl.
*C07D 471/04* (2006.01)
*A01N 43/90* (2006.01)

(52) U.S. Cl.
CPC ........... *C07D 471/04* (2013.01); *A01N 43/90* (2013.01)

(58) Field of Classification Search
None
See application file for complete search history.

(56) References Cited

U.S. PATENT DOCUMENTS

| 2007/0281950 A1 | 12/2007 | Qian et al. |
| 2018/0009778 A1 | 1/2018 | Tanabe et al. |
| 2018/0310559 A1 | 11/2018 | Tanabe et al. |

FOREIGN PATENT DOCUMENTS

| CN | 1631887 A | 6/2005 |
| CN | 104968663 A | 10/2015 |
| CN | 105431433 A | 3/2016 |
| EP | 2955179 A1 | 12/2015 |
| JP | 2008520595 A | 6/2008 |
| JP | 2015003906 A | 1/2015 |
| JP | 2015117194 A | 6/2015 |
| JP | 2016528189 A | 9/2016 |
| WO | 2015000715 A1 | 1/2015 |
| WO | 2016121969 A1 | 8/2016 |
| WO | 2016121970 A1 | 8/2016 |
| WO | 2016142326 A1 | 9/2016 |
| WO | 2016142327 A1 | 9/2016 |

OTHER PUBLICATIONS

English Translation of International Preliminary Report on Patentability dated Jul. 30, 2019 in International Application No. PCT/JP2018/001914.
English Translation of International Search Report dated Apr. 17, 2018 in International Application No. PCT/JP2018/001914.
Extended European Search Report dated Aug. 5, 2020 in EP Application No. 18744531.7.
Office Action dated Dec. 4, 2020 in IN Application No. 201947033221.
Office Action dated May 24, 2021 in CN Application No. 201880007902.4.

*Primary Examiner* — Alton N Pryor
(74) *Attorney, Agent, or Firm* — Panitch Schwarze Belisario & Nadel LLP

(57) ABSTRACT

Provided is a heterocyclic compound which exhibits an excellent controlling effect against harmful arthropods. In particular, provided is a heterocyclic compound represented by formula (I), wherein Q denotes a group represented by Q1 or the like, $A^2$ denotes a nitrogen atom or $CR^{4a}$, $A^3$ denotes a nitrogen atom or $CR^{4b}$, $A^4$ denotes a nitrogen atom or $CR^{4c}$, and T denotes a $C_1$-$C_{10}$ linear hydrocarbon group having one or more halogen atoms, or the like. Also provided is a composition that contains this compound and one or more components selected from the group consisting of group (a), group (b), group (c), group (d) and group (e) as listed in the description.

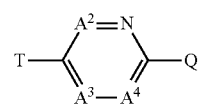

(I)

15 Claims, No Drawings

FUSED HETEROCYCLIC COMPOUND AND COMPOSITION CONTAINING SAME

CROSS-REFERENCE TO RELATED APPLICATION

This application is a Section 371 of International Application No. PCT/JP2018/001914, filed Jan. 23, 2018, which was published in the Japanese language on Aug. 2, 2018, under International Publication No. WO 2018/139436 A1, which claims priority under 35 U.S.C. 119(b) to Japanese Application No. 2017-010118 filed Jan. 24, 2017, the disclosures of which are incorporated herein by reference in their entireties.

TECHNICAL FIELD

The present invention is related to a heterocyclic compound and a composition for controlling harmful arthropods comprising the same.

BACKGROUND ART

To date, in order to control harmful arthropods, various compounds have been studied and come into practical use.

Also, a certain class of compound has been known to have an effect on controlling pests (see Patent Document 1).

CITATION LIST

Patent Document

Patent Document 1: WO 2016/121969 A1

SUMMARY OF THE INVENTION

Problems to be Solved by Invention

An object of the present invention is to provide a compound having an excellent efficacy for controlling harmful arthropods.

Means to Solve Problems

That is, the present invention is as follows.

[1] A compound represented by formula (I):

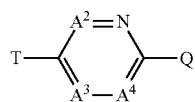

(I)

[wherein

Q represents a group represented by the following formula Q1, a group represented by the following formula Q2, a group represented by the following formula Q3, or a group represented by the following formula Q4:

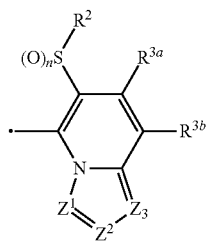 Q1

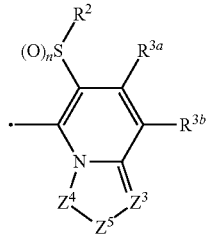 Q2

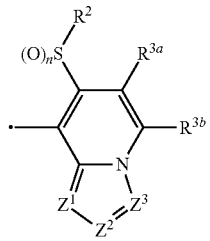 Q3

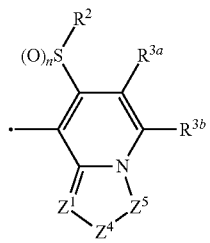 Q4

(wherein
n is 0, 1 or 2,
$R^2$ represents a cyclopropyl group, a cyclopropylmethyl group, or a C1-C6 alkyl group optionally having one or more halogen atoms,
$Z^1$ represents a nitrogen atom or $CR^{3c}$,
$Z^2$ represents a nitrogen atom or $CR^{3d}$,
$Z^3$ represents a nitrogen atom or $CR^{3e}$,
$Z^4$ represents $NR^{34}$, $CR^{36}R^{37}$ or $C(O)$,
$Z^5$ represents $NR^{35}$, $CR^{38}R^{39}$ or $C(O)$,
$R^{3a}$, $R^{3b}$, $R^{3c}$, $R^{3d}$ and $R^{3e}$ each independently represents a C1-C6 chain hydrocarbon group optionally having one or more substituents selected from Group B, a C3-C7 cycloalkyl group optionally having one or more substituents selected from Group E, a phenyl group optionally having one or more substituents selected from Group H, a five or six membered aromatic heterocyclic group optionally having one or more substituents selected from Group H, OR12, $NR^{11}R^{12}$, $NR^{11a}R^{12a}$, $NR^{29}NR^{11}R^{12}$, $NR^{29}OR^{11}$, $NR^{11}C(O)R^{13}$, $NR^{29}NR^{11}C(O)R^{13}$, $NR^{11}C(O)OR^{14}$, $NR^{29}NR^{11}C(O)OR^{14}$, $NR^{11}C(O)NR^{15}R^{16}$, $NR^{29}NR^{11}C(O)NR^{15}R^{16}$, $N=CHNR^{15}R^{16}$, $N=S(O)_xR^{15}R^{16}$, $C(O)OR^{17}$, a cyano group, a nitro group, a halogen atom, or a hydrogen atom,
x is 0 or 1,
$R^{34}$ and $R^{35}$ each independently represents a C1-C6 chain hydrocarbon group optionally having one or more substituents selected from Group B, a phenyl group optionally having one or more substituents selected from Group C, a five or six membered aromatic heterocyclic group optionally having one or more substituents selected from Group C, a C3-C7 aliphatic hydrocarbon group optionally having one or more substituents selected from Group C, C(O)OR$^d$, C(O)R$^d$, C(O)NR$^e$R$^f$, S(O)$_2$R$^i$, or a hydrogen atom, R$^{36}$, R$^{37}$, R$^{38}$ and R$^{39}$ each independently represents a C1-C6 chain hydrocarbon group optionally having one or more substituents selected from Group B, a phenyl group optionally having one or more substituents selected from Group C, a C3-C7 aliphatic hydrocarbon group optionally having one or more substituents selected from Group C, or a hydrogen atom, R$^d$ represents a C1-C6 chain hydrocarbon group optionally having one or more halogen atoms, or a hydrogen atom, R$^e$ and R$^f$ each independently represents a C1-C6 chain hydrocarbon group optionally having one or more halogen atoms, a C3-C7 aliphatic hydrocarbon group optionally having one or more halogen atoms, or a hydrogen atom, R$^i$ represents a C1-C6 chain hydrocarbon group optionally having one or more halogen atoms), A$^2$ represents a nitrogen atom or CR$^{4a}$,
A$^3$ represents a nitrogen atom or CR$^{4b}$,
A$^4$ represents a nitrogen atom or CR$^4$C, R$^{4a}$, R$^{4b}$, and R$^{4c}$ each independently represents a C1-C6 chain hydrocarbon group optionally having one or more halogen atoms, a nitro group, OR$^{18}$, NR$^{18}$R$^{19}$, a cyano group, a halogen atom or a hydrogen atom, R$^{18}$ represents a C1-C6 chain hydrocarbon group optionally having one or more halogen atoms, R$^{19}$ represents a C1-C6 chain hydrocarbon group optionally having one or more halogen atoms or a hydrogen atom, T represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, a C3-C7 cycloalkyl group having one or more substituents selected from Group G, OR$^1$, S(O)$_m$R$^1$, OS(O)$_2$R$^1$, CH$_2$OR$^1$, NR$^1$R$^{24}$, C(O)R$^1$, C(O)NR$^1$R$^{24}$, NR$^{24}$C(O)R$^1$, N=CR$^1$R$^{30}$, a group represented by the following formula T-1, a group represented by the following formula T-2, a group represented by the following formula T-3, a group represented by the following formula T-4, a group represented by the following formula T-5, a group represented by the following formula T-6, a group represented by the following formula T-7, a group represented by the following formula T-8, a group represented by the following formula T-9, a group represented by the following formula T-10, a group represented by the following formula T-11, or a group represented by the following formula T-12:

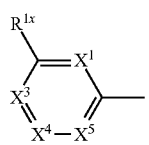

T-1

-continued

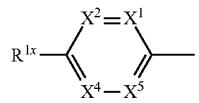

T-2

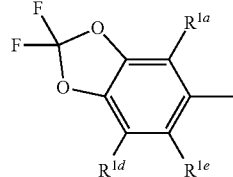

T-3

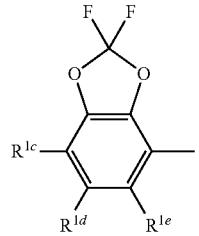

T-4

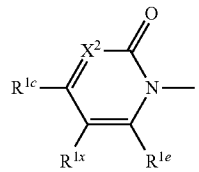

T-5

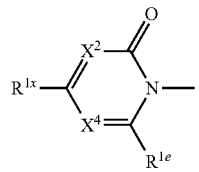

T-6

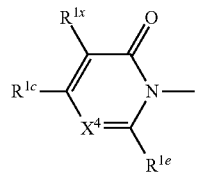

T-7

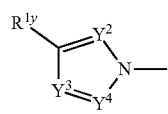

T-8

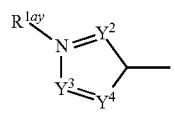

T-9

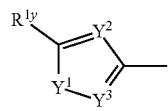

T-10

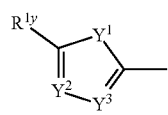

T-11

-continued

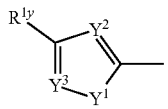
T-12

$X^1$ represents a nitrogen atom, or $CR^{1a}$,
$X^2$ represents a nitrogen atom, or $CR^{1b}$,
$X^3$ represents a nitrogen atom, or $CR^{1c}$,
$X^4$ represents a nitrogen atom, or $CR^{1d}$,
$X^5$ represents a nitrogen atom, or $CR^{1e}$,
$R^{1a}$, $R^{1b}$, $R^{1c}$, $R^{1d}$ and $R^{1e}$ each independently represents a C1-C6 chain hydrocarbon group optionally having one or more halogen atoms, a C3-C6 cycloalkyl group optionally having one or more halogen atoms, a halogen atom or a hydrogen atom, $Y^1$ represents $NR^{25}$, an oxygen atom, or a sulfur atom,
$Y^2$ represents a nitrogen atom, or $CR^{26}$,
$Y^3$ represents a nitrogen atom, or $CR^{27}$,
$Y^4$ represents a nitrogen atom, or $CR^{28}$,
$R^{25}$ represents a C1-C6 chain hydrocarbon group optionally having one or more halogen atoms, a C1-C6 alkoxy group optionally having one or more halogen atoms, a C3-C7 cycloalkyl group optionally having one or more halogen atoms, or a (C3-C7 cycloalkyl)C1-C6 alkyl group optionally having one or more halogen atoms, $R^{26}$, $R^{27}$, and $R^{28}$ each independently represents a C1-C6 chain hydrocarbon group optionally having one or more halogen atoms, a C3-C6 cycloalkyl group optionally having one or more halogen atoms, a halogen atom, or a hydrogen atom, $R^{1x}$ represents $OR^7$, $OS(O)_2R^7$, $S(O)_mR^7$, $NR^8S(O)_2R^7$, a C1-C5 chain hydrocarbon group having one or more halogen atoms, a cyano group, or a halogen atom, $R^{1y}$ represents $OR^7$, $OS(O)_2R^7$, $S(O)_mR^7$, $NR^8S(O)_2R^7$, a cyano group, a C1-C5 chain hydrocarbon group having one or more halogen atoms, or a halogen atom, $R^{1ay}$ and $R^7$ each independently represents a C1-C6 chain hydrocarbon group having one or more halogen atoms, $R^8$ represents a C1-C6 chain hydrocarbon group optionally having one or more halogen atoms, or a hydrogen atom, m is 0, 1, or 2, $R^1$ represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, or a C3-C7 cycloalkyl group having one or more substituents selected from Group G, $R^{11}$, $R^{17}$, $R^{24}$ and $R^{29}$ each independently represents a C1-C6 chain hydrocarbon group optionally having one or more halogen atoms, or a hydrogen atom, $R^{30}$ represents a C1-C6 chain hydrocarbon group optionally having one or more halogen atoms, or a hydrogen atom, $R^{12}$ represents a C1-C6 chain hydrocarbon group optionally having one or more halogen atoms, a C1-C6 alkyl group having one substituent selected from Group F, a phenyl group optionally having one or more substituents selected from Group H, a five or six membered aromatic heterocyclic group optionally having one or more substituents selected from Group H, $S(O)_2R^{23}$, or a hydrogen atom, $R^{23}$ represents a C1-C6 chain hydrocarbon group optionally having one or more halogen atoms, or a phenyl group optionally having one or more substituents selected from Group D, $R^{11a}$ and $R^{12a}$, and the nitrogen atom to which they are attached are taken together to form a three to seven membered nonaromatic heterocyclic group optionally having one or more substituents selected from Group E, $R^{13}$ represents a C1-C6 chain hydrocarbon group optionally having one or more halogen atoms, a C3-C7 cycloalkyl group optionally having one or more halogen atoms, a (C3-C6 cycloalkyl) C1-C3 alkyl group optionally having one or more halogen atoms, a phenyl group optionally having one or more substituents selected from Group D, a five or six membered aromatic heterocyclic group optionally having one or more substituents selected from Group D, or a hydrogen atom, $R^{14}$ represents a C1-C6 chain hydrocarbon group optionally having one or more halogen atoms, a C3-C7 cycloalkyl group optionally having one or more halogen atoms, a (C3-C6 cycloalkyl) C1-C3 alkyl group optionally having one or more halogen atoms, or a phenyl C1-C3 alkyl group {the phenyl moiety in the phenyl C1-C3 alkyl group may optionally have one or more substituents selected from Group D}, $R^{15}$ and $R^{16}$ each independently represents a C1-C6 alkyl group optionally having one or more halogen atoms, Group B: a group consisting of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen, atoms, a C3-C6 cycloalkyl group optionally having one or more halogen atoms, a cyano group, a hydroxy group, and a halogen atom;

Group C: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, and a halogen atom;

Group D: a group consisting of a C1-C6 chain hydrocarbon group optionally having one or more halogen atoms, a hydroxy group, a C1-C6 alkoxy group optionally having one or more halogen atoms, a C3-C6 alkenyloxy group optionally having one or more halogen atoms, a C3-C6 alkynyloxy group optionally having one or more halogen atoms, a sulfanyl group, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, an amino group, $NHR^{21}$, $NR^{21}R^{22}$, $C(O)R^{21}$, $OC(O)R^{21}$, $C(O)OR^{21}$, a cyano group, a nitro group, and a halogen atom {$R^{21}$ and $R^{22}$ each independently represents a C1-C6 alkyl group optionally having one or more halogen atoms};

Group E: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a halogen atom, an oxo group, a hydroxy group, a cyano group, and a nitro group;

Group F: a group consisting of a C1-C6 alkoxy group optionally having one or more halogen atoms, a phenyl group optionally having one or more substituents selected from Group D, a five or six membered aromatic heterocyclic group optionally having one or more substituents selected from Group D, a C3-C7 cycloalkyl group optionally having one or more halogen atoms, a three to seven membered nonaromatic heterocyclic group optionally having one or more substituents selected from Group C, an amino group, $NHR^{21}$, $NR^{21}R^{22}$, and a cyano group;

Group G: a group consisting of a C1-C6 alkyl group having one or more halogen atoms;

Group H: a group consisting of a C1-C6 alkyl group optionally having one or more halogen atoms, $OR^{10}$, $NR^9R^{10}$, $C(O)R^{10}$, $C(O)NR^9R^{10}$, $OC(O)R^9$, $OC(O)OR^9$, $NR^{10}C(O)R^9$, $NR^{10}C(O)OR^9$, $C(O)OR^{10}$, a halogen atom, a nitro group, a cyano group, an amino group, and a five or six membered aromatic heterocyclic group {$R^9$ represents a C1-C6 alkyl group optionally having one or more halogen atoms, or a C3-C6 cycloalkyl group optionally having one or more halogen atoms, and $R^{10}$ represents a C1-C6 alkyl group optionally having one or more halogen atoms, a C3-C6 cycloalkyl group optionally having one or more halogen atoms, or a hydrogen atom}] (hereinafter, a compound represented by formula (I) is referred to as "Present compound" or "Compound of the present invention").

[2] The compound described in [1] wherein $R^{4a}$, $R^{4b}$ and $R^{4c}$ each independently represents a hydrogen atom, or a halogen atom, T represents $OR^1$, $R^1$ represents a C1-C5 chain hydrocarbon group having one or more halogen atoms, $R^2$ represents a C1-C6 alkyl group, Q represents a group represented by the above formula Q1 or a group represented by the above formula Q2, $R^{3a}$ and $R^{3b}$ each independently represents a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)R^{14}$, a halogen atom or a hydrogen atom, $R^{3c}$, $R^{3d}$ and $R^{3e}$ each independently represents a C1-C6 alkyl group optionally having one or more halogen atoms, $OR^{12}$, a halogen atom or a hydrogen atom, $Z^4$ represents $CR^{36}R^{37}$ or C(O), $Z^5$ represents $NR^{35}$ or $CR^{38}R^{39}$, $R^{35}$ represents a C1-C6 alkyl group or a hydrogen atom, and $R^{36}$ and $R^{37}$ each independently represents a C1-C6 alkyl group optionally having one or more halogen atoms, or a hydrogen atom, and $R^{37}$ and $R^{38}$ each represents a hydrogen atom.

[3] The compound described in [2] wherein $R^1$ represents a C1-C5 alkyl group having three or more fluorine atoms, $R^{3a}$ and $R^{3b}$ each independently represents a C1-C6 alkyl group optionally having one or more halogen atoms, $OR^{12}$, a halogen atom, or a hydrogen atom, and $R^{4a}$, $R^{4b}$ and $R^{4c}$ each represents a hydrogen atom.

[4] The compound described in [3] wherein $R^2$ represents an ethyl group, and $R^{3c}$, $R^{3d}$, $R^{3e}$, $R^{35}$, $R^{36}$, $R^{37}$, $R^{38}$ and $R^{39}$ each represents a hydrogen atom.

[5] The compound described in any one of [1] to [4] wherein $A^2$ represents $CR^{4a}$ and $A^4$ represents $CR^{4c}$.

[6] The compound described in any one of [1] to [4] wherein $A^2$ represents $CR^{4a}$, $A^3$ represents $CR^{4b}$ and $A^4$ represents $CR^{4c}$.

[7] The compound described in [1] wherein $A^2$ represents $CR^{4a}$, $A^3$ represents $CR^{4b}$, $A^4$ represents $CR^{4c}$, $R^{4a}$, $R^{4b}$ and $R^{4c}$ each independently represents a hydrogen atom or a halogen atom, T represents $OR^1$, $R^1$ represents a C1-C5 chain hydrocarbon group having one or more halogen atoms, $R^2$ represents a C1-C6 alkyl group, Q represents a group represented by the above formula Q1, $R^{3a}$ and $R^{3b}$ each independently represents a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)OR^{14}$, a halogen atom or a hydrogen atom, and $R^{3c}$, $R^{3d}$ and $R^{3e}$ each independently represents a C1-C6 alkyl group optionally having one or more halogen atoms, $OR^{12}$, a halogen atom or a hydrogen atom.

[8] The compound described in [7] wherein $R^1$ represents a C1-C5 alkyl group having three or more fluorine atoms, $R^{3a}$ and $R^{3b}$ each independently represents a C1-C6 alkyl group optionally having one or more halogen atoms, $OR^{12}$, a halogen atom, or a hydrogen atom, and $R^{4a}$, $R^{4b}$ and $R^{4c}$ each represents a hydrogen atom.

[9] The compound described in [7] or [8] wherein $R^{3c}$, $R^{3d}$ and $R^{3e}$ each represents a hydrogen atom.

[9-2] The compound described in [7] or [8] wherein $R^2$ represents an ethyl group, $Z^1$ represents $CR^{3c}$, $Z^2$ represents a nitrogen atom or $CR^{3d}$, $Z^3$ represents a nitrogen atom, and $R^{3c}$ and $R^{3d}$ each represents a hydrogen atom.

[10] The compound described in [1] wherein $A^2$ represents $CR^{4a}$, $A^3$ represents $CR^{4b}$, $A^4$ represents $CR^{4c}$, $R^{4a}$, $R^{4b}$ and $R^{4c}$ each independently represents a hydrogen atom or a halogen atom, T represents $OR^1$, $R^1$ represents a C1-C5 chain hydrocarbon group having one or more halogen atoms, $R^2$ represents a C1-C6 alkyl group, Q represents a group represented by the above formula $Q^2$, $R^{3a}$ and $R^{3b}$ each independently represents a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H), $OR^{12}$, $NR^{11}R^{12}$, $NR^{11}C(O) OR^{14}$, a halogen atom or a hydrogen atom, $Z^4$ represents $CR^{36}R^{37}$ or C(O), $Z^5$ represents $NR^{35}$ or $CR^{38}R^{39}$, $R^{3e}$ represents a C1-C6 alkyl group optionally having one or more halogen atoms, $OR^{12}$, a halogen atom or a hydrogen atom, $R^{35}$ represents a C1-C6 alkyl group or a hydrogen atom, $R^{36}$ and $R^{38}$ each independently represents a C1-C6 alkyl group optionally having one or more halogen atoms, or a hydrogen atom, and $R^{37}$ and $R^{38}$ each represents a hydrogen atom.

[11] The compound described in [10] wherein $R^1$ represents a C1-C5 alkyl group having three or more fluorine atoms, $R^{3a}$ and $R^{3b}$ each independently represents a C1-C6 alkyl group optionally having one or more halogen atoms, $OR^{12}$, a halogen atom, or a hydrogen atom, and $R^{4a}$, $R^{4b}$ and $R^{4c}$ each represents a hydrogen atom.

[12] The compound described in [10] or [11] wherein $R^2$ represents an ethyl group, and $R^{35}$, $R^{36}$, $R^{37}$, $R^{38}$, and $R^{39}$ each represents a hydrogen atom.

[12-2] The compound described in [10] or [13] wherein $R^2$ represents an ethyl group, $Z^3$ represents a nitrogen atom, $Z^4$ represents $CR^{36}R^{37}$ or C(O), $Z^5$ represents $CR^{33}R^{39}$, and $R^{36}$, $R^{37}$, $R^{3e}$ and $R^{33}$ each represents a hydrogen atom.

[13] A composition for controlling a harmful arthropod comprising the compound described in any one of [1] to [12], [9-2] or [12-2] and an inert carrier.

[14] A method for controlling a harmful arthropod which comprises applying an effective amount of the compound according to any one of [1] to [12], [9-2] or [12-2] to a harmful arthropod or a habitat where a harmful arthropod lives.

[15] A composition comprising one or more ingredients selected from the group consisting of the following Group (a), Group (b), Group (c), Group (d) and Group (e), and the compound according to any one of [1] to [12], [9-2] or [12-2], Group (a): a group consisting of insecticidal ingredients, miticidal ingredients, and nematicidal ingredients;
Group (b): fungicidal ingredients;
Group (c): plant growth modulating ingredients;
Group (d): phytotoxicity-reducing ingredients; and
Group (e): synergist ingredients
(hereinafter, which is referred to as "Present composition" or "Composition of the present invention").

Effect of Invention

The present invention can control harmful arthropods.

MODE FOR CARRYING OUT THE INVENTION

The substituent(s) as described herein is/are explained.

The term "halogen atom" represents fluorine atom, chlorine atom, bromine atom, or iodine atom.

When the substituent has two or more halogen atoms, these halogen atoms may be identical to or different from each other.

The expression of "CX-CY" as used herein represents that the number of carbon atom is from X to Y. For example, the expression of "C1-C6" represents that the number of carbon atom is from 1 to 6.

The term of "chain hydrocarbon group" represents an alkyl group, an alkenyl group, or an alkynyl group.

Examples of the term of "alkyl group" include methyl group, ethyl group, propyl group, isopropyl group, 1,1-dimethylpropyl group, 1,2-dimethylpropyl group, 1-ethyl-propyl group, butyl group, sec-butyl group, tert-butyl group, pentyl group, hexyl group, heptyl group, octyl group, nonyl group, and decyl group.

Examples of the term of "alkenyl group" include vinyl group, 1-propenyl group, 2-propenyl group, 1-methyl-1-propenyl group, 1-methyl-2-propenyl group, 1,2-dimethyl-1-propenyl group, 1-ethyl-2-propenyl group, 3-butenyl group, 4-pentenyl group, 5-hexenyl group, 6-heptenyl group, 7-octenyl group, 8-nonenyl group, and 9-decenyl group.

Examples of the term of "alkynyl group" includes ethynyl group, 1-propynyl group, 2-propynyl group, 1-methyl-2-propynyl group, 1, 1-dimethyl-2-propynyl group, 1-ethyl-2-propynyl group, 2-butynyl group, 4-pentynyl group, 5-hexynyl group, 6-heptinyl group, 7-octinyl group, 8-noninyl group, and 9-decinyl group.

Examples of the term of "C1-C6 alkyl group having one or more halogen atoms" include trifluoromethyl group, 2,2,2-trifluoroethyl group, 2-bromo-1,1,2,2-tetrafluoroethyl group, 2,2,3,3-tetrafluoropropyl group, 1-methyl-2,2,3,3-tetrafluoropropyl group, and perfluorohexyl group.

Examples of the term of "C1-C5 alkyl group having three or more fluorine atoms" include trifluoromethyl group, 2,2,2-trifluoroethyl group, 2,2,3,3,3-pentafluoropropyl group, 2,2,3,3,4,4,4-heptafluoropropyl group, and perfluoropropyl group.

Examples of the term of "C3-C7 aliphatic hydrocarbon group" include cyclopropyl, cyclobutyl, cyclopentyl, cyclohexyl, and cycloheptyl.

Examples of the term of "cycloalkyl group" include cyclopropyl group, cyclobutyl group, cyclopentyl group, cyclohexyl group, and cycloheptyl group.

Examples of the term of "C3-C7 cycloalkyl group optionally having one or more halogen atoms" includes 2,2-difluorocyclopropyl group, 1-(2,2,2-trifluoroethyl)cylopropyl group, and 4-(trifluoromethyl)cyclohexyl group.

Examples of the term of "alkoxy group" include methoxy group, ethoxy group, propoxy group, butoxy group, pentoxy group, and hexyloxy group.

The term of "C1-C6 alkoxy group optionally having one or more halogen atoms" represents a C1-C6 alkoxy group wherein one or more hydrogen atoms are substituted with a halogen atom, and includes, for example, trifluoromethoxy group, difluoromethoxy group, 2,2,2-trichloroethoxy group, and 2,2,2-trifluoroethoxy group.

The term of "alkylsulfanyl group", "alkylsulfinyl group", and "alkylsulfonyl group" represent an alkyl group including an $S(O)_z$ moiety, respectively.

For example, examples of the "alkylsulfanyl group" when z is 0 include methylsulfanyl group, ethylsulfanyl group, propylsulfanyl group, and isopropylsulfanyl group.

For example, examples of the "alkylsulfinyl group" when z is 1 include methylsulfinyl group, ethylsulfinyl group, propylsulfinyl group, and isopropylsulfinyl group.

For example, examples of the "alkylsulfonyl group" when z is 2 include methylsulfonyl group, ethylsulfonyl group, propylsulfonyl group, and isopropylsulfonyl group.

Examples of the term of "three (3) to seven (7) membered nonaromatic heterocyclic group" include aziridine ring, azetidine ring, pyrrolidine ring, imidazoline ring, imidazolidine ring, piperidine ring, tetrahydropyrimidine ring, hexahydropyrimidine ring, piperazine ring, azepane ring, oxazolidine ring, isoxazolidine ring, 1,3-oxazinane ring, morpholine ring, 1,4-oxazepane ring, thiazolidine ring, isothiazolidine ring, 1,3-thiazinane ring, thiomorpholine ring, and 1,4-thiazepane ring. Examples of the three to seven membered nonaromatic heterocyclic group optionally having one or more substituents selected from Group E include the followings:

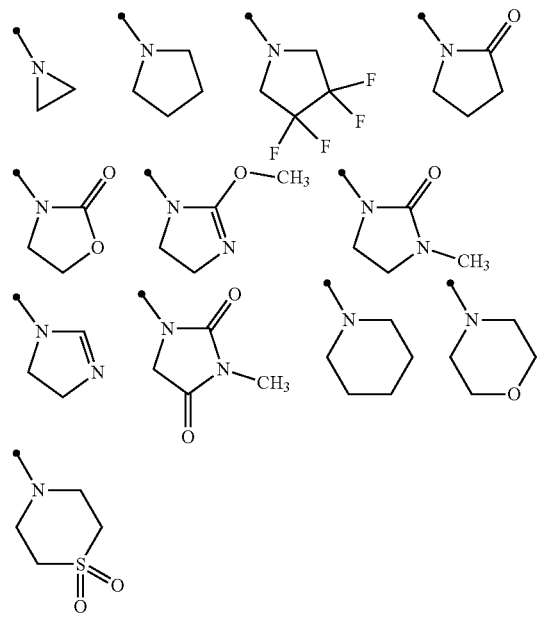

The term of "(C1-C5 alkoxy)C2-C5 alkyl group having one or more halogen atoms" represents a group wherein the (C1-C5 alkoxy) and/or the (C2-C5 alkyl) has/have one or more halogen atoms, and includes, for example, 2-(trifluoromethoxy)ethyl group, 2,2-difluoro-3-methoxypropyl group, 2,2-difluoro-3-(2,2,2-trifluoroethoxy)propyl group, and 3-(2-chloroethoxy)propyl group.

The term of "(C1-C5 alkylsulfanyl)C2-C5 alkyl group having one or more halogen atoms" represents a group wherein the (C1-C5 alkylsulfanyl) and/or the (C2-C5 alkyl) has/have one or more halogen atoms, and includes, for example, 2,2-difluoro-2-(trifluoromethylthio)ethyl group.

The term of "(C1-C5 alkylsulfinyl)C2-C5 alkyl group having one or more halogen atoms" represents a group wherein the (C1-C5 alkylsulfinyl) and/or the (C2-C5 alkyl) has/have one or more halogen atoms, and includes, for example, 2,2-difluoro-2-(trifluoromethansulfinyl)ethyl group.

The term of "(C1-C5 alkylsulfonyl)C2-C5 alkyl group having one or more halogen atoms" represents a group wherein the (C1-C5 alkylsulfonyl) and/or the (C2-C5 alkyl) has/have one or more halogen atoms, and includes, for example, 2,2-difluoro-2-(trifluoromethansulfonyl)ethyl group.

The term of "(C3-C7 cycloalkyl)C1-C3 alkyl group optionally having one or more halogen atoms" represents a group wherein the (C3-C7 cycloalkyl) and/or the (C1-C3 alkyl) has/have one or more halogen atoms, and includes, for example, (2,2-difluorocyclopropyl)methyl group, 2-cyclopropyl-1,1,2,2-tetrafluoroethyl group, and 2-(2,2-difluorocyclopropyl)-1,1,2,2-tetrafluoroethyl group.

Examples of the term of "phenyl C1-C3 alkyl group {the phenyl moiety in the phenyl C1-C3 alkyl group may optionally have one or more substituents selected from Group D}" include benzyl group, 2-fluorobenzyl group, 4-chlorobenzyl group, 4-(trifluoromethyl)benzyl group, and 2-[4-(trifluoromethyl)phenyl]ethyl group.

The term of "five(5) or six(6) membered aromatic heterocyclic group" represents a five membered aromatic heterocyclic group or a six membered aromatic heterocyclic group, and examples of the five membered aromatic heterocyclic group include pyrrolyl group, furyl group, thienyl group, pyrazolyl group, imidazolyl group, triazolyl group, tetrazolyl group, oxazolyl group, isoxazolyl group, thiazolyl group, isothiazolyl group, oxadiazolyl group, and thiadiazolyl group. As the five membered aromatic heterocyclic group, pyrrolyl group, pyrazolyl group, imidazolyl group, 1,2,4-triazolyl group, 1,2,3-triazolyl group, or tetrazolyl group is preferably included. Examples of the six membered aromatic heterocyclic group include pyridyl group, pyridazinyl group, pyrimidinyl group, and pyrazinyl group.

The term of "five(5) or six(6) membered aromatic heterocyclic group" represents a five membered aromatic heterocyclic group or a six membered aromatic heterocyclic group, Examples of the embodiment of the compound of the present invention include the following compounds.

Embodiment 1

A compound of the present invention wherein $R^{3b}$ represents a phenyl group optionally having one or more substituents selected from Group H, any one six membered aromatic heterocyclic group selected from Group V (the six membered aromatic heterocyclic group may optionally have one or more substituents selected from Group H), or any one five membered aromatic heterocyclic group selected from Group W (the five membered aromatic heterocyclic group may optionally have one or more substituents selected from Group H}:

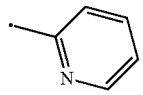
V-1

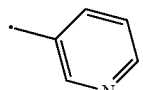
V-2

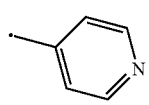
V-3

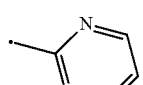
V-4

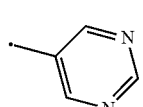
V-5

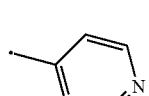
V-6

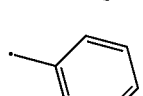
V-7

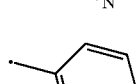
V-8

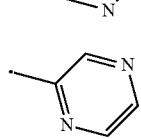
V-9

Group W:

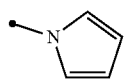
W-1

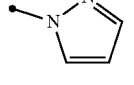
W-2

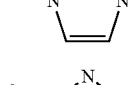
W-3

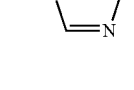
W-4

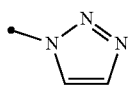 W-5

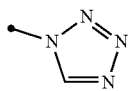 W-6

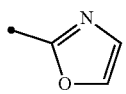 W-7

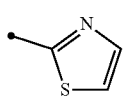 W-8

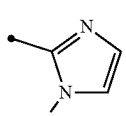 W-9

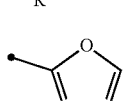 W-10

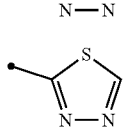 W-11

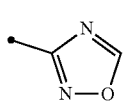 W-12

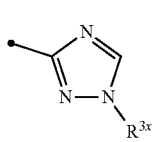 W-13

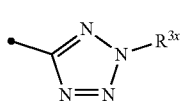 W-14

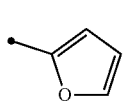 W-15

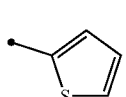 W-16

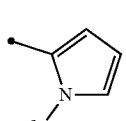 W-17

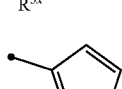 W-18

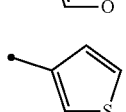 W-19

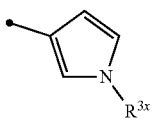 W-20

{in the formulae, $R^{3x}$ represents a C1-C6 alkyl group optionally having one or more halogen atoms};

Embodiment 2

The compound of the present invention wherein $R^2$ represents a C1-C6 alkyl group, $R^{3a}$ and $R^{3b}$ each independently represents a C1-C6 alkyl group optionally having one or more halogen atoms, a phenyl group, a pyridyl group, a pyrimidinyl group, a pyrazolyl group, a triazolyl group {the phenyl group, the pyridyl group, the pyrimidinyl group, the pyrazolyl group, and the triazolyl group each independently may optionally have one or more substituents selected from Group H}, $OR^{12}$, $NR^{11}R^{12}$, $NR^{11}C(O)$ $OR^{14}$, or a halogen atom, or a hydrogen atom, Q represents a group represented by formula Q1, or a group represented by formula Q2, $R^{3c}$, $R^{3d}$ and $R^{3e}$ each independently represents a C1-C6 alkyl group optionally having one or more halogen atoms, $OR^{12}$, a halogen atom or a hydrogen atom, $Z^4$ represents $CR^{36}R^{37}$ or C(O), $Z^5$ represents NR35 OR $CR^{38}R^{39}$, and $R^{4d}$, $R^{4b}$ and $R^{4c}$ each independently represents a hydrogen atom or a halogen atom.

Embodiment 3

The compound described in Embodiment 2 wherein $R^{3d}$ and $R^{3b}$ each independently represents a C1-C6 alkyl group optionally having one or more halogen atoms, $OR^{12}$, a halogen atom, or a hydrogen atom, $R^{35}$ represents a C1-C6 alkyl group or a hydrogen atom, $R^{36}$ and $R^{38}$ each independently represents a C1-C6 alkyl group optionally having one or more halogen atoms or a hydrogen atom, and $R^{37}$ and $R^{39}$ each represents a hydrogen atom.

Embodiment 4

The compound described in Embodiment 3 wherein $R^{4a}$, $R^{4b}$ and $R^{4c}$ each represents a hydrogen atom.

Embodiment 5

The compound described in Embodiment 3 wherein $R^{3c}$, $R^{3d}$, $R^{3e}$, $R^{4a}$, $R^{4b}$ and $R^{4c}$ each represents a hydrogen atom.

Embodiment 6

The compound described in Embodiment 3 wherein $R^{36}$, $R^{4d}$, $R^{4b}$, and $R^{4c}$ each represents a hydrogen atom.

Embodiment 7

The compound described in Embodiment 3 wherein $R^{35}$, $R^{33}$, $R^{4a}$, $R^{4b}$, and $R^{4c}$ each represents a hydrogen atom.

Embodiment 8

The compound described in Embodiment 3 wherein $R^{3a}$, $R^{3d}$, $R^{3e}$, $R^{35}$, $R^{36}$, $R^{38}$, $R^{4a}$, $R^{4b}$ and $R^{4c}$ each represents a hydrogen atom.

Embodiment 9

The compound described in Embodiment 8 wherein $R^2$ represents an ethyl group, and n is 2.

Embodiment 10

The compound described in Embodiment 2 wherein Q represents a group represented by formula Q1.

Embodiment 11

The compound described in Embodiment 10 wherein $R^{3d}$ and $R^{3b}$ each independently represents a C1-C6 alkyl group optionally having one or more halogen atoms, $OR^{12}$, a halogen atom, or a hydrogen atom.

Embodiment 12

The compound described in Embodiment 11 wherein $R^{4d}$, $R^{4b}$ and $R^{4c}$ each represents a hydrogen atom.

Embodiment 13

The compound described in Embodiment 13 wherein $R^{3c}$, $R^{3d}$, $R^{3e}$, $R^{4a}$, $R^{4b}$ and $R^{4c}$ each represents a hydrogen atom.

Embodiment 14

The compound described in Embodiment 13 wherein $R^2$ represents an ethyl group, and n is 2.

Embodiment 15

The compound described in Embodiment 2 wherein Q represents a group represented by formula Q2.

Embodiment 16

The compound described in Embodiment 15 wherein $R^{3a}$ and $R^{3b}$ each independently represents a C1-C6 alkyl group optionally having one or more halogen atoms, $OR^{12}$, a halogen atom or a hydrogen atom, $R^{35}$ represents a C1-C6 alkyl group or a hydrogen atom, $R^{36}$ and $R^{38}$ each independently represents a C1-C6 alkyl group optionally having one or more halogen atoms or a hydrogen atom, and $R^{37}$ and $R^{39}$ each represents a hydrogen atom.

Embodiment 17

The compound described in Embodiment 16 wherein $R^{4a}$, $R^{4b}$ and $R^{4c}$ each represents a hydrogen atom.

Embodiment 18

The compound described in Embodiment 16 wherein $R^{3e}$, $R^{4a}$, $R^{4b}$ and $R^{4c}$ each represents a hydrogen atom.

Embodiment 19

The compound described in Embodiment 16 wherein $R^{36}$, $R^{4d}$, $R^{4b}$, and $R^{4c}$ each represents a hydrogen atom.

Embodiment 20

The compound described in Embodiment 16 wherein $R^{3}$% $R^{38}$, $R^{4d}$, $R^{4b}$, and $R^{4c}$ each represents a hydrogen atom.

Embodiment 21

The compound described in Embodiment 16 wherein $R^{35}$, $R^{36}$, $R^{38}$, $R^{3e}$, $R^{4a}$, $R^{4b}$ and $R^{4c}$ each represents a hydrogen atom.

Embodiment 22

The compound described in Embodiment 16 wherein $R^2$ represents an ethyl group, and n is 2.

Embodiment 23

The compound described in Embodiment 2 wherein $A^2$ represents $CR^{4d}$, and $A^4$ represents $CR^{4c}$.

Embodiment 24

The compound described in Embodiment 23 wherein $R^{3d}$ and $R^{3b}$ each independently represents a C1-C6 alkyl group optionally having one or more halogen atoms, $OR^{12}$, a halogen atom, or a hydrogen atom, $R^{35}$ represents a C1-C6 alkyl group or a hydrogen atom, $R^{38}$ and $R^{33}$ each independently represents a C1-C6 alkyl group optionally having one or more halogen atoms or a hydrogen atom, and $R^{37}$ and $R^{39}$ each represents a hydrogen atom.

Embodiment 25

The compound described in Embodiment 24 wherein $R^{4d}$, $R^{4b}$ and $R^{4c}$ each represents a hydrogen atom.

Embodiment 26

The compound described in Embodiment 24 wherein $R^{3c}$, $R^{3d}$, $R^{3e}$, $R^{4a}$, $R^{4b}$ and $R^{4c}$ each represents a hydrogen atom.

Embodiment 27

The compound described in Embodiment 24 wherein $R^{36}$, $R^{4a}$, $R^{4b}$, and $R^{4c}$ each represents a hydrogen atom.

Embodiment 28

The compound described in Embodiment 24 wherein $R^{35}$, $R^{38}$, $R^{4a}$, $R^{4b}$, and $R^{4c}$ each represents a hydrogen atom.

Embodiment 29

The compound described in Embodiment 24 wherein $R^{3c}$, $R^{3d}$, $R^{3e}$, $R^{35}$, $R^{36}$, $R^{38}$, $R^{4a}$, $R^{4b}$ and $R^{4c}$ each represents a hydrogen atom.

Embodiment 30

The compound described in Embodiment 29 wherein $R^2$ represents an ethyl group, and n is 2.

Embodiment 31

The compound described in Embodiment 23 wherein Q represents a group represented by formula Q1.

Embodiment 32

The compound described in Embodiment 31 wherein $R^{3a}$ and $R^{3b}$ each independently represents a C1-C6 alkyl group optionally having one or more halogen atoms, $OR^{12}$, a halogen atom, or a hydrogen atom, $R^{35}$ represents a C1-C6 alkyl group or a hydrogen atom, $R^{36}$ and $R^{33}$ each independently represents a C1-C6 alkyl group optionally having one or more halogen atoms or a hydrogen atom, and $R^{37}$ and $R^{39}$ each represents a hydrogen atom.

Embodiment 33

The compound described in Embodiment 32 wherein $R^{4a}$, $R^{4b}$ and $R^{4c}$ each represents a hydrogen atom.

Embodiment 34

The compound described in Embodiment 32 wherein $R^{3c}$, $R^{3d}$, $R^{3e}$, $R^{4a}$, $R^{4b}$ and $R^{4c}$ each represents a hydrogen atom.

Embodiment 35

The compound described in Embodiment 34 wherein $R^2$ represents an ethyl group, and n is 2.

Embodiment 36

The compound described in Embodiment 23 wherein Q represents a group represented by formula $Q^2$.

Embodiment 37

The compound described in Embodiment 36 wherein $R^{3d}$ and $R^{3b}$ each independently represents a C1-C6 alkyl group optionally having one or more halogen atoms, $OR^{12}$, a halogen atom, or a hydrogen atom, $R^{35}$ represents a C1-C6 alkyl group or a hydrogen atom, $R^{36}$ and $R^{33}$ each independently represents a C1-C6 alkyl group optionally having one or more halogen atoms or a hydrogen atom, and $R^{37}$ and $R^{39}$ each represents a hydrogen atom.

Embodiment 38

The compound described in Embodiment 37 wherein $R^{4d}$, $R^{4b}$ and $R^{4c}$ each represents a hydrogen atom.

Embodiment 39

The compound described in Embodiment 37 wherein $R^{3e}$, $R^{4d}$, $R^{4b}$, and $R^{4c}$ each represents a hydrogen atom.

Embodiment 40

The compound described in Embodiment 37 wherein $R^{36}$, $R^{4d}$, $R^{4b}$, and $R^{4c}$ each represents a hydrogen atom.

Embodiment 41

The compound described in Embodiment 37 wherein $R^{3'}$, $R^{38}$, $R^{4a}$, $R^{4b}$, and $R^{4c}$ each represents a hydrogen atom.

Embodiment 42

The compound described in Embodiment 37 wherein $R^{35}$, $R^{36}$, $R^{38}$, $R^{3e}$, $R^{4a}$, $R^{4b}$, and $R^{4c}$ each represents a hydrogen atom.

Embodiment 43

The compound described in Embodiment 42 wherein $R^2$ represents an ethyl group, and n is 2.

Embodiment 44

The compound described in Embodiment 2 wherein $A^2$ represents $CR^{4a}$, $A^3$ represents $CR^{4b}$, and $A^4$ represents $CR^{4c}$.

Embodiment 44

The compound described in Embodiment 44 wherein $R^{3a}$ and $R^{3b}$ each independently represents a C1-C6 alkyl group optionally having one or more halogen atoms, $OR^{12}$, a halogen atom, or a hydrogen atom, $R^{35}$ represents a C1-C6 alkyl group or a hydrogen atom, $R^{36}$ and $R^{33}$ each independently represents a C1-C6 alkyl group optionally having one or more halogen atoms, or a hydrogen atom, and $R^{37}$ and $R^{39}$ each represents a hydrogen atom.

Embodiment 46

The compound described in Embodiment 45 wherein $R^{4a}$, $R^{4b}$, and $R^{4c}$ each represents a hydrogen atom.

Embodiment 47

The compound described in Embodiment 45 wherein $R^{3c}$, $R^{3d}$, $R^{3e}$, $R^{4a}$, $R^{4b}$, and $R^{4c}$ each represents a hydrogen atom.

Embodiment 48

The compound described in Embodiment 45 wherein $R^{36}$, $R^{4d}$, $R^{4b}$, and $R^{4c}$ each represents a hydrogen atom.

Embodiment 49

The compound described in Embodiment 45 wherein $R^{3\%}$ $R^{38}$, $R^{4d}$, $R^{4b}$, and $R^{4c}$ each represents a hydrogen atom.

Embodiment 50

The compound described in Embodiment 45 wherein $R^{3c}$, $R^{3d}$, $R^{3e}$, $R^{35}$, $R^{36}$, $R^{38}$, $R^{4d}$, $R^{4b}$ and $R^{4c}$ each represents a hydrogen atom.

Embodiment 51

The compound described in Embodiment 45 wherein $R^2$ represents an ethyl group, and n is 2.

Embodiment 52

The compound described in Embodiment 44 wherein Q represents a group represented by formula Q1.

Embodiment 53

The compound described in Embodiment 52 wherein $R^{3d}$ and $R^{3b}$ each independently represents a C1-C6 alkyl group optionally having one or more halogen atoms, $OR^{12}$, a halogen atom, or a hydrogen atom, $R^{35}$ represents a C1-C6 alkyl group or a hydrogen atom, $R^{36}$ and $R^{33}$ each independently represents a C1-C6 alkyl group optionally having one or more halogen atoms or a hydrogen atom, and $R^{37}$ and $R^{39}$ each represents a hydrogen atom.

Embodiment 54

The compound described in Embodiment 53 wherein $R^{4d}$, $R^{4b}$ and $R^{4c}$ each represents a hydrogen atom.

Embodiment 55

The compound described in Embodiment 53 wherein $R^{3c}$, $R^{3d}$, $R^{3e}$, $R^{4d}$, $R^{4b}$ and $R^{4c}$ each represents a hydrogen atom.

Embodiment 56

The compound described in Embodiment 55 wherein R2 represents an ethyl group, and n is 2.

Embodiment 57

The compound described in Embodiment 44 wherein Q represents a group represented by formula Q2.

Embodiment 58

The compound described in Embodiment 57 wherein $R^{3a}$ and $R^{3b}$ each independently represents a C1-C6 alkyl group optionally having one or more halogen atoms, $OR^{12}$, a halogen atom, or a hydrogen atom, $R^{35}$ represents a C1-C6 alkyl group or a hydrogen atom, $R^{36}$ and $R^{33}$ each independently represents a C1-C6 alkyl group optionally having one or more halogen atoms or a hydrogen atom, and $R^{37}$ and $R^{39}$ each represents a hydrogen atom.

Embodiment 59

The compound described in Embodiment 58 wherein $R^{4a}$, $R^{4b}$, and $R^{4c}$ each represents a hydrogen atom.

Embodiment 60

The compound described in Embodiment 58 wherein $R^{3e}$, $R^{4d}$, $R^{4b}$, and $R^{4c}$ each represents a hydrogen atom.

Embodiment 61

The compound described in Embodiment 58 wherein $R^{36}$, $R^{4d}$, $R^{4b}$, and $R^{4c}$ each represents a hydrogen atom.

Embodiment 62

The compound described in Embodiment 58 wherein $R^{35}$, $R^{33}$, $R^{4a}$, $R^{4b}$, and $R^{4c}$ each represents a hydrogen atom.

Embodiment 63

The compound described in Embodiment 58 wherein $R^{35}$, $R^{36}$, $R^{38}$, $R^{3e}$, $R^{4d}$, $R^{4b}$, and $R^{4c}$ each represents a hydrogen atom.

Embodiment 64

The compound described in Embodiment 63 wherein $R^2$ represents an ethyl group, and n is 2.

Embodiment 65

The compound described in any one of Embodiments 1 to 64 wherein T represents a C1-C10 chain hydrocarbon group optionally having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, a C3-C7 cycloalkyl group having one or more substituents selected from Group G, $OR^1$, $S(O)_mR^1$, $OS(O)_2R^1$, or $NR^1R^{24}$.

Embodiment 66

The compound described in any one of Embodiments 1 to 64 wherein T represents a C1-C10 chain hydrocarbon group optionally having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, a C3-C7 cycloalkyl group having one or more substituents selected from Group G, $OR^1$, $S(O)_mR^1$, $OS(O)_2R^1$, or $NR^2R^{24}$, and $R^1$ represents a C1-C5 chain hydrocarbon group having one or more halogen atoms.

Embodiment 67

The compound described in any one of Embodiments 1 to 64 wherein T represents a C1-C10 chain hydrocarbon group optionally having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, a C3-C7 cycloalkyl group having one or more substituents selected from Group G, $OR^2$, $S(O)_mR^1$, $OS(O)_2R^1$, or $NR^2R^{24}$, and R1 represents a C1-C5 alkyl group having three or more fluorine atoms.

Embodiment 68

The compound described in any one of Embodiments 1 to 64 wherein T represents $OR^1$.

Embodiment 69

The compound described in any one of Embodiments 1 to 64 wherein T represents $OR^1$, and $R^1$ represents a C1-C5 chain hydrocarbon group having one or more halogen atoms.

Embodiment 70

The compound described in any one of Embodiments 1 to 64 wherein T represents $OR^1$, and $R^1$ represents a C1-C5 alkyl group having three or more fluorine atoms.

Next, a process for preparing the compound of the present invention is explained.

Process 1

A compound of the present invention can be prepared by reacting a compound represented by formula (M-1) (hereinafter, referred to as Compound (M-1)) with a compound represented by formula (M-2) (hereinafter, referred to as Compound (M-2)) in the presence of a metal catalyst.

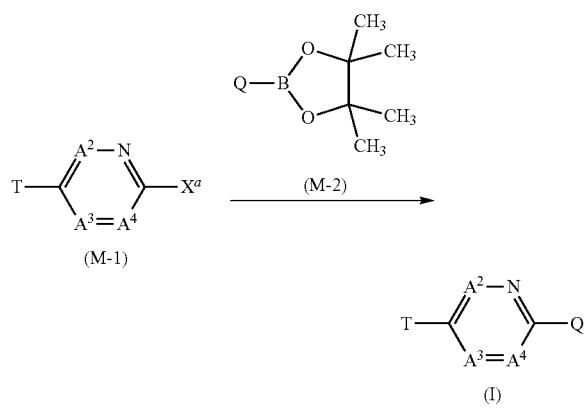

[wherein $X^a$ represents a chorine atom, a bromine atom, or an iodine atom, and the other symbols are the same as defined above.]

The reaction is usually carried out in a solvent. Examples of the solvent to be used in the reaction include ethers such as dimethoxyethane, 1,4-dioxane, tetrahydrofuran (hereinafter, referred to as THE), ethylene glycol dimethyl ether, and methyl tert-butyl ether (hereinafter, referred to as MTBE) (hereinafter, referred to as ethers); aromatic hydrocarbons such as toluene and xylene (hereinafter, referred to as aromatic hydrocarbons); polar aprotic solvents such as N-methyl pyrrolidone (hereinafter, referred to as NMP), dimethyl sulfoxide (hereinafter, referred to as DMSO) (hereinafter, referred to as polar aprotic solvents); water; and mixed solvents thereof.

Examples of the metal catalyst to be used in the reaction include palladium catalysts such as tetrakis(triphenylphosphine)palladium(0), [1,1'-bis(diphenylphosphino)ferrocene] palladium(II) dichloride, tris(dibenzylideneacetone)dipalladium(0), and palladium(II) acetate.

A ligand or a base may be added to the reaction as needed.

Examples of the ligand to be used in the reaction include triphenylphosphine, Xantphos, 2,2'-bis(diphenylphoshino)-1,1'-binaphthyl, 1,1'-bis(diphenylphoshino)ferrocene, 2-(dicyclohexylphosphino)-2',4',6'-triisopropyl-1,1'-biphenyl, 2-dicyclohexylphosphino-2',6'-dimethoxybiphenyl, 1,2-bis(diphenylphosphino)ethane, 2,2'-bipyridine, 2-aminoethanol, 8-hydroquinoline, and 1,10-phenanthroline.

Example of the base to be used in the reaction include organic bases such as triethylamine, diisopropylethylamine, pyridine, and 4-(dimethylamino)pyridine (hereinafter, referred to as organic bases), alkali metal carbonates such as sodium carbonate and potassium carbonate (hereinafter, referred to as alkali metal carbonates), tri-potassium phosphate, and potassium fluoride.

In the reaction, the compound (M-2) is usually used within a range of 1 to 10 molar ratio (s), the metal catalyst is usually used within a range of 0.01 to 0.5 molar ratios, the ligand is usually used within a range of 0.01 to 1 molar ratio (s), and the base is usually used within a range of 0.1 to 5 molar ratio(s), as opposed to 1 mole of the compound (M-1).

The reaction temperature of the reaction is usually within a range of −20 to 200° C. The reaction period of the reaction is usually within a range of 0.1 to 24 hours.

When the reaction is completed, water is added to reaction mixtures, and the reaction mixtures are extracted with organic solvent(s), and the organic layers are worked up (such as drying and concentration) to obtain the compound of the present invention.

Process 2

A compound represented by formula (I-Q1a) (hereinafter, referred to as Compound (I-Q1a)) may be prepared by reacting a compound represented by formula (M-3) (hereinafter, referred to as Compound (M-3)) with chloroacetaldehyde.

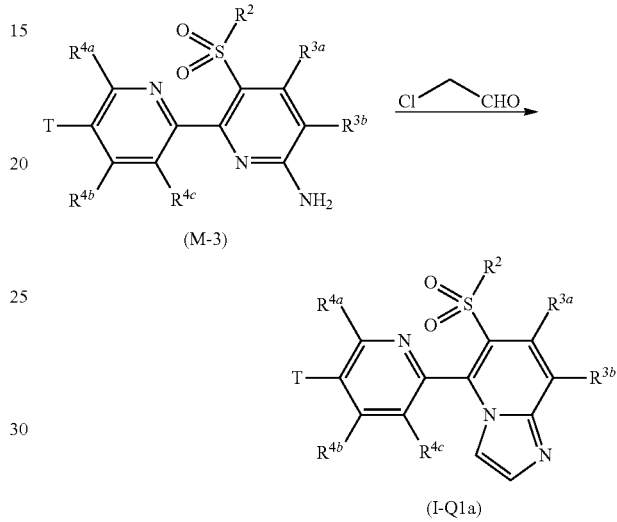

[wherein the symbols are the same as defined above.]

The reaction is usually carried out in a solvent.

Examples of the solvents to be used in the reaction include ethers; polar aprotic solvents; halogenated hydrocarbons such as dichloromethane and chloroform (hereinafter, referred to as halogenated hydrocarbons); nitriles such as acetonitrile (hereinafter, referred to as nitriles); alcohols such as methanol and ethanol (hereinafter, referred to as alcohols); water; and mixed solvents thereof.

An acid or a base may be added to the reaction, and examples of the acid include hydrogen chloride, p-toluenesulfonic acid, and 10-camphorsulfonic acid. Examples of the base include alkali metal carbonates and organic bases.

In the reaction, the acid or the base is usually used within a range of 0.1 to 10 molar ratio (s), and chloroacetaldehyde is usually used within a range of 1 to 10 molar ratio(s), as opposed to 1 mole of the compound (M-3).

The reaction temperature of the reaction is usually within a range of −20 to 150° C. The reaction period of the reaction is usually within a range of 0.5 to 24 hours.

When the reaction is completed, water is added to reaction mixtures, and the reaction mixtures are extracted with organic solvent(s), and the organic layers are worked up (such as drying and concentration) to obtain the compound (I-Q1a).

Process 3

A compound represented by formula (I-Q1b) (hereinafter, referred to as Compound (I-Q1b)) can be prepared by reacting a compound represented by formula (M-4) (hereinafter, referred to as Compound (M-4)) with a compound represented by formula (R-1) (hereinafter, referred to as Compound (R-1)).

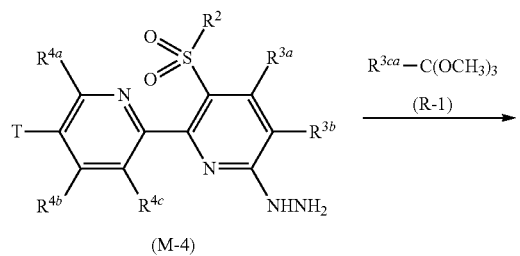

(M-4)

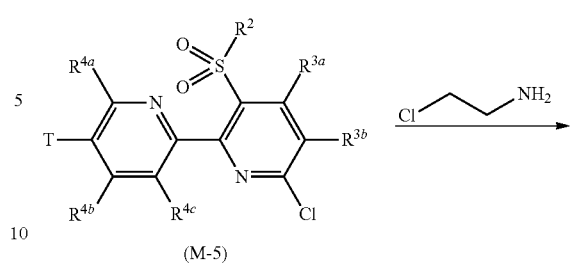

(M-5)

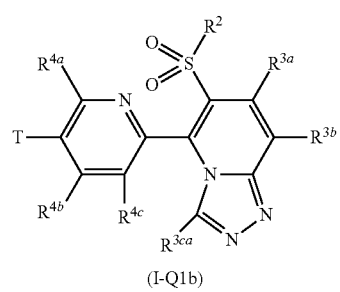

(I-Q1b)

[wherein R$^{3ca}$ represents a C1-C6 chain hydrocarbon group optionally having one or more substituents selected from Group B, a C3-C7 cycloalkyl group optionally having one or more substituents selected from Group E, a phenyl group optionally having one or more substituents selected from Group H, a five or six membered aromatic heterocyclic group optionally having one or more substituents selected from Group H, or a hydrogen atom, and the other symbols are the same as defined above.]

The reaction is usually carried out in a solvent. Examples of the solvents to be used in the reaction include ethers, polar aprotic solvents, halogenated hydrocarbons, nitriles, alcohols, water, and mixed solvents thereof.

An acid or a base may be added to the reaction, and examples of the acid include hydrogen chloride, p-toluenesulfonic acid, and 10-camphorsulfonic acid. Examples of the base includes alkali metal carbonates and organic bases.

In the reaction, the acid or the base is usually used within 0.1 to 10 molar ratios, and the compound (R-1) is usually used within a range of 1 to 10 molar ratio(s), as opposed to 1 mole of the compound (M-4).

The reaction temperature of the reaction is usually within a range of –20 to 150° C. The reaction period of the reaction is usually within a range of 0.5 to 24 hours.

When the reaction is completed, water is added to reaction mixtures, and the reaction mixtures are extracted with organic solvent(s), and the organic layers are worked up (such as drying and concentration) to obtain the compound (I-Q1b).

The compound (R-1) is a commercially available compound, or can be prepared according to a known method.

Process 4

A compound represented by formula (I-Q2a) (hereinafter, referred to as Compound (I-Q2a)) can be prepared by reacting a compound represented by formula (M-5) (hereinafter, referred to as Compound (M-5)) with 2-chloroethylamine.

(I-Q2a)

[wherein the symbols are the same as defined above.]

The reaction is usually carried out in a solvent. Examples of the solvent to be used in the reaction include ethers, polar aprotic solvents, halogenated hydrocarbons, nitriles, alcohols, water, and mixed solvents thereof.

The base may be added to the reaction, and examples of the base include alkali metal carbonates, and alkali metal hydrides such as sodium hydride (hereinafter, referred to as alkali metal hydrides) and organic bases.

In the reaction, the base is usually used within a range of 1 to 10 molar ratio(s), and 2-chloroethylamine is usually used within a range of 1 to 10 molar ratio(s), as opposed to 1 mole of the compound (M-5).

The reaction temperature of the reaction is usually within a range of –20 to 150° C. The reaction period of the reaction is usually within a range of 0.5 to 24 hours. When the reaction is completed, water is added to reaction mixtures, and the reaction mixtures are extracted with organic solvent(s), and the organic layers are worked up (such as drying and concentration) to obtain the compound (I-Q2a).

The compound (M-5) can be prepared, for example, according to the method described in WO 2016/121969.

Process 5

A compound represented by formula (I-Q2b) (hereinafter, referred to as Compound (I-Q2b)) can be prepared by reacting the compound (M-4) with 1,1'-carbonyldiimidazole.

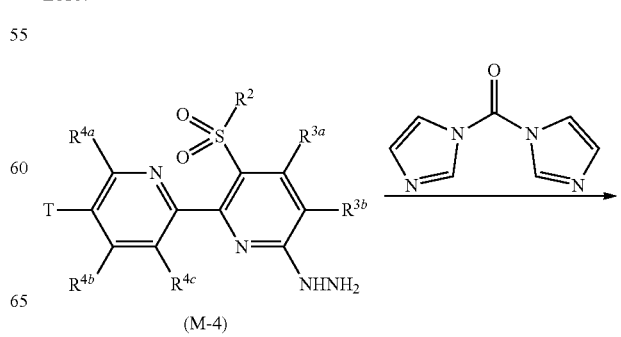

(M-4)

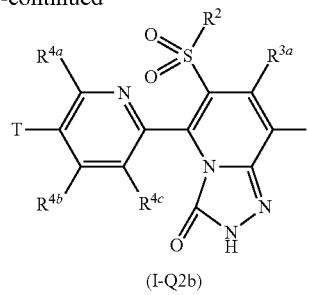

(I-Q2b)

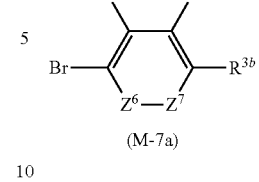

(M-7a)

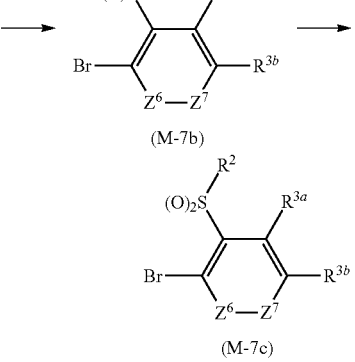

(M-7b)

(M-7c)

[wherein the symbols are the same as defined above.]

The reaction is usually carried out in a solvent. Examples of the solvent to be used in the reaction include ethers, polar aprotic solvents, halogenated hydrocarbons, nitriles, alcohols, and mixed solvents thereof.

In the reaction, 1,1'-carbonyldiimidazole is usually used within a range of 1 to 10 molar ratio(s) as opposed to 1 mole of the compound (M-4).

The reaction temperature of the reaction is usually within a range of −20 to 120° C. The reaction period of the reaction is usually within a range of 0.1 to 12 hours.

When the reaction is completed, water is added to reaction mixtures, and the reaction mixtures are extracted with organic solvent(s), and the organic layers are worked up (such as drying and concentration) to obtain the compound (I-Q2b).

Reference Process 1

The compound (M-2) can be prepared by reacting a compound represented by formula (M-7) with bis(pinacolato)diboron.

[wherein $Z^6$-$Z^7$ represents a group represented by formula Q1-1, a group represented by formula Q2-1, a group represented by formula Q3-1, or a group represented by formula Q4-1, and the other symbols are the same as defined above.]

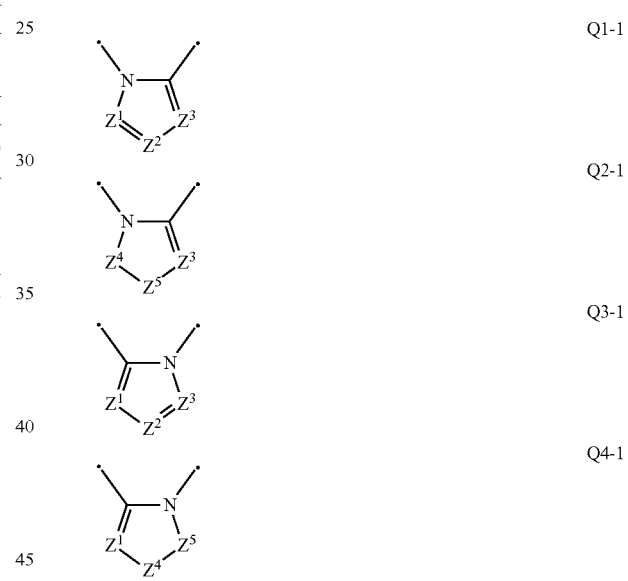

Q1-1

Q2-1

Q3-1

Q4-1

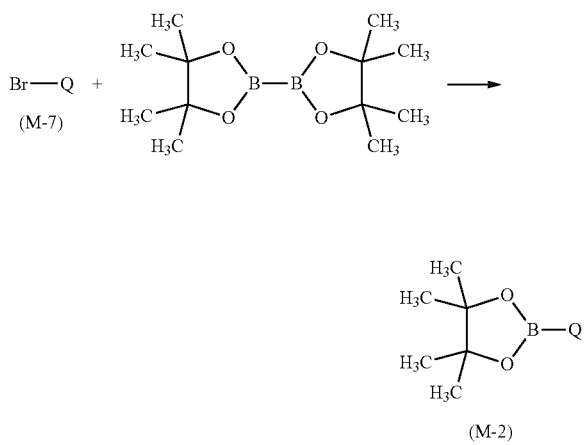

(M-7)

(M-2)

[wherein the symbols are the same as defined above.]

The reaction can be conducted, for example, according to the method described in Example 127 of WO 2015/153720.

Reference Process 2

A compound represented by formula (M-7b) (hereinafter, referred to as Compound (M-7b)) or a compound represented by formula (M-7c) (hereinafter, referred to as Compound (M-7c)) can be prepared by oxidizing a compound represented by formula (M-7a) (hereinafter, referred to as Compound (M-7a)).

[wherein the symbols are the same as defined above.]

These reactions can be conducted according to the method described in the process 1 of WO 2013/018928.

Reference Process 3

The compound (M-7a) can be prepared by reacting a compound represented by formula (M-8) (hereinafter, referred to as Compound (M-8)) with a compound represented by formula (R-2) (hereinafter, referred to as Compound (R-2)) in the presence of a base.

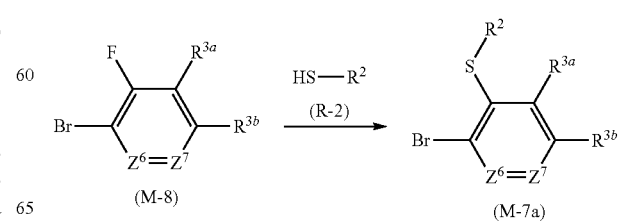

(M-8)

(R-2)

(M-7a)

[wherein the symbols are the same as defined above.]

The reaction can be conducted according to the method described in the process 5 of WO 2013/018928.

The compound (R-2) is a commercially available compound, or can be prepared according to a known method.

Reference Process 4

A compound represented by formula (M-8-Q1a) (hereinafter, referred to as Compound (M-8-Q1a)) can be prepared by reacting a compound represented by formula (M-9 (hereinafter, referred to as Compound (M-9)) with sodium azide.

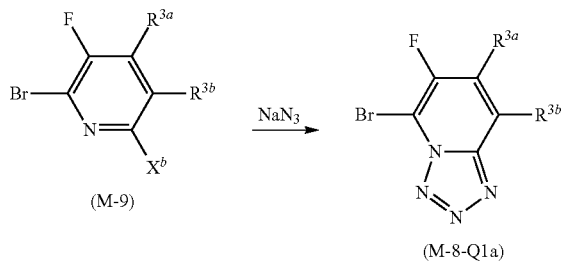

[wherein $X^b$ represents a fluorine atom or a chlorine atom, and the other symbols are the same as defined above.]

The reaction can be conducted according to the method described in Tetrahedron Letters, 2013, 54(5), 414. The compound (M-9) can be prepared, for example, according to the method described in WO 2012/083224.

Reference Process 5

A compound represented by formula (M-8-Q1b) (hereinafter, referred to as Compound (M-8-Q1b) can be prepared according to the following scheme.

having one or more substituents selected from Group B, a C3-C7 cycloalkyl group optionally having one or more substituents selected from Group E, a phenyl group optionally having one or more substituents selected from Group H, a five or six membered aromatic heterocyclic group optionally having one or more substituents selected from Group H, or a hydrogen atom, the other symbols are the same as defined above.]

This reference process comprises a step 1 for preparing a compound represented by formula (M-10) (hereinafter, referred to as Compound (M-10)) from the compound (M-9), and a step 2 for preparing the compound (M-8-Q1b) from the compound (M-10).

Firstly, the step 1 is explained.

The compound (M-10) can be prepared by reacting the compound (M-9) with ammonia. The reaction can be conducted according to the method described in Preparation Example 8 (1) of WO 2015/002211.

Next, the step 2 is explained.

The compound (M-8-Q1b) can be prepared by reacting the compound (M-10) with a compound represented by formula (R-3) (hereinafter, referred to as Compound (R-3)). The reaction can be conducted according to the method described in the Process 2.

The compound (R-3) is a commercially available compound, or can be prepared according to a known method.

Reference Process 6

A compound represented by formula (M-8-Q1d) (hereinafter, referred to as Compound (M-8-Q1d)), a compound represented by formula (M-8-Q1e) (hereinafter, referred to as Compound (M-8-Q1e)), a compound represented by formula (M-8-Q1f) (hereinafter, referred to as Compound (M-8-Q1f)) and a compound represented by formula (M-8-Q1g) (hereinafter, referred to as Compound (M-8-Q1g)) can be prepared according to the following scheme.

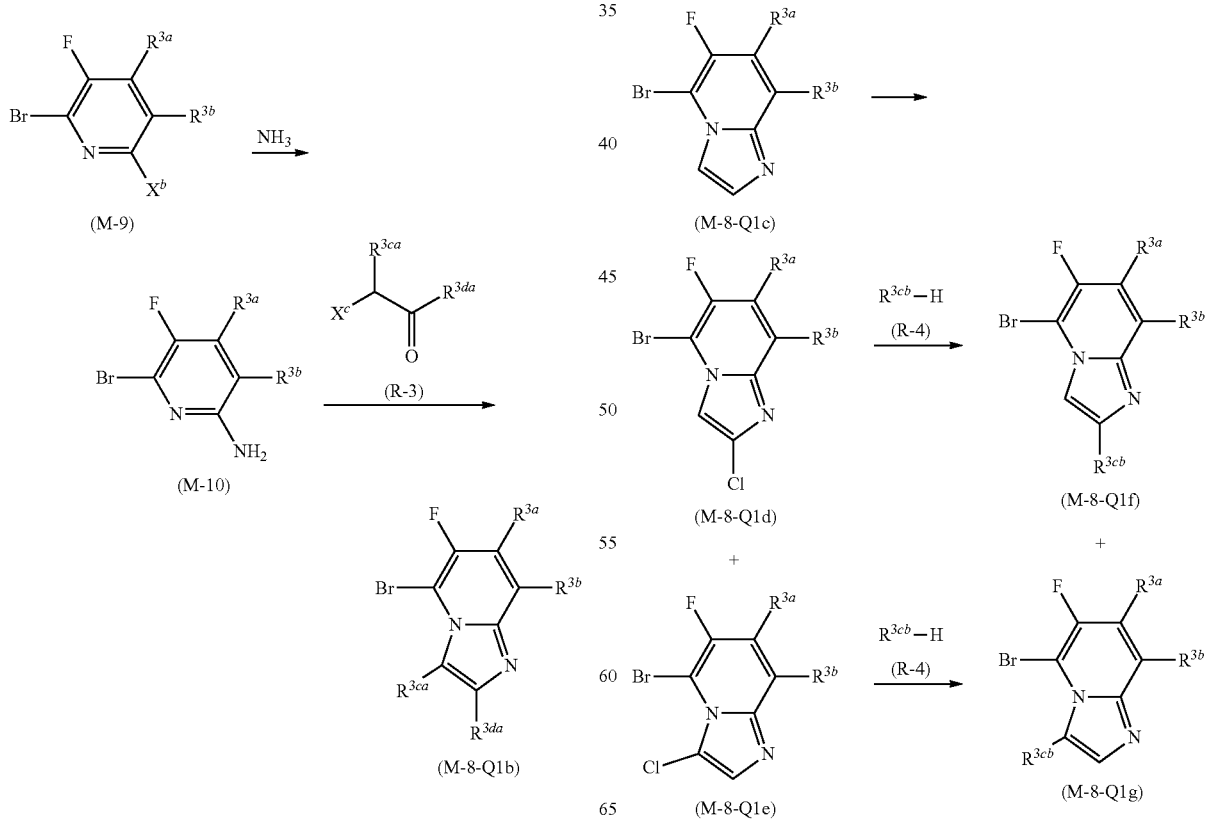

[wherein $X^c$ represents a chlorine atom, or a bromine atom, $R^{3da}$ represents a C1-C6 chain hydrocarbon group optionally

[wherein, $R^{3cb}$ represents $OR^{12}$, $NR^{11}R^{12}$, $NR^{11a}R^{12a}$, $NR^{29}NR^{11}R^{12}$, $NR^{29}OR^{11}$, $NR^{11}C(O)R^{13}$, $NR^{29}NR^{11}C(O)R^{13}$, $NR^{11}C(O)OR^{14}$, $NR^{29}NR^{11}C(O)OR^{14}$, $NR^{11}C(O)NR^{15}R^{16}$, or $NR^{29}NR^{11}C(O)NR^{15}R^{16}$, and the other symbols are the same as defined above.]

This reference process comprises a step 1 for preparing the compound (M-8-Q1d) and the compound (M-8-Q1e) from the compound (M-8-Q1d) as well as the step 2 for preparing the compound (M-8-Q1f) and the compound (M-8-Q1g) from the compound (M-8-Q1d) and the compound (M-8-Q1e).

Firstly, the step 1 is explained.

The compound (M-8-Q1d) and the compound (M-8-Q1e) can be prepared by reacting the compound (M-8-Q1c) with N-chlorosuccinimide.

The reaction can be conducted according to the method described in the PREPARATIVE EXAMPLE 60 of WO 2004/026867.

Next, the second step 2 is explained.

The compound (M-8-Q1f) can be prepared by reacting the compound (M-8-Q1d) with a compound represented by formula (R-4) (hereinafter, referred to as Compound (R-4)) in the presence of a base. The compound (M-8-Q1g) can be prepared by reacting the compound (M-8-Q1e) with the compound (R-4) in the presence of a base.

The reaction is usually carried out in a solvent.

Examples of the solvent to be used in the reaction include ethers, polar aprotic solvents, halogenated hydrocarbons, nitriles, and mixed solvents thereof.

A base may be added to the reaction, and examples of the base include alkali metal carbonates, and alkali metal hydrides such as sodium hydride, and organic bases.

In the reaction, the base is usually used within a range of 1 to 10 molar ratio(s), and the compound (R-4) is usually used within a range of 1 to 10 molar ratio(s), as opposed to 1 mole of the compound (M-8-Q1d) or the compound (M-8-Q1e).

The reaction temperature is usually within a range of −20 to 150° C. The reaction period of the reaction is usually within a range of 0.5 to 24 hours.

When the reaction is completed, water is added to reaction mixtures, and the reaction mixtures are extracted with organic solvent(s), and the organic layers are worked up (such as drying and concentration) to obtain the compound (Q-8-Q1f9 or the compound (M-8-Q1g).

The compound (R-4) is a commercially available compound, or can be prepared according to a known method.

Reference Process 7

A compound represented by formula (M-8-Q1h) (hereinafter, referred to as Compound (M-8-Q1h)) can be prepared according to the following scheme.

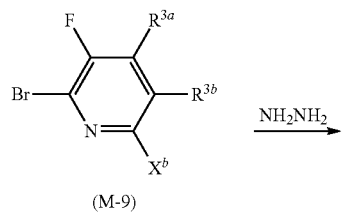

(M-9)

$\xrightarrow{NH_2NH_2}$

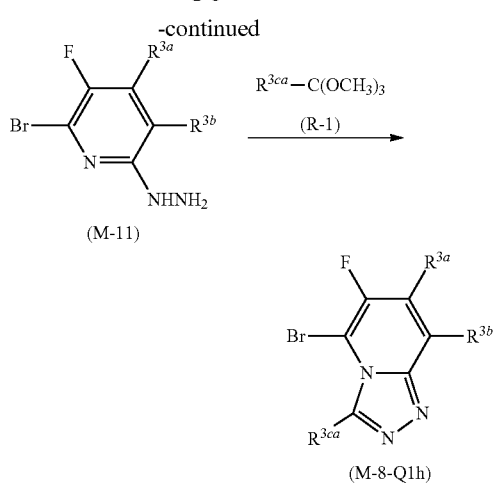

[wherein the symbols are the same as defined above.]

This reference process comprises a step 1 for preparing a compound represented by formula (M-11) (hereinafter, referred to as Compound (M-11)) from the compound (M-9), and a step 2 for preparing the compound (M-8-Q1h) from the compound (M-11).

Firstly, the step 1 is explained. The compound (M-11) can be prepared by reacting the compound (M-9) with hydrazine.

The reaction can be conducted according to the method described in Example 2 of WO 2013/074390.

Next, the step 2 is explained. The reaction can be conducted according to the method described in the Process 3.

The compound represented by formula (M-8-Q1k) and the compound represented by formula (M-8-Q1m) can be prepared according to the following scheme.

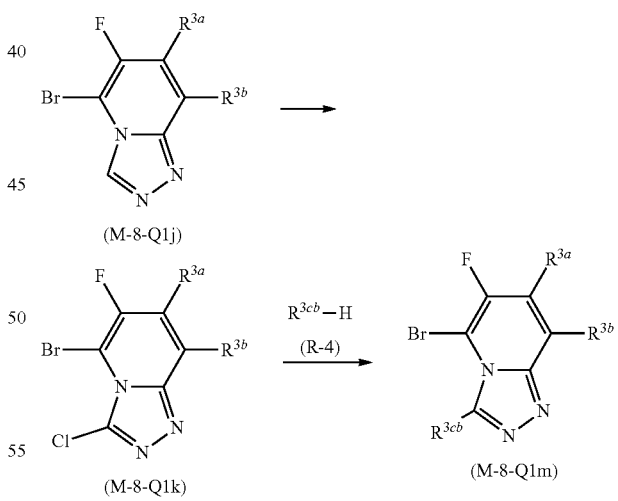

[wherein the symbols are the same as defined above.]

These reactions can be conducted according to the method described in the Reference process 6.

Reference Process 8

A compound represented by formula (M-8-Q2a) (hereinafter, referred to as Compound (M-8-Q2a)) can be prepared by reacting the compound (M-9) with a compound represented by formula (R-5) (hereinafter, referred to as Compound (R-5)).

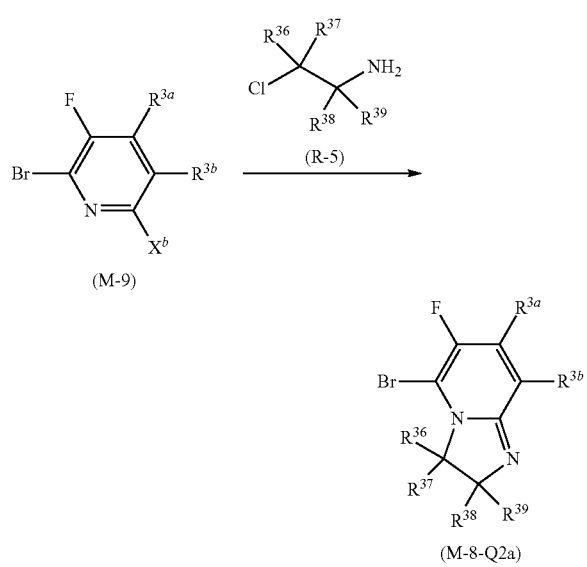

(M-9)

(M-8-Q2a)

[wherein the symbols are the same as defined above.]

The reaction can be conducted according to the method described in the Process 4.

The compound (R-5) is a commercially available compound, or can be prepared according to the known method.

Reference Process 9

A compound represented by formula (M-8-Q2b) (hereinafter, referred to as Compound (M-8-Q2b)) can be prepared by reacting a compound represented by formula (M-10) (hereinafter, referred to as Compound (M-10)) with a compound represented by formula (R-6) (hereinafter, referred to as Compound (R-6)).

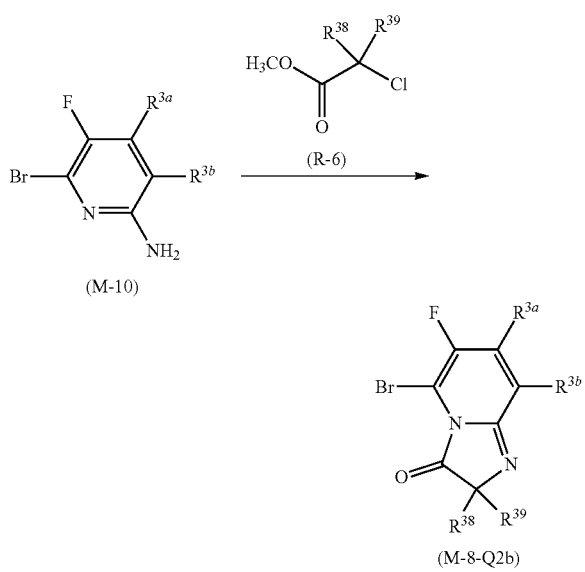

(M-10)

(M-8-Q2b)

[wherein the symbols are the same as defined above.]

The reaction is usually carried out in a solvent. Examples of the base to be used in the reaction include polar aprotic solvents, halogenated hydrocarbons, nitriles, alcohols, and mixes solvents thereof.

A base may be added to the reaction, and examples of the base include alkali metal carbonates, alkali metal hydrides, and organic bases.

In the reaction, the base is usually used within a range of 1 to 10 molar ratios, and the compound (R-6) is usually used within a range of 1 to 10 molar ratio (s), as opposed to 1 mole of the compound (M-10).

The reaction temperature is usually within a range of −20 to 150° C. The reaction period of the reaction is usually within a range of 0.5 to 24 hours.

When the reaction is completed, water is added to the reaction mixtures, and the reaction mixtures are extracted with organic solvent(s), and the organic layers are worked up (such as drying and concentration) to obtain the compound (M-8-Q2b).

The compound (R-6) is a commercially available compound, or can be prepared according to a known method.

Reference Process 10

A compound represented by formula (M-8-Q2) (hereinafter, referred to as Compound (M-8-Q2c)) can be prepared by reacting the compound (M-10) with a compound represented by formula (R-7) (hereinafter, referred to as Compound (R-7)).

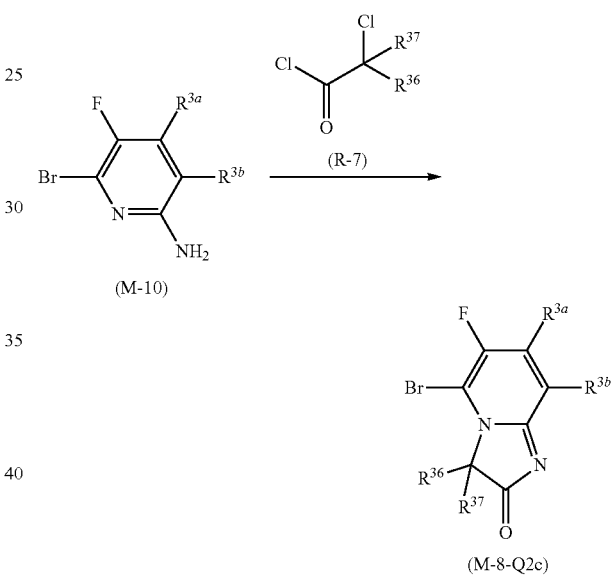

(M-10)

(M-8-Q2c)

[wherein the symbols are the same as defined above.]

The reaction is usually carried out in a solvent. Examples of the solvent to be used in the reaction include polar aprotic solvents, halogenated hydrocarbons, nitriles, alcohols, and mixed solvents thereof.

A base may be added to the reaction, and examples of the base include alkali metal carbonates, alkali metal hydrides, and organic bases.

In the reaction, the base is usually used within a range of 1 to 10 molar ratio(s), and the compound (R-7) is usually used within range of 1 to 10 molar ratio(s), as opposed to 1 mole of the compound (M-10).

The reaction temperature is usually within a range of −20 to 150° C. The reaction period of the reaction is usually within a range of 0.5 to 24 hours.

When the reaction is completed, water is added to the reaction mixtures, and the reaction mixtures are extracted with organic solvent(s), and the organic layers are worked up (such as drying and concentration) to obtain the compound (M-8-Q2c).

The compound (R-7) is a commercially available compound, or can be prepared according to a known method.

Reference Process 11

A compound represented by formula (M-8-Q2e) (hereinafter, referred to as Compound (M-8-Q2e)) and a compound represented by formula (M-8-Q2f) (hereinafter, referred to as Compound (M-8-Q2f)) can be prepared according to the following scheme.

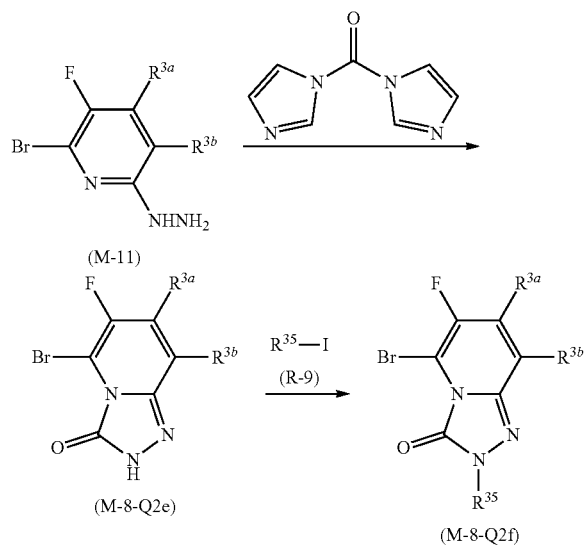

[wherein the symbols are the same as defined above.]

This reference process comprises a step 1 for preparing the compound (M-8-Q2e) from the compound (Mil), and a step 2 for preparing the compound (M-8-Q2f) from the compound (M-8-Q2e).

Firstly, the step 1 is explained.

The compound (M-8-Q2e) can be prepared by reacting the compound (M-11) with 1,1'-carbonyldiimidazole.

The reaction can be conducted according to the method described in the Process 5.

Next, the step 2 is explained.

The compound (M-8-Q2f) can be prepared by reacting the compound (M-8-Q2e) with a compound represented by formula (R-9) (hereinafter, referred to as Compound (R-9)).

The reaction can be conducted according to the method described in Bioorganic and Medicinal Chemistry Letters, 2015, 25(23), 5524, WO 2005/85226, U.S. Publication No. 2012/10192, or European Publication No. 2322176.

The compound (R-9) is a commercially available compound, or can be prepared according to a known method.

Reference Process 12

The compound (M-3) can be prepared by reacting the compound (M-5) with ammonia.

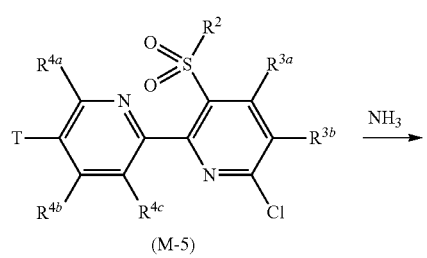

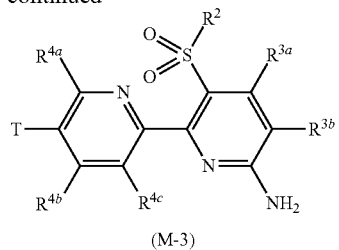

[wherein the symbols are the same as defined above.]

The reaction can be conducted according to the method described in the Reference process 5 for preparing the compound (M-10) from the compound (M-9).

Reference Process 13

The compound (M-4) can be prepared by reacting the compound (M-5) with hydrazine.

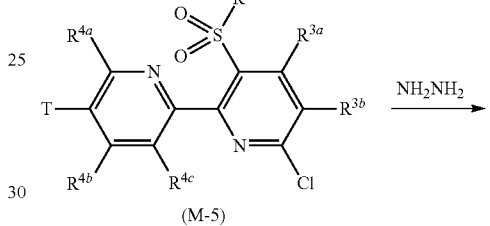

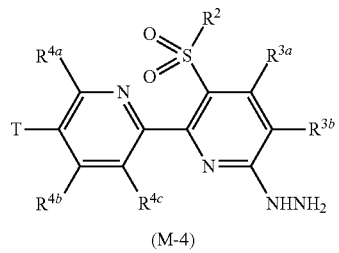

[wherein the symbols are the same as defined above.]

The reaction can be conducted according to the method described in the Process 3 of WO 2015/002211.

Reference Process 14

A compound represented by formula (M-1a) (hereinafter, referred to as Compound (M-1a)) can be prepared by reacting a compound represented by formula (M-20a) (hereinafter, referred to as Compound (M-20a)) with a compound represented by formula (R-10) (hereinafter, referred to as Compound (R-10)) in the presence of a base.

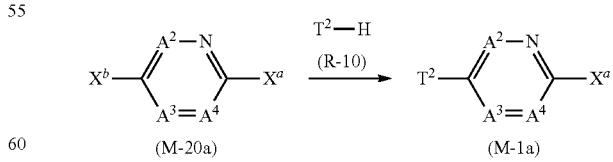

[wherein $T^2$ represents $OR^1$, $NR^1R^{24}$, a group represented by formula T-5, a group represented by formula T-6, a group represented by formula T-7, or a group represented by formula T-8, and the other symbols are the same as defined above.]

The reaction is usually carried out in a solvent. Examples of the solvent to be used in the reaction include ethers, aromatic hydrocarbons, nitriles, polar aprotic solvents, and mixed solvents thereof.

Examples of the base to be used in the reaction include alkali metal carbonates, and alkali metal hydrides.

In the reaction, the compound (R-10) is usually used within a range of 1 to 2 molar ratio (s), and the base is usually used within a range of 1 to 10 molar ratio (s), as opposed to 1 mole of the compound (M-20a).

The reaction temperature is usually within a range of −20 to 150° C. The reaction period of the reaction is usually within a range of 0.5 to 24 hours.

When the reaction is completed, water is added to the reaction mixtures, and the reaction mixtures are extracted with organic solvent(s), and the organic layers are worked up (such as drying and concentration) to obtain the compound of the present invention.

The compound (R-10) and the compound (M-20a) are commercially available compounds, or can be prepared according to the known method.

Reference Process 15

A compound represented by formula (M-1b) (hereinafter, referred to as Compound (M-1b)) can be prepared by reacting a compound represented by formula (M-20b) (hereinafter, referred to as Compound (M-20b)) with a compound represented by formula (R-11) (hereinafter, referred to as Compound (R-11)).

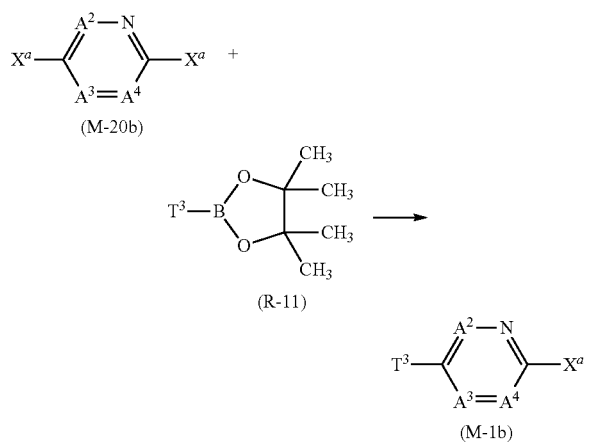

[wherein $T^3$ represents a group represented by formula T-1, a group represented by formula T-2, a group represented by formula T-3, a group represented by formula T-4, a group represented by formula T-9, a group represented by formula T-10, a group represented by formula T-11, or a group represented by formula T-12, and the other symbols are the same as defined above.]

The reaction can be conducted by using the compound (M-20b) instead of the compound (M-1), and the compound (R-11) instead of the compound (M-2), according to the method described in the Process 1.

The compound (R-11) and the compound (M-20b) are commercially available compounds, or can be prepared according to the known method.

Reference Process 16

A compound represented by a formula (M-1c9 (hereinafter, referred to as Compound (M-1c)) can be prepared by reacting a compound represented by formula (M-20c) (hereinafter, referred to as Compound (M-20c)) with a compound represented by formula (R-12) (hereinafter, referred to as Compound (R-12)).

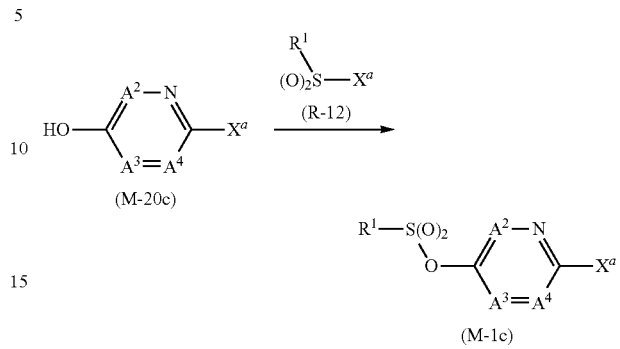

[wherein the symbols are the same as defined above.]

The reactions can be conducted according to the method described in the Preparation Example 1(1) of WO 2016/125621.

The compound (R-12) and the compound (M-20c) are commercially available compounds, or can be prepared according to the known method.

Reference Process 17

A compound represented by formula (M-1d) (hereinafter, referred to as Present compound (M-1d)) can be prepared by reacting the compound (M-20b) with a compound represented by formula (R-13) (hereinafter, referred to as Compound (R-13)) in the presence of a copper.

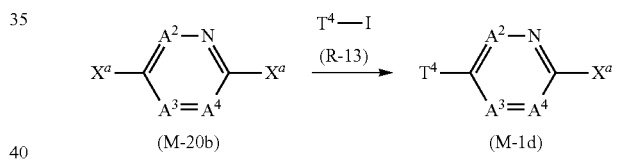

[wherein $T^4$ represents a C1-C10 chain hydrocarbon group optionally having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, or a C3-C7 cycloalkyl group having one or more substituents selected from Group G, and the other symbols are the same as defined above.]

The reaction is usually carried out in a solvent. Examples of the solvents to be used in the reaction include aromatic hydrocarbons, polar aprotic solvents, and mixed solvents thereof.

In the reaction, the compound (R-13) is usually used within a range of 1 to 10 molar ratio(s), and the copper is usually used within the range of 1 to 10 molar ratio(s), as opposed to 1 mole of the compound (M-20b).

The reaction temperature is usually within a range of 40 to 200° C. The reaction period of the reaction is usually within a range of 0.1 to 24 hours.

When the reaction is completed, water is added to the reaction mixtures, and the reaction mixtures are extracted with organic solvent(s), and the organic layers are worked up (such as drying and concentration) to obtain the compound (M-1d).

The compound (R-13) is a commercially available compound, or can be prepared according to the known method.

Reference Process 18

A compound represented by formula (M-1e) (hereinafter, referred to as Compound (M-1e)) can be prepared by reacting a compound represented by formula (M-20d) (hereinafter, referred to as Compound (M-20d)) with a compound represented by a formula (R-14) (hereinafter, referred to as Compound (R-14)).

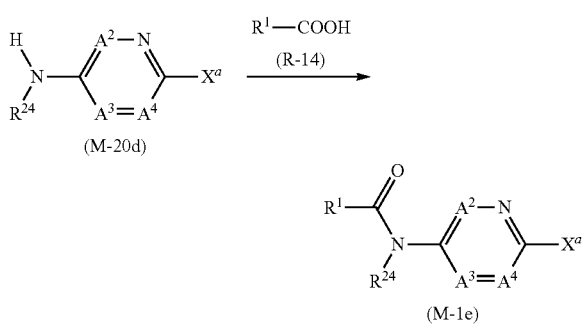

[wherein the symbols are the same as defined above.]

The reaction can be conducted according to the method described in the Preparation Examples 6(1) of WO 2014/021468.

The compound (M-20d) and the compound (R-14) are commercially available compounds, or can be prepared according to the known method.

Reference Process 19

A compound represented by formula (M-1f) (hereinafter, referred to as Compound (M-1f)) can be prepared by reacting the compound (M-20b) with a compound represented by formula (R-15) (hereinafter, referred to as Compound (R-15)) in the presence of a base.

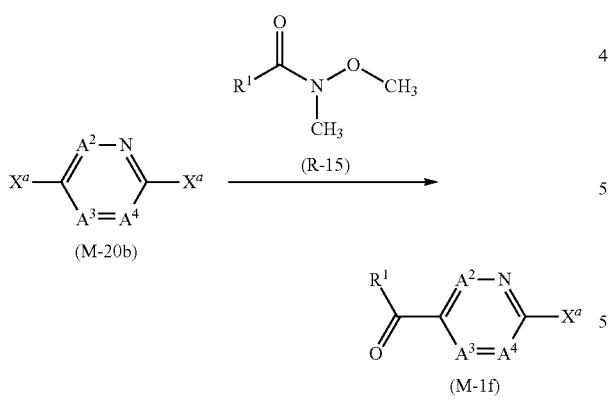

[wherein the symbols are the same as defined above.]

The reaction can be conducted according to the method described in Synthesis, 2008, 3707.

The compound (R-15) is a commercially available compound, or can be prepared according to a known method.

Reference Process 20

A compound represented by formula (M-1g) (hereinafter, referred to as Compound (M-1g)) can be prepared by reacting a compound represented by formula (M-20e) (hereinafter, referred to as Compound (M-20e)) with a compound represented by formula (R-16) (hereinafter, referred to as Compound (R-16)) in the presence of a condensing agent.

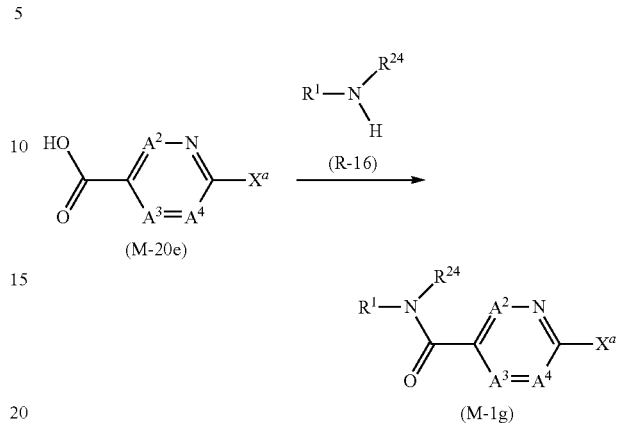

[wherein the symbols are the same as defined above.]

The reaction can be conducted according to the method described in the Preparation Example 6(1) of WO 2014/021468.

The compound (M-20e) and the compound (R-16) are commercially available compounds, or can be prepared according to the known method.

Reference Process 21

A compound represented by formula (M-1h) (hereinafter, referred to as Compound (M-1h)) can be prepared by reacting a compound represented by formula (M-20f) (hereinafter, referred to as Compound (M-20f)) with a compound represented by formula (R-17) (hereinafter, referred to as Compound (R-17)).

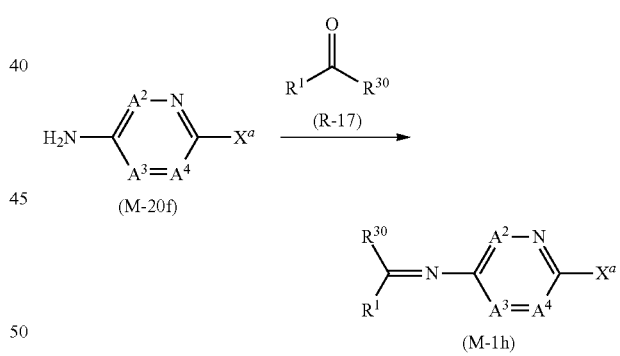

[wherein the symbols are the same as defined above.]

The reaction is usually carried out in a solvent. Examples of the solvent to be used in the reaction include ethers, aliphatic halogenated hydrocarbons, aromatic hydrocarbons, polar aprotic solvents, and mixed solvents thereof.

An acid may be added to the reaction as needed, and examples of the acid include p-toluenesulfonic acid and 10-camphorsulfonic acid.

In the reaction, the compound (R-17) is usually used within a range of 1 to 10 molar ratio (s), and the acid is usually used within a range of 0.1 to 10 molar ratios, as opposed to 1 mole of the compound (M-20f).

The reaction temperature is usually within a range of −20 to 180° C. The reaction period of the reaction is usually within a range of 0.1 to 24 hours.

When the reaction is completed, water is added to the reaction mixtures, and the reaction mixtures are extracted with organic solvent(s), and the organic layers are worked up (such as drying and concentration) to obtain the compound (M-1h).

The compound (M-20f) and the compound (R-17) are commercially available compounds, or can be prepared according to the known method.

Reference Process 22

A compound represented by formula (M-1i) (hereinafter, referred to as Compound (M-1i)) can be prepared by reacting a compound represented by formula (M-20g) (hereinafter, referred to as Compound (M-20g)) with a compound represented by formula (R-18) (hereinafter, referred to as Compound (R-18)) in the presence of a base.

The compound (R-18) and the compound (M-20g) are commercially available compounds, or can be prepared according to the known method.

Reference Process 23

A compound represented by formula (M-1j) (hereinafter, referred to as Compound (M-1j)), a compound represented by formula (M-1k) (hereinafter, referred to as Compound (M-1k)), a compound represented by formula (M-1m) (hereinafter, referred to as Compound ((M-1m)) can be prepared according to the following scheme.

[wherein the symbols are the same as defined above.]

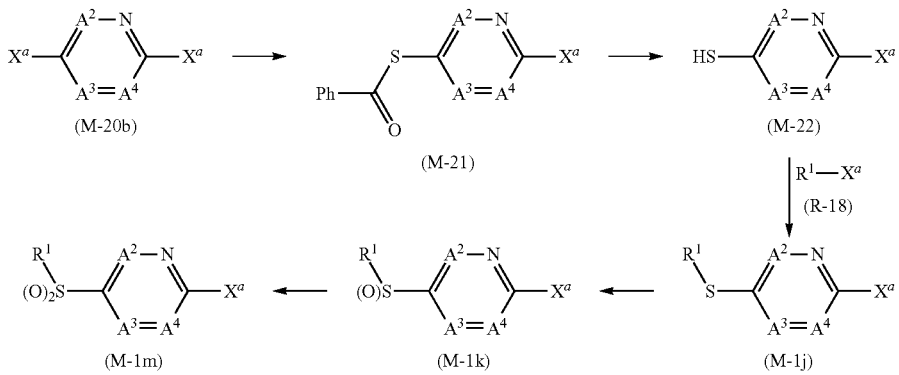

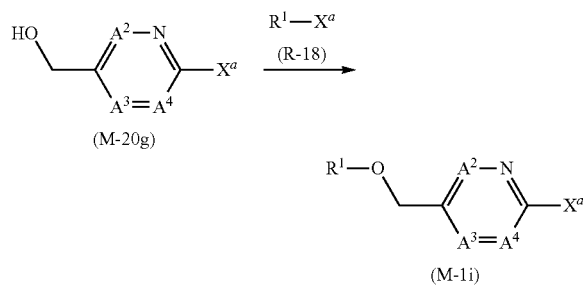

[wherein the symbols are the same as defined above.]

The reaction is usually carried out in a solvent. Examples of the solvent to be used in the reaction include ethers, aromatic hydrocarbons, polar aprotic solvents, and mixed solvents thereof.

Examples of the base to be used in the reaction include organic bases, alkali metal hydrides, and alkali metal carbonates.

In the reaction, the compound (R-18) is usually used within a range of 1 to 10 molar ratio (s), and the base is usually used within a range of 0.1 to 5 molar ratios, as opposed to 1 mole of the compound (M-20g).

The reaction temperature is usually within a range of −20 to 120° C. The reaction period of the reaction is usually within a range of 0.1 to 24 hours.

When the reaction is completed, water is added to the reaction mixtures, and the reaction mixtures are extracted with organic solvent(s), and the organic layers are worked up (such as drying and concentration) to obtain the compound (M-1i).

This reference process comprises a step 1 for preparing a compound represented by formula (M-21) (hereinafter, referred to as Compound (M-21)) from the compound (M-20b), a step 2 for preparing a compound represented by formula (M-22) (hereinafter, referred to as Compound (M-22) from the Compound (M-21), a step 3 for preparing the compound (M-1j) from the compound (M-22), and a step 4 for preparing the compound (M-1k) and the compound (M-1m) from the compound (M-1j).

The step 1 is explained. The compound (M-21) can be prepared by reacting the Compound (M-20b) with thiobenzoic acid in the presence of a copper catalyst and a base. The reaction can be conducted according to the method described in the Preparation Examples 24(4) of WO 2013/018928.

The step 2 is explained. The compound (M-22) can be prepared by hydrolyzing the compound (M-21). The reaction can be conducted according to the method described in the Preparation Examples 24(5) of WO 2013/018928.

The step 3 is explained. The compound (M-1j) can be prepared by reacting the compound (M-22) with the compound (R-18) in the presence of a base. The reaction can be conducted according to the method described in the Reference process 22.

The step 4 is explained. The compound (M-1k) and the compound (M-1m) can be prepared by oxidizing the compound (M-1j). The reaction can be conducted according to the method described in the Process 1 of WO 2013/018928.

Next, specific examples of the present compounds are shown below.

Herein, Me represents a methyl group, Et represents an ethyl group, Pr represents a propyl group, i-Pr represents an isopropyl group, c-Pr represents a cyclopropyl group, c-c-Bu represents a cyclobutyl group, Ph represents a phenyl group, Py2 represents a 2-pyridyl group, Py3 represents a 3-pyridyl group. When the c-Pr, Ph, Py2, Py3, and Py4 have any substituents, the substituents are described together with a substitution position before the symbol. For example, 4-CF$_3$—Py2 represents a 4-(trifluoromethyl)-2-pyridyl group, and 3,5-(CF$_3$)$_2$-Ph represents a 3,5-bis(trifluoromethyl)phenyl group.

a compound represented by formula (L-1):

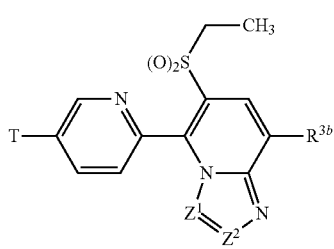

wherein Z$^2$ and Z$^2$ each represents CH, and R$^3$ represents a hydrogen atom, and T represents any substituents indicated in Table 1 to Table 6 (hereinafter, referred to as Compound Class SX1).

TABLE 1

CF$_3$
CHF$_2$
CH$_2$CF$_3$
CF$_2$CF$_3$
CH$_2$CF$_2$CF$_3$
CF$_2$CF$_2$CF$_3$
CF$_2$CF$_2$CF$_2$CF$_3$
CF$_2$CF$_2$CF$_2$CF$_2$CF$_3$
OCF$_3$
OCHF$_2$
OCH$_2$CF$_3$
OCH$_2$CHF$_2$
OCF$_2$CF$_3$
OCH(CH$_3$)CF$_3$
OCH$_2$CF$_2$CHF$_2$
OCH$_2$CF$_2$CF$_3$
OCF$_2$CF$_2$CF$_3$
OCH$_2$CF$_2$CHFCF$_3$
OCH$_2$CF$_2$CF$_2$CF$_3$
OCF$_2$CF$_2$CF2CF$_3$
OCH$_2$CF$_2$CF$_2$CF$_2$CF$_3$

TABLE 2

SCF$_3$
SCH$_2$CF$_3$
SCF$_2$CF$_3$
SCH$_2$CF$_2$CF$_3$
SCF$_2$CF$_2$CF$_3$
SCH$_2$CF$_2$CF$_2$CF$_3$
SCF$_2$CF$_2$CF$_2$CF$_3$
S(O)CF$_3$
S(O)CH$_2$CF$_3$
S(O)CF$_2$CF$_3$
S(O)CH$_2$CF$_2$CF$_3$
S(O)CF$_2$CF$_2$CF$_3$
S(O)CH$_2$CF$_2$CF$_2$CF$_3$
S(O)CF$_2$CF$_2$CF$_2$CF$_3$
S(O)$_2$CF$_3$
S(O)$_2$CH$_2$CF$_3$
S(O)$_2$CF$_2$CF$_3$
S(O)$_2$CH$_2$CF$_2$CF$_3$
S(O)$_2$CF$_2$CF$_2$CF$_3$
S(O)$_2$CH$_2$CF$_2$CF$_2$CF$_3$
S(O)$_2$CF$_2$CF$_2$CF$_2$CF$_3$

TABLE 3

NHCH$_2$CF$_3$
NHCH$_2$CF$_2$CF$_3$
NHCH$_2$CF$_2$CF$_2$CF$_3$
NMeCH$_2$CF$_3$
NMeCH$_2$CF$_2$CF$_3$
NMeCH$_2$CF$_2$CF$_2$CF$_3$
NEtCH$_2$CF$_3$
NEtCH$_2$CF$_2$CF$_3$
NEtCH$_2$CF$_2$CF$_2$CF$_3$
OS(O)$_2$CF$_3$
OS(O)$_2$CF$_2$CF$_3$
OS(O)$_2$CF$_2$CF$_2$CF$_3$
CH$_2$OCF$_3$
CH$_2$OCH$_2$CF$_3$
CH$_2$OCF$_2$CF$_3$
C(O)CF$_3$
C(O)CF$_2$CF$_3$
C(O)CF$_2$CF$_2$CF$_3$
C(O)NMeCH$_2$CF$_3$
NMeC(O)CF$_3$
N=CEtCH$_2$CF$_3$

TABLE 4

3-CF$_3$—Ph
4-CF$_3$—Ph
3,5-(CF$_3$)$_2$—Ph
3-SCF$_3$—Ph
3-S(O)CF$_3$—Ph
3-S(O)$_2$CF$_3$—Ph
4-SCF$_3$—Ph
4-S(O)CF$_3$—Ph
4-S(O)$_2$CF$_3$—Ph

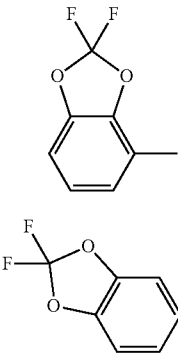

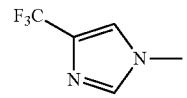

TABLE 5

4-CF$_3$—Py2
5-CF$_3$—Py2
4-SCF$_3$—Py2
4-S(O)CF$_3$—Py2
4-S(O)$_2$CF$_3$—Py2
5-SCF$_3$—Py2
5-S(O)CF$_3$—Py2
5-S(O)$_2$CF$_3$—Py2
5-NMeCH$_2$CF$_3$—Py2

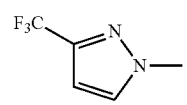

TABLE 5-continued

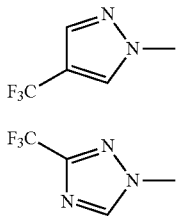

TABLE 6

5-CF₃—Py3
6-CF₃—Py3
5-SCF₃—Py3
5-S(O)CF₃—Py3
5-S(O)₂CF₃—Py3
6-SCF₃—Py3
6-S(O)CF₃—Py3
6-S(O)₂CF₃—Py3
6-NMeCH₂CF₃—Py3

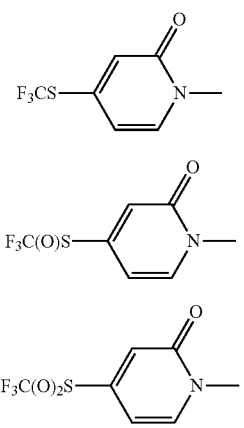

a compound (L-1) wherein $Z^1$ and $Z^2$ each represents CH, and $R^{3b}$ represents a trifluoromethyl group, and T represents any substituents indicated in Table 1 to Table 6 (hereinafter, referred to as Compound Class SX2).

a compound (L-1) wherein $Z^1$ represents CH, $Z^2$ represents a nitrogen atom, and $R^{3b}$ represents a hydrogen atom, and T represents any substituents indicated in Table 1 to Table 6 (hereinafter, referred to as Compound Class SX3).

a compound (L-1) wherein $Z^1$ represents CH, $Z^2$ represents a nitrogen atom, and $R^{3b}$ represents a trifluoromethyl group, and T represents any substituents indicated in Table 1 to Table 6 (hereinafter, referred to as Compound Class SX4).

a compound (L-1) wherein $Z^1$ represents a nitrogen atom, $Z^2$ represents CH, and $R^{3b}$ represents a hydrogen atom, and T represents any substituents indicated in Table 1 to Table 6 (hereinafter, referred to as Compound Class SX5).

a compound (L-1) wherein $Z^1$ represents a nitrogen atom, $Z^2$ represents CH, and $R^{3b}$ represents a trifluoromethyl group, and T represents any substituents indicated in Table 1 to Table 6 (hereinafter, referred to as Compound Class SX6).

a compound (L-1) wherein $Z^1$ and $Z^2$ each represents a nitrogen atom, and $R^{3b}$ represents a hydrogen atom, and T represents any substituents indicated in Table 1 to Table 6 (hereinafter, referred to as Compound Class SX7).

a compound (L-1) wherein $Z^1$ and $Z^2$ each represents a nitrogen atom, and $R^{3b}$ represents a trifluoromethyl group, and T represents any substituents indicated in Table 1 to Table 6 (hereinafter, referred to as Compound Class SX8).

a compound represented by formula (L-2):

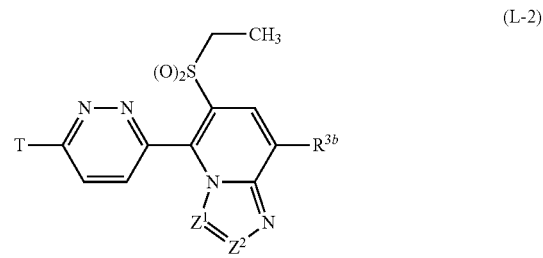

wherein $Z^1$ and $Z^2$ each represents CH, and $R^{3fc}$ represents a hydrogen atom, and T represents any substituents indicated in Table 1 to Table 6 (hereinafter, referred to as Compound Class SX9).

a compound (L-2) wherein $Z^1$ and $Z^2$ each represents CH, and $R^{3b}$ represents a trifluoromethyl group, and T represents any substituents indicated in Table 1 to Table 6 (hereinafter, referred to as Compound Class SX10).

a compound (L-2) wherein $Z^1$ represents CH, $Z^2$ represents a nitrogen atom, and $R^{3b}$ represents a hydrogen atom, and T represents any substituents indicated in Table 1 to Table 6 (hereinafter, referred to as Compound Class SX11).

a compound (L-2) wherein $Z^1$ represents CH, $Z^2$ represents a nitrogen atom, and $R^{3b}$ represents a trifluoromethyl group, and T represents any substituents indicated in Table 1 to Table 6 (hereinafter, referred to as Compound Class SX12).

a compound (L-2) wherein $Z^1$ represents a nitrogen atom, $Z^2$ represents CH, and $R^{3b}$ represents a hydrogen atom, and T represents any substituents indicated in Table 1 to Table 6 (hereinafter, referred to as Compound Class SX13).

a compound (L-2) wherein $Z^1$ represents a nitrogen atom, $Z^2$ represents CH, and $R^{3b}$ represents a trifluoromethyl group, and T represents any substituents indicated in Table 1 to Table 6 (hereinafter, referred to as Compound Class SX14).

a compound (L-2) wherein $Z^1$ and $Z^2$ each represents a nitrogen atom, and $R^{3b}$ represents a hydrogen atom, and T represents any substituents indicated in Table 1 to Table 6 (hereinafter, referred to as Compound Class SX15).

a compound (L-2) wherein $Z^1$ and $Z^2$ each represents a nitrogen atom, and $R^{3b}$ represents a trifluoromethyl group, and T represents any substituents indicated in Table 1 to Table 6 (hereinafter, referred to as Compound Class SX16).

a compound represented by formula (L-3):

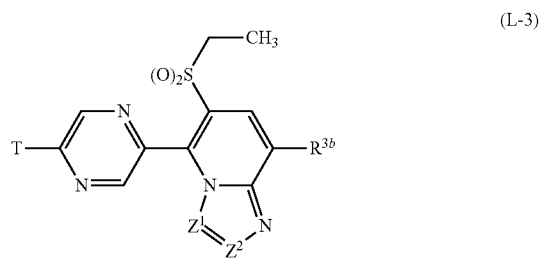

wherein $Z^1$ and $Z^2$ each represents CH, and $R^{3b}$ represents a hydrogen atom, and T represents any substituents indicated in Table 1 to Table 6 (hereinafter, referred to as Compound Class SX17).

a compound (L-3) wherein $Z^1$ and $Z^2$ each represents CH, and $R^{3b}$ represents a trifluoromethyl group, and T represents any substituents indicated in Table 1 to Table 6 (hereinafter, referred to as Compound Class SX18).

a compound (L-3) wherein $Z^1$ represents CH, $Z^2$ represents a nitrogen atom, and $R^{3b}$ represents a hydrogen atom, and T represents any substituents indicated in Table 1 to Table 6 (hereinafter, referred to as Compound Class SX19).

a compound (L-3) wherein $Z^1$ represents CH, $Z^2$ represents a nitrogen atom, and $R^{3b}$ represents a trifluoromethyl group, and T represents any substituents indicated in Table 1 to Table 6 (hereinafter, referred to as Compound Class SX20).

a compound (L-3) wherein $Z^1$ represents a nitrogen atom, $Z^2$ represents CH, and $R^{3b}$ represents a hydrogen atom, and T represents any substituents indicated in Table 1 to Table 6 (hereinafter, referred to as Compound Class SX21).

a compound (L-3) wherein $Z^1$ represents a nitrogen atom, $Z^2$ represents CH, and $R^{3b}$ represents a trifluoromethyl group, and T represents any substituents indicated in Table 1 to Table 6 (hereinafter, referred to as Compound Class SX22).

a compound (L-3) wherein $Z^1$ and $Z^2$ each represents a nitrogen atom, and $R^{3b}$ represents a hydrogen atom, and T represents any substituents indicated in Table 1 to Table 6 (hereinafter, referred to as Compound Class SX23).

a compound (L-3) wherein $Z^1$ and $Z^2$ each represents a nitrogen atom, and $R^{3b}$ represents a trifluoromethyl group, and T represents any substituents indicated in Table 1 to Table 6 (hereinafter, referred to as Compound Class SX24).

a compound represented by formula (L-4):

(L-4)

wherein $Z^1$ and $Z^2$ each represents CH, and $R^{3/c}$ represents a hydrogen atom, and T represents any substituents indicated in Table 1 to Table 6 (hereinafter, referred to as Compound Class SX25).

a compound (L-4) wherein $Z^1$ and $Z^2$ each represents CH, and $R^{3b}$ represents a trifluoromethyl group, and T represents any substituents indicated in Table 1 to Table 6 (hereinafter, referred to as Compound Class SX26).

a compound (L-4) wherein $Z^1$ represents CH, $Z^2$ represents a nitrogen atom, and $R^{Jb}$ represents a hydrogen atom, and T represents any substituents indicated in Table 1 to Table 6 (hereinafter, referred to as Compound Class SX27).

a compound (L-4) wherein $Z^1$ represents CH, $Z^2$ represents a nitrogen atom, and $R^{3b}$ represents a trifluoromethyl group, and T represents any substituents indicated in Table 1 to Table 6 (hereinafter, referred to as Compound Class SX28).

a compound (L-4) wherein $Z^1$ represents a nitrogen atom, $Z^2$ represents CH, and $R^{3b}$ represents a hydrogen atom, and T represents any substituents indicated in Table 1 to Table 6 (hereinafter, referred to as Compound Class SX29).

a compound (L-4) wherein $Z^1$ represents a nitrogen atom, $Z^2$ represents CH, and $R^{3b}$ represents a trifluoromethyl group, and T represents any substituents indicated in Table 1 to Table 6 (hereinafter, referred to as Compound Class SX30).

a compound (L-4) wherein $Z^1$ and $Z^2$ each represents a nitrogen atom, and $R^{3b}$ represents a hydrogen atom, and T represents any substituents indicated in Table 1 to Table 6 (hereinafter, referred to as Compound Class SX31).

a compound (L-4) wherein $Z^1$ and $Z^2$ each represents a nitrogen atom, and $R^{3b}$ represents a trifluoromethyl group, and T represents any substituents indicated in Table 1 to Table 6 (hereinafter, referred to as Compound Class SX32).

a compound represented by formula (L-5):

(L-5)

wherein $Z^4$ and $Z$ each represents $CH_2$ and $R^{3b}$ represents a hydrogen atom, and T represents any substituents indicated in Table 1 to Table 6 (hereinafter, referred to as Compound Class SX33).

a compound (L-5) wherein $Z^4$ and $Z^5$ each represents $CH_2$, and $R^{3b}$ represents a trifluoromethyl group, and T represents any substituents indicated in Table 1 to Table 6 (hereinafter, referred to as Compound Class SX34).

a compound (L-5) wherein $Z^4$ represents $CH_2$, $Z^5$ represents C(O), and $R^{3b}$ represents a hydrogen atom, and T represents any substituents indicated in Table 1 to Table 6 (hereinafter, referred to as Compound Class SX35).

a compound (L-5) wherein $Z^4$ represents $CH_2$, $Z^5$ represents C(O), and $R^{3b}$ represents a trifluoromethyl group, and T represents any substituents indicated in Table 1 to Table 6 (hereinafter, referred to as Compound Class SX36).

a compound (L-5) wherein $Z^4$ represents C(O), $Z^5$ represents $CH_2$, and $R^{3b}$ represents a hydrogen atom, and T represents any substituents indicated in Table 1 to Table 6 (hereinafter, referred to as Compound Class SX37).

a compound (L-5) wherein $Z^4$ represents C(O), $Z^5$ represents $CH_2$, and $R^{3b}$ represents a trifluoromethyl group, and T represents any substituents indicated in Table 1 to Table 6 (hereinafter, referred to as Compound Class SX38).

a compound (L-5) wherein $Z^4$ represents NH, $Z^5$ represents C(O), and $R^{3b}$ represents a hydrogen atom, and T represents any substituents indicated in Table 1 to Table 6 (hereinafter, referred to as Compound Class SX39).

a compound (L-5) wherein $Z^4$ represents NH, $Z^5$ represents C(O), and $R^{3b}$ represents a trifluoromethyl group, and T represents any substituents indicated in Table 1 to Table 6 (hereinafter, referred to as Compound Class SX40).

a compound (L-5) wherein $Z^4$ represents C(O), $Z^5$ represents NH, and $R^{3b}$ represents a hydrogen atom, and T represents any substituents indicated in Table 1 to Table 6 (hereinafter, referred to as Compound Class SX41).

a compound (L-5) wherein $Z^4$ represents C(O), $Z^5$ represents NH, and $R^{3b}$ represents a trifluoromethyl group, and T represents any substituents indicated in Table 1 to Table 6 (hereinafter, referred to as Compound Class SX42).

a compound (L-5) wherein $Z^4$ represents NMe, $Z^5$ represents C(O), and $R^{sb}$ represents a hydrogen atom, and T represents any substituents indicated in Table 1 to Table 6 (hereinafter, referred to as Compound Class SX43).

a compound (L-5) wherein $Z^4$ represents NMe, $Z^5$ represents C(O), and $R^{3b}$ represents a trifluoromethyl group, and T represents any substituents indicated in Table 1 to Table 6 (hereinafter, referred to as Compound Class SX44).

a compound (L-5) wherein $Z^4$ represents C(O), $Z^5$ represents NMe, and $R^{3b}$ represents a hydrogen atom, and T represents any substituents indicated in Table 1 to Table 6 (hereinafter, referred to as Compound Class SX45).

a compound (L-5) wherein $Z^4$ represents C(O), $Z^5$ represents NMe, and $R^{3b}$ represents a trifluoromethyl group, and T represents any substituents indicated in Table 1 to Table 6 (hereinafter, referred to as Compound Class SX46).

a compound represented by formula (L-6):

$$\text{(L-6)}$$

wherein $Z^4$ and $Z^5$ each represents $CH_2$, and $R^{3b}$ represents a hydrogen atom, and T represents any substituents indicated in Table 1 to Table 6 (hereinafter, referred to as Compound Class SX47).

a compound (L-6) wherein wherein $Z^4$ and $Z^5$ each represents $CH_2$, and $R^{3b}$ represents a trifluoromethyl group, and T represents any substituents indicated in Table 1 to Table 6 (hereinafter, referred to as Compound Class SX48).

a compound (L-6) wherein $Z^4$ represents $CH_2$, $Z^5$ represents C(O), and $R^{3b}$ represents a hydrogen atom, and T represents any substituents indicated in Table 1 to Table 6 (hereinafter, referred to as Compound Class SX49).

a compound (L-6) wherein $Z^4$ represents $CH_2$, $Z^5$ represents C(O), and $R^{3b}$ represents a trifluoromethyl group, and T represents any substituents indicated in Table 1 to Table 6 (hereinafter, referred to as Compound Class SX50).

a compound (L-6) wherein $Z^4$ represents C(O), $Z^5$ represents $CH_2$, and $R^{3b}$ represents a hydrogen atom, and T represents any substituents indicated in Table 1 to Table 6 (hereinafter, referred to as Compound Class SX51).

a compound (L-6) wherein $Z^4$ represents C(O), $Z^5$ represents $CH_2$, and $R^{3b}$ represents a trifluoromethyl group, and T represents any substituents indicated in Table 1 to Table 6 (hereinafter, referred to as Compound Class SX52).

a compound (L-6) wherein $Z^4$ represents NH, $Z^5$ represents C(O), and $R^{3b}$ represents a hydrogen atom, and T represents any substituents indicated in Table 1 to Table 6 (hereinafter, referred to as Compound Class SX53).

a compound (L-6) wherein $Z^4$ represents NH, $Z^5$ represents C(O), and $R^{3b}$ represents a trifluoromethyl group, and T represents any substituents indicated in Table 1 to Table 6 (hereinafter, referred to as Compound Class SX54).

a compound (L-6) wherein $Z^4$ represents C(O), $Z^5$ represents NH, and $R^{3b}$ represents a hydrogen atom, and T represents any substituents indicated in Table 1 to Table 6 (hereinafter, referred to as Compound Class SX55).

a compound (L-6) wherein $Z^4$ represents C(O), $Z^5$ represents NH, and $R^{3b}$ represents a trifluoromethyl group, and T represents any substituents indicated in Table 1 to Table 6 (hereinafter, referred to as Compound Class SX56).

a compound (L-6) wherein $Z^4$ represents NMe, $Z^5$ represents C(O), and $R^{3b}$ represents a hydrogen atom, and T represents any substituents indicated in Table 1 to Table 6 (hereinafter, referred to as Compound Class SX57).

a compound (L-6) wherein $Z^4$ represents NMe, $Z^5$ represents C(O), and $R^{3b}$ represents a trifluoromethyl group, and T represents any substituents indicated in Table 1 to Table 6 (hereinafter, referred to as Compound Class SX58).

a compound (L-6) wherein $Z^4$ represents C(O), $Z^5$ represents NMe, and $R^{3b}$ represents a hydrogen atom, and T represents any substituents indicated in Table 1 to Table 6 (hereinafter, referred to as Compound Class SX59).

a compound (L-6) wherein $Z^4$ represents C(O), $Z^5$ represents NMe, and $R^{3b}$ represents a trifluoromethyl group, and T represents any substituents indicated in Table 1 to Table 6 (hereinafter, referred to as Compound Class SX60).

a compound represented by formula (L-7):

$$\text{(L-7)}$$

wherein $Z^4$ and $Z^5$ each represents $CH_2$ and $R^{3b}$ represents a hydrogen atom, and T represents any substituents indicated in Table 1 to Table 6 (hereinafter, referred to as Compound Class SX61).

a compound (L-7) wherein $Z^4$ and $Z^5$ each represents $CH_2$, and $R^{3b}$ represents a trifluoromethyl group, and T represents any substituents indicated in Table 1 to Table 6 (hereinafter, referred to as Compound Class SX62).

a compound (L-7) wherein $Z^4$ represents $CH_2$, $Z^5$ represents C(O), and $R^{3b}$ represents a hydrogen atom, and T represents any substituents indicated in Table 1 to Table 6 (hereinafter, referred to as Compound Class SX63).

a compound (L-7) wherein $Z^4$ represents $CH_2$, $Z^5$ represents C(O), and $R^{3b}$ represents a trifluoromethyl group, and T represents any substituents indicated in Table 1 to Table 6 (hereinafter, referred to as Compound Class SX64).

a compound (L-7) wherein $Z^4$ represents C(O), $Z^5$ represents $CH_2$, and $R^{3b}$ represents a hydrogen atom, and T represents any substituents indicated in Table 1 to Table 6 (hereinafter, referred to as Compound Class SX65).

a compound (L-7) wherein $Z^4$ represents C(O), $Z^5$ represents $CH_2$, and $R^{3b}$ represents a trifluoromethyl group, and T represents any substituents indicated in Table 1 to Table 6 (hereinafter, referred to as Compound Class SX66).

a compound (L-7) wherein $Z^4$ represents NH, $Z^5$ represents C(O), and $R^{3b}$ represents a hydrogen atom, and T represents any substituents indicated in Table 1 to Table 6 (hereinafter, referred to as Compound Class SX67).

a compound (L-7) wherein $Z^4$ represents NH, $Z^5$ represents C(O), and $R^{3b}$ represents a trifluoromethyl group, and T represents any substituents indicated in Table 1 to Table 6 (hereinafter, referred to as Compound Class SX68).

a compound (L-7) wherein $Z^4$ represents C(O), $Z^5$ represents NH, and $R^{3b}$ represents a hydrogen atom, and T represents any substituents indicated in Table 1 to Table 6 (hereinafter, referred to as Compound Class SX69).

a compound (L-7) wherein $Z^4$ represents C(O), $Z^5$ represents NH, and $R^{3b}$ represents a trifluoromethyl group, and T represents any substituents indicated in Table 1 to Table 6 (hereinafter, referred to as Compound Class SX70).

a compound (L-7) wherein $Z^4$ represents NMe, $Z^5$ represents C(O), and $R^{3b}$ represents a hydrogen atom, and T represents any substituents indicated in Table 1 to Table 6 (hereinafter, referred to as Compound Class SX71).

a compound (L-7) wherein $Z^4$ represents NMe, $Z^5$ represents C(O), and $R^{3b}$ represents a trifluoromethyl group, and T represents any substituents indicated in Table 1 to Table 6 (hereinafter, referred to as Compound Class SX72).

a compound (L-7) wherein $Z^4$ represents C(O), $Z^5$ represents NMe, and $R^{3b}$ represents a hydrogen atom, and T represents any substituents indicated in Table 1 to Table 6 (hereinafter, referred to as Compound Class SX73).

a compound (L-7) wherein $Z^4$ represents C(O), $Z^5$ represents NMe, and $R^{3b}$ represents a trifluoromethyl group, and T represents any substituents indicated in Table 1 to Table 6 (hereinafter, referred to as Compound Class SX74).

a compound represented by formula (L-8):

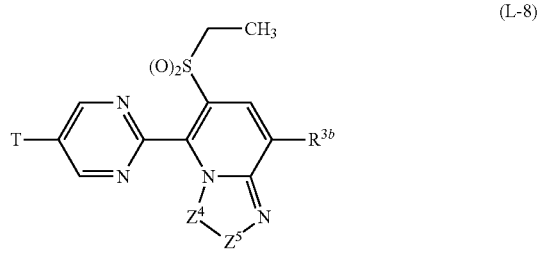

wherein $Z^4$ and $Z^5$ each represents $CH_2$, and $R^{3b}$ represents a hydrogen atom, and T represents any substituents indicated in Table 1 to Table 6 (hereinafter, referred to as Compound Class SX75).

a compound (L-8) wherein $Z^4$ and $Z^5$ each represents $CH_2$, and $R^{3b}$ represents a trifluoromethyl group, and T represents any substituents indicated in Table 1 to Table 6 (hereinafter, referred to as Compound Class SX76).

a compound (L-8) wherein $Z^4$ represents $CH_2$, $Z^5$ represents C(O), and $R^{3b}$ represents a hydrogen atom, and T represents any substituents indicated in Table 1 to Table 6 (hereinafter, referred to as Compound Class SX77).

a compound (L-8) wherein $Z^4$ represents $CH_2$, $Z^5$ represents C(O), and $R^{3b}$ represents a trifluoromethyl group, and T represents any substituents indicated in Table 1 to Table 6 (hereinafter, referred to as Compound Class SX78).

a compound (L-8) wherein $Z^4$ represents C(O), $Z^5$ represents $CH_2$, and $R^{3b}$ represents a hydrogen atom, and T represents any substituents indicated in Table 1 to Table 6 (hereinafter, referred to as Compound Class SX79).

a compound (L-8) wherein $Z^4$ represents C(O), $Z^5$ represents $CH_2$, and $R^{3b}$ represents a trifluoromethyl group, and T represents any substituents indicated in Table 1 to Table 6 (hereinafter, referred to as Compound Class SX80).

a compound (L-8) wherein $Z^4$ represents NH, $Z^5$ represents C(O), and $R^{3b}$ represents a hydrogen atom, and T represents any substituents indicated in Table 1 to Table 6 (hereinafter, referred to as Compound Class SX81).

a compound (L-8) wherein $Z^4$ represents NH, $Z^5$ represents C(O), and $R^{3b}$ represents a trifluoromethyl group, and T represents any substituents indicated in Table 1 to Table 6 (hereinafter, referred to as Compound Class SX82).

a compound (L-8) wherein $Z^4$ represents C(O), $Z^5$ represents NH, and $R^{3b}$ represents a hydrogen atom, and T represents any substituents indicated in Table 1 to Table 6 (hereinafter, referred to as Compound Class SX83).

a compound (L-8) wherein $Z^4$ represents C(O), $Z^5$ represents NH, and $R^{3b}$ represents a trifluoromethyl group, and T represents any substituents indicated in Table 1 to Table 6 (hereinafter, referred to as Compound Class SX84).

a compound (L-8) wherein $Z^4$ represents NMe, $Z^5$ represents C(O), and $R^{3b}$ represents a hydrogen atom, and T represents any substituents indicated in Table 1 to Table 6 (hereinafter, referred to as Compound Class SX85).

a compound (L-8) wherein $Z^4$ represents NMe, $Z^5$ represents C(O), and $R^{3b}$ represents a trifluoromethyl group, and T represents any substituents indicated in Table 1 to Table 6 (hereinafter, referred to as Compound Class SX86).

a compound (L-8) wherein $Z^4$ represents C(O), $Z^5$ represents NMe, and $R^{3b}$ represents a hydrogen atom, and T represents any substituents indicated in Table 1 to Table 6 (hereinafter, referred to as Compound Class SX87).

a compound (L-8) wherein $Z^4$ represents C(O), $Z^5$ represents NMe, and $R^{3b}$ represents a trifluoromethyl group, and T represents any substituents indicated in Table 1 to Table 6 (hereinafter, referred to as Compound Class SX88).

a compound represented by formula (L-9):

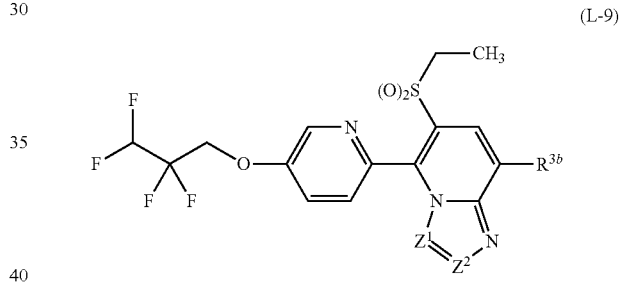

wherein $Z^4$ and $Z^5$ each represents CH, and $R^{3b}$ represents any substituents indicated in Table 7 to Table (hereinafter, referred to as Compound Class SX89).

TABLE 7

| |
|---|
| F |
| Cl |
| Br |
| Me |
| Et |
| Pr |
| i-Pr |
| c-Pr |
| 1-CN—c-Pr |
| 1-$CF_3$—c-Pr |
| c-Bu |
| O(c-Pr) |
| OMe |
| OEt |
| OPr |
| O(i-Pr) |
| $CF_3$ |
| $NH_2$ |
| $NHCH_2CF_3$ |
| CN |
| C(O)OEt |
| NHC(O)c-Pr |
| NMeC(O)c-Pr |

TABLE 8
Ph
2-F—Ph
3-F—Ph
4-F—Ph
2-Cl—Ph
3-Cl—Ph
4-Cl—Ph
3-CF$_3$—Ph
4-CF$_3$—Ph
3-NMe$_2$—Ph
4-NMe$_2$—Ph
3-CN—Ph
4-CN—Ph
4-C(O)NMe$_2$—Ph
4-NHC(O)Me—Ph
3,4-F$_2$—Ph
3,5-F$_2$—Ph
2,4-F$_2$—Ph
3,4,5-F$_3$—Ph
3,4-Cl$_2$—Ph
3,5-Cl$_2$—Ph
3,5-Cl$_2$-4-F—Ph
OPh
TABLE 9
Py2
4-F—Py2
5-F—Py2
4-Cl—Py2
5-Cl—Py2
4-CF$_3$—Py2
5-CF$_3$—Py2
3-Me—Py2
4-Me—Py2
5-Me—Py2
6-Me—Py2
5-CN—Py2
5-OCH$_2$CF$_2$CF$_3$—Py2
3,5-F$_2$—Py2
Py3
6-CF$_3$—Py3
5-CF$_3$—Py3
6-F—Py3
6-Cl—Py3
Py4
OPy2
OPy3
OPy4
TABLE 10
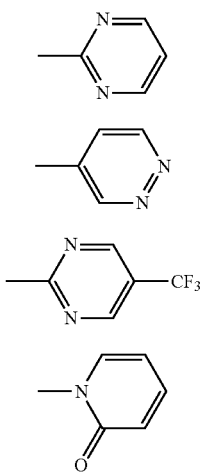
TABLE 10-continued
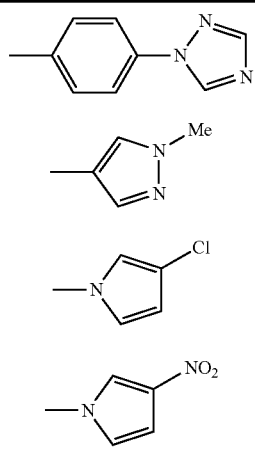
TABLE 11
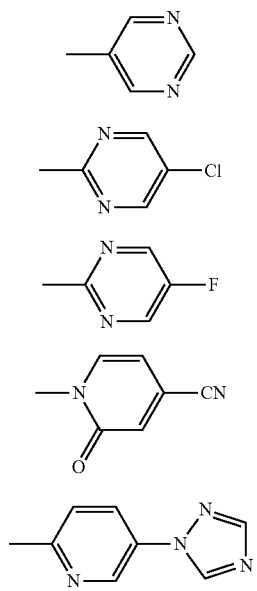
TABLE 12
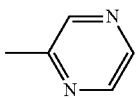

TABLE 12-continued
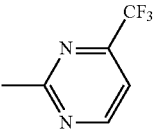
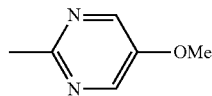
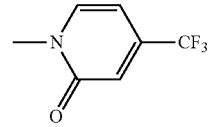
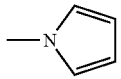
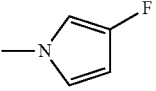
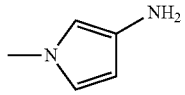
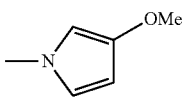
TABLE 13
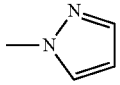
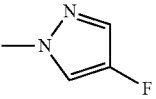
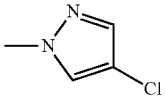
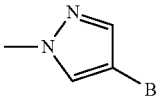
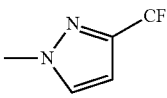
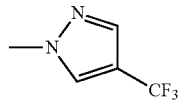
TABLE 13-continued
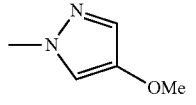
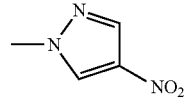
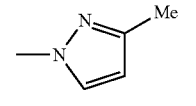
TABLE 14
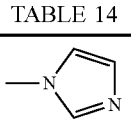
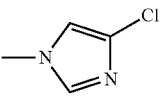
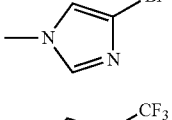
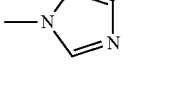
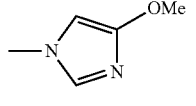
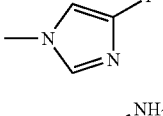
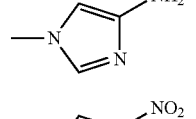
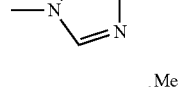
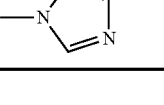
TABLE 15
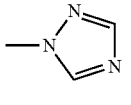

TABLE 15-continued

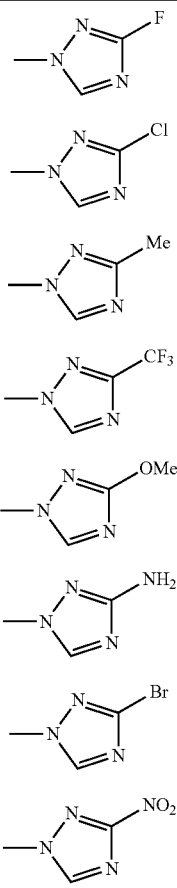

a compound represented by formula (L-9) wherein $Z^1$ represents CH, $Z^2$ represents a nitrogen atom, and $R^{3b}$ represents any substituents indicated in Table 7 to Table 15 (hereinafter, referred to as Compound Class SX90).

a compound represented by formula (L-9) wherein $Z^1$ represents a nitrogen atom, $Z^2$ represents CH, and $R^{3b}$ represents any substituents indicated in Table 7 to Table 15 (hereinafter, referred to as Compound Class SX91).

a compound represented by formula (L-9) wherein $Z^1$ and $Z^2$ each represents a nitrogen atom, and $R^{3b}$ represents any substituents indicated in Table 7 to Table 15 (hereinafter, referred to as Compound Class SX92).

a compound represented by formula (L-10):

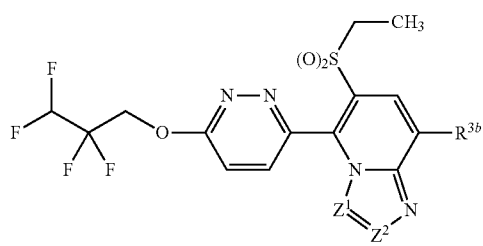

(L-10)

wherein $Z^1$ and $Z^2$ each represents CH, and $R^{3b}$ represents any substituents indicated in Table 7 to Table 15 (hereinafter, referred to as Compound Class SX93).

a compound represented by formula (L-10) wherein $Z^1$ represents CH, $Z^2$ represents a nitrogen atom, and $R^{3b}$ represents any substituents indicated in Table 7 to Table 15 (hereinafter, referred to as Compound Class SX94).

a compound represented by formula (L-10) wherein $Z^1$ represents a nitrogen atom, $Z^2$ represents CH, and $R^{3b}$ represents any substituents indicated in Table 7 to Table 15 (hereinafter, referred to as Compound Class SX95).

a compound represented by formula (L-10) wherein $Z^1$ and $Z^2$ each represents a nitrogen atom, and $R^{3b}$ represents any substituents indicated in Table 7 to Table 15 (hereinafter, referred to as Compound Class SX96).

a compound represented by formula (L-11):

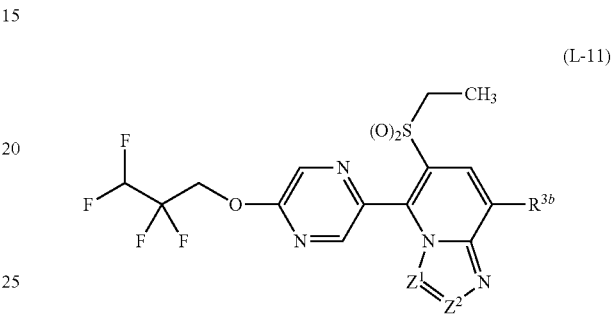

(L-11)

wherein $Z^1$ and $Z^2$ each represents CH, and $R^{3b}$ represents any substituents indicated in Table 7 to Table 15 (hereinafter, referred to as Compound Class SX97).

a compound represented by formula (L-11) wherein $Z^1$ represents CH, $Z^2$ represents a nitrogen atom, and $R^{3b}$ represents any substituents indicated in Table 7 to Table 15 (hereinafter, referred to as Compound Class SX98).

a compound represented by formula (L-11) wherein $Z^1$ represents a nitrogen atom, $Z^2$ represents CH, and $R^{3b}$ represents any substituents indicated in Table 7 to Table 15 (hereinafter, referred to as Compound Class SX99).

a compound represented by formula (L-11) wherein $Z^1$ represents a nitrogen atom, $Z^2$ represents a nitrogen atom, and $R^{3b}$ represents any substituents indicated in Table 7 to Table 15 (hereinafter, referred to as Compound Class SX100).

a compound represented by formula (L-12):

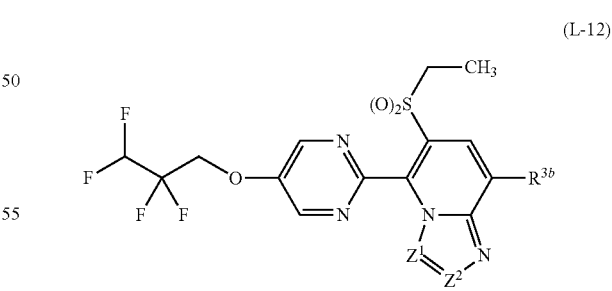

(L-12)

wherein $Z^1$ represents CH, $Z^2$ represents a nitrogen atom, and $R^{3b}$ represents any substituents indicated in Table 7 to Table 15 (hereinafter, referred to as Compound Class SX102).

a compound represented by formula (L-12) wherein $Z^1$ represents a nitrogen atom, $Z^2$ represents CH, and $R^{3b}$ represents any substituents indicated in Table 7 to Table 15 (hereinafter, referred to as Compound Class SX103).

a compound represented by formula (L-12) wherein $Z^1$ and $Z^2$ each represents a nitrogen atom, and $R^{3b}$ represents any substituents indicated in Table 7 to Table 15 (hereinafter, referred to as Compound Class SX104).

a compound represented by formula (L-13):

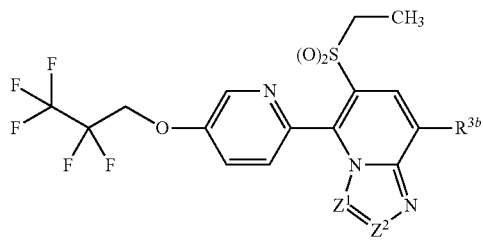

(L-13)

wherein $Z^1$ and $Z^2$ each represents CH, and $R^{3/c}$ represents any substituents indicated in Table 1 to Table 15 (hereinafter, referred to as Compound Class SX105).

a compound represented by formula (L-13) wherein $Z^1$ represents CH, $Z^2$ represents a nitrogen atom, and $R^{3b}$ represents any substituents indicated in Table 7 to Table 15 (hereinafter, referred to as Compound Class SX106).

a compound represented by formula (L-13) wherein $Z^1$ represents a nitrogen atom, $Z^2$ represents CH, and $R^{3b}$ represents any substituents indicated in Table 7 to Table 15 (hereinafter, referred to as Compound Class SX107).

a compound represented by formula (L-13) wherein $Z^1$ and $Z^2$ each represents a nitrogen atom, and $R^{3b}$ represents any substituents indicated in Table 7 to Table 15 (hereinafter, referred to as Compound Class SX108).

a compound represented by formula (L-14):

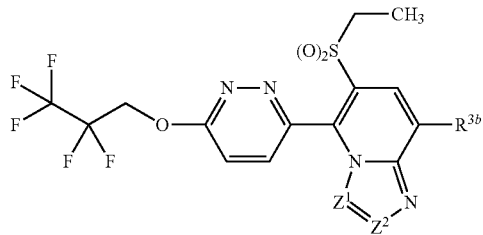

(L-14)

wherein $Z^1$ and $Z^2$ each represents CH, and $R^{3b}$ represents any substituents indicated in Table 7 to Table 15 (hereinafter, referred to as Compound Class SX109).

a compound represented by formula (L-14) wherein $Z^1$ represents CH, $Z^2$ represents a nitrogen atom, and $R^{3b}$ represents any substituents indicated in Table 7 to Table 15 (hereinafter, referred to as Compound Class SX110).

a compound represented by formula (L-14) wherein $Z^1$ represents a nitrogen atom, $Z^2$ represents CH, and $R^{3b}$ represents any substituents indicated in Table 7 to Table 15 (hereinafter, referred to as Compound Class SX111).

a compound represented by formula (L-14) wherein $Z^1$ and $Z^2$ each represents a nitrogen atom, and $R^{3b}$ represents any substituents indicated in Table 7 to Table 15 (hereinafter, referred to as Compound Class SX112).

a compound represented by formula (L-15):

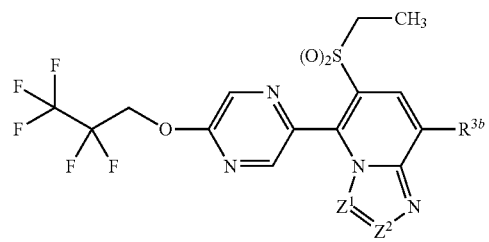

(L-15)

wherein $Z^1$ and $Z^2$ each represents CH, and $R^{3b}$ represents any substituents indicated in Table 7 to Table 15 (hereinafter, referred to as Compound Class SX113).

a compound represented by formula (L-15) wherein $Z^1$ represents CH, $Z^2$ represents a nitrogen atom, and $R^{3b}$ represents any substituents indicated in Table 7 to Table 15 (hereinafter, referred to as Compound Class SX114).

a compound represented by formula (L-15) wherein $Z^1$ represents a nitrogen atom, $Z^2$ represents CH, and $R^{3b}$ represents any substituents indicated in Table 7 to Table 15 (hereinafter, referred to as Compound Class SX115).

a compound represented by formula (L-15) wherein $Z^1$ and $Z^2$ each represents a nitrogen atom, and $R^{3b}$ represents any substituents indicated in Table 7 to Table 15 (hereinafter, referred to as Compound Class SX116).

a compound represented by formula (L-16):

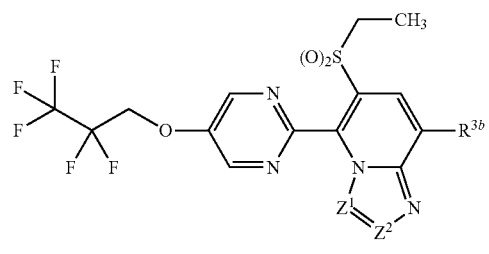

(L-16)

wherein $Z^1$ and $Z^2$ each represents CH, and $R^{3b}$ represents any substituents indicated in Table 7 to Table 15 (hereinafter, referred to as Compound Class SX117).

a compound represented by formula (L-16) wherein $Z^1$ represents CH, $Z^2$ represents a nitrogen atom, and $R^{3b}$ represents any substituents indicated in Table 7 to Table 15 (hereinafter, referred to as Compound Class SX118).

a compound represented by formula (L-16) wherein $Z^1$ represents a nitrogen atom, $Z^2$ represents CH, and $R^{3b}$ represents any substituents indicated in Table 7 to Table 15 (hereinafter, referred to as Compound Class SX119).

a compound represented by formula (L-16) wherein $Z^1$ and each represents a nitrogen atom, and $R^{3b}$ represents any substituents indicated in Table 7 to Table 15 (hereinafter, referred to as Compound Class SX120).

a compound represented by formula (L-17):

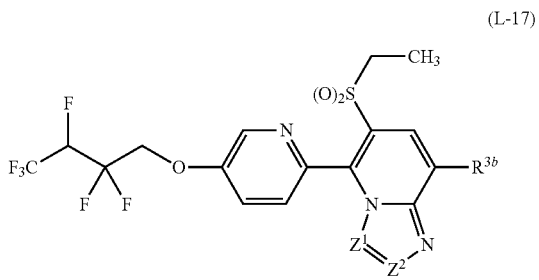

wherein $Z^1$ and $Z^2$ each represents CH, and $R^{3b}$ represents any substituents indicated in Table 7 to Table 15 (hereinafter, referred to as Compound Class SX121).

a compound represented by formula (L-17) wherein $Z^1$ represents CH, $Z^2$ represents a nitrogen atom, and $R^{3b}$ represents any substituents indicated in Table 7 to Table 15 (hereinafter, referred to as Compound Class SX122).

a compound represented by formula (L-17) wherein $Z^1$ represents a nitrogen atom, $Z^2$ represents CH and $R^{3b}$ represents any substituents indicated in Table 7 to Table 15 (hereinafter, referred to as Compound Class SX123).

a compound represented by formula (L-17) wherein $Z^1$ and $Z^2$ each represents a nitrogen atom, and $R^{3b}$ represents any substituents indicated in Table 7 to Table 15 (hereinafter, referred to as Compound Class SX124).

a compound represented by formula (L-18):

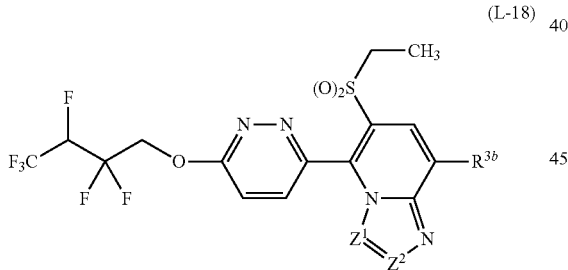

wherein $Z^1$ and $Z^2$ each represents CH, and $R^{3b}$ represents any substituents indicated in Table 7 to Table 15 (hereinafter, referred to as Compound Class SX125).

a compound represented by formula (L-18) wherein $Z^1$ represents CH, $Z^2$ represents a nitrogen atom and $R^{3b}$ represents any substituents indicated in Table 7 to Table 15 (hereinafter, referred to as Compound Class SX126).

a compound represented by formula (L-18) wherein $Z^1$ represents a nitrogen atom, $Z^2$ represents CH and $R^{3b}$ represents any substituents indicated in Table 7 to Table 15 (hereinafter, referred to as Compound Class SX127).

a compound represented by formula (L-18) wherein $Z^1$ and $Z^2$ each represents a nitrogen atom, and $R^{3b}$ represents any substituents indicated in Table 7 to Table 15 (hereinafter, referred to as Compound Class SX128).

a compound represented by formula (L-19):

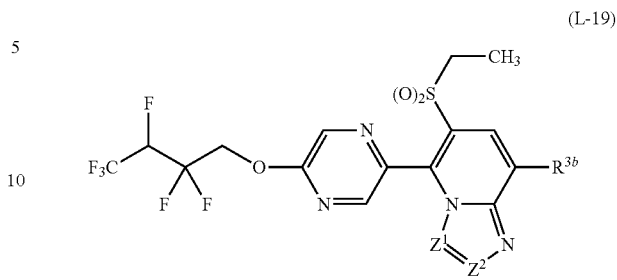

wherein $Z^1$ and $Z^2$ each represents CH, and $R^{3b}$ represents any substituents indicated in Table 7 to Table 15 (hereinafter, referred to as Compound Class SX129).

a compound represented by formula (L-19) wherein $Z^1$ represents CH, $Z^2$ represents a nitrogen atom and $R^{3b}$ represents any substituents indicated in Table 7 to Table 15 (hereinafter, referred to as Compound Class SX130).

a compound represented by formula (L-19) wherein $Z^1$ represents a nitrogen atom, $Z^2$ represents CH and $R^{3b}$ represents any substituents indicated in Table 7 to Table 15 (hereinafter, referred to as Compound Class SX131).

a compound represented by formula (L-19) wherein $Z^1$ and $Z^2$ each represents a nitrogen atom, and $R^{3b}$ represents any substituents indicated in Table 7 to Table 15 (hereinafter, referred to as Compound Class SX132).

a compound represented by formula (L-20):

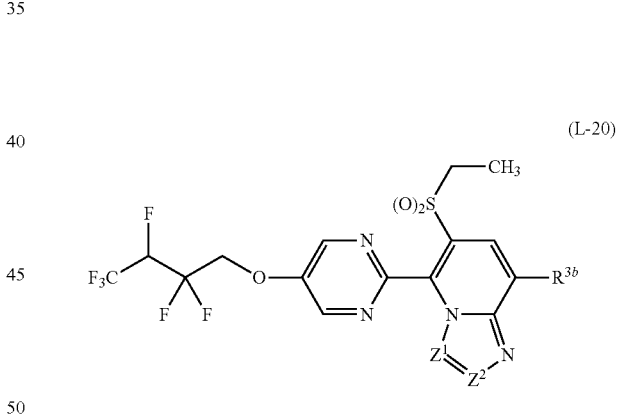

wherein $Z^1$ and $Z^2$ each represents CH, and $R^{3b}$ represents any substituents indicated in Table 7 to Table 15 (hereinafter, referred to as Compound Class SX133).

a compound represented by formula (L-20) wherein $Z^1$ represents CH, $Z^2$ represents a nitrogen atom, and $R^{3b}$ represents any substituents indicated in Table 7 to Table 15 (hereinafter, referred to as Compound Class SX134).

a compound represented by formula (L-20) wherein $Z^1$ represents a nitrogen atom, $Z^2$ represents CH, and $R^{3b}$ represents any substituents indicated in Table 7 to Table 15 (hereinafter, referred to as Compound Class SX135).

a compound represented by formula (L-20) wherein $Z^1$ and $Z^2$ each represents a nitrogen atom, and $R^{3b}$ represents any substituents indicated in Table 7 to Table 15 (hereinafter, referred to as Compound Class SX136).

a compound represented by formula (L-21):

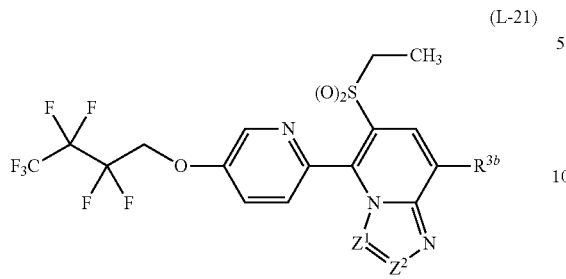

wherein $Z^1$ and $Z^2$ each represents CH, and $R^{3b}$ represents any substituents indicated in Table 7 to Table 15 (hereinafter, referred to as Compound Class SX137).

a compound represented by formula (L-21) wherein $Z^1$ represents CH, $Z^2$ represents a nitrogen atom, and $R^{3b}$ represents any substituents indicated in Table 7 to Table 15 (hereinafter, referred to as Compound Class SX138).

a compound represented by formula (L-21) wherein $Z^1$ represents a nitrogen atom, $Z^2$ represents CH, and $R^{3b}$ represents any substituents indicated in Table 7 to Table 15 (hereinafter, referred to as Compound Class SX139).

a compound represented by formula (L-21) wherein $Z^1$ and $Z^2$ each represents a nitrogen atom, and $R^{3b}$ represents any substituents indicated in Table 7 to Table 15 (hereinafter, referred to as Compound Class SX140).

a compound represented by formula (L-22):

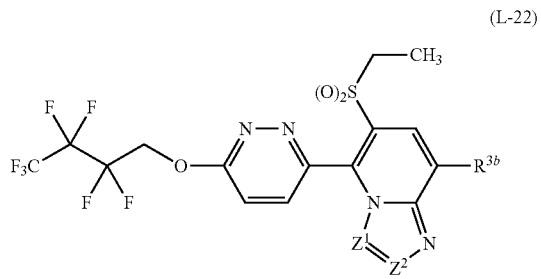

wherein $Z^1$ and $Z^2$ each represents CH, and $R^{3b}$ represents any substituents indicated in Table 7 to Table 15 (hereinafter, referred to as Compound Class SX141).

a compound represented by formula (L-22) wherein $Z^1$ represents CH, $Z^2$ represents a nitrogen atom, and $R^{3b}$ represents any substituents indicated in Table 7 to Table 15 (hereinafter, referred to as Compound Class SX142).

a compound represented by formula (L-22) wherein $Z^1$ represents a nitrogen atom, $Z^2$ represents CH, and $R^{3b}$ represents any substituents indicated in Table 7 to Table 15 (hereinafter, referred to as Compound Class SX143).

a compound represented by formula (L-22) wherein $Z^1$ and $Z^2$ each represents a nitrogen atom, and $R^{3b}$ represents any substituents indicated in Table 7 to Table 15 (hereinafter, referred to as Compound Class SX144).

a compound represented by formula (L-23):

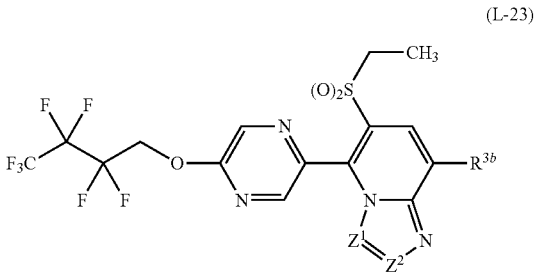

wherein $Z^1$ and $Z^2$ each represents CH, and $R^{3b}$ represents any substituents indicated in Table 7 to Table 15 (hereinafter, referred to as Compound Class SX145).

a compound represented by formula (L-23) wherein $Z^1$ represents CH, $Z^2$ represents a nitrogen atom, and $R^{3b}$ represents any substituents indicated in Table 7 to Table 15 (hereinafter, referred to as Compound Class SX146).

a compound represented by formula (L-23) wherein $Z^1$ represents a nitrogen atom, $Z^2$ represents CH, and $R^{3b}$ represents any substituents indicated in Table 7 to Table 15 (hereinafter, referred to as Compound Class SX147).

a compound represented by formula (L-23) wherein $Z^1$ and $Z^2$ each represents a nitrogen atom, and $R^{3b}$ represents any substituents indicated in Table 7 to Table 15 (hereinafter, referred to as Compound Class SX148).

a compound represented by formula (L-24):

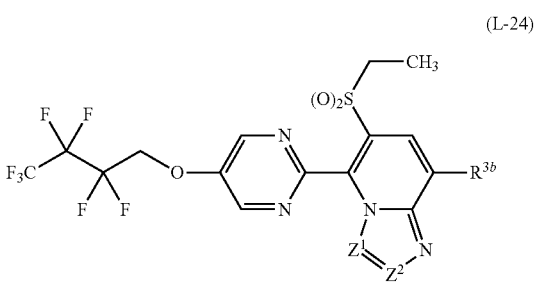

wherein $Z^1$ and $Z^2$ each represents CH, and $R^{3b}$ represents any substituents indicated in Table 7 to Table 15 (hereinafter, referred to as Compound Class SX149).

a compound represented by formula (L-24) wherein $Z^1$ represents CH, $Z^2$ represents a nitrogen atom, and $R^{3b}$ represents any substituents indicated in Table 7 to Table 15 (hereinafter, referred to as Compound Class SX150).

a compound represented by formula (L-24) wherein $Z^1$ represents a nitrogen atom, $Z^2$ represents CH, and $R^{3b}$ represents any substituents indicated in Table 7 to Table 15 (hereinafter, referred to as Compound Class SX151).

a compound represented by formula (L-24) wherein $Z^1$ and $Z^2$ each represents a nitrogen atom, and $R^{3b}$ represents any substituents indicated in Table 7 to Table 15 (hereinafter, referred to as Compound Class SX152).

a compound represented by formula (L-25):

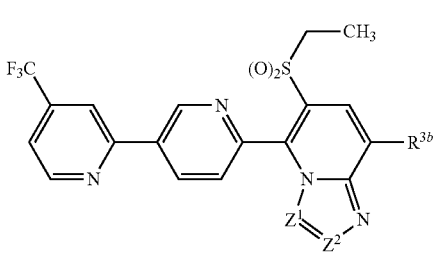

(L-25)

wherein $Z^1$ and $Z^2$ each represents CH, and $R^{3b}$ represents any substituents indicated in Table 7 to Table 15 (hereinafter, referred to as Compound Class SX153).

a compound represented by formula (L-25) wherein $Z^1$ represents CH, $Z^2$ represents a nitrogen atom, and $R^{3b}$ represents any substituents indicated in Table 7 to Table 15 (hereinafter, referred to as Compound Class SX154).

a compound represented by formula (L-25) wherein $Z^1$ represents a nitrogen atom, $Z^2$ represents CH, and $R^{3b}$ represents any substituents indicated in Table 7 to Table 15 (hereinafter, referred to as Compound Class SX155).

a compound represented by formula (L-25) wherein $Z^1$ and $Z^2$ each represents a nitrogen atom, and $R^{3b}$ represents any substituents indicated in Table 7 to Table 15 (hereinafter, referred to as Compound Class SX156).

a compound represented by formula (L-26):

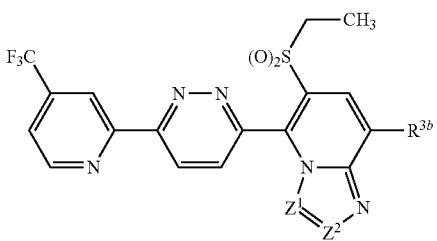

(L-26)

wherein $Z^1$ and $Z^2$ each represents CH, and $R^{3b}$ represents any substituents indicated in Table 7 to Table 15 (hereinafter, referred to as Compound Class SX157).

a compound represented by formula (L-26) wherein $Z^1$ represents CH, $Z^2$ represents a nitrogen atom, and $R^{3b}$ represents any substituents indicated in Table 7 to Table 15 (hereinafter, referred to as Compound Class SX158).

a compound represented by formula (L-26) wherein $Z^1$ represents a nitrogen atom, $Z^2$ represents CH, and $R^{3b}$ represents any substituents indicated in Table 7 to Table 15 (hereinafter, referred to as Compound Class SX159).

a compound represented by formula (L-26) wherein $Z^1$ and $Z^2$ each represents a nitrogen atom, and $R^{3b}$ represents any substituents indicated in Table 7 to Table 15 (hereinafter, referred to as Compound Class SX160).

a compound represented by formula (L-27):

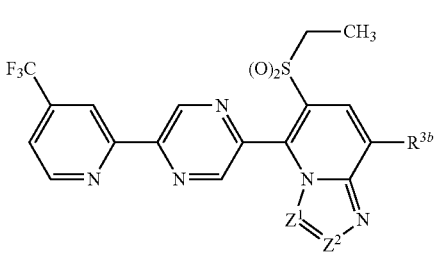

(L-27)

wherein $Z^1$ and $Z^2$ each represents CH, and $R^{3b}$ represents any substituents indicated in Table 7 to Table 15 (hereinafter, referred to as Compound Class SX161).

a compound represented by formula (L-27) wherein $Z^1$ represents CH, $Z^2$ represents a nitrogen atom, and $R^{3b}$ represents any substituents indicated in Table 7 to Table 15 (hereinafter, referred to as Compound Class SX162).

a compound represented by formula (L-27) wherein $Z^1$ represents a nitrogen atom, $Z^2$ represents CH, and $R^{3b}$ represents any substituents indicated in Table 7 to Table 15 (hereinafter, referred to as Compound Class SX163).

a compound represented by formula (L-27) wherein $Z^1$ and $Z^2$ each represents a nitrogen atom, and $R^{3b}$ represents any substituents indicated in Table 7 to Table 15 (hereinafter, referred to as Compound Class SX164).

a compound represented by formula (L-28):

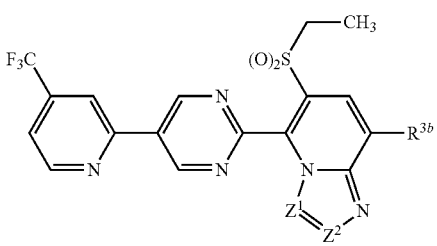

(L-28)

wherein $Z^1$ and $Z^2$ each represents CH, and $R^{3b}$ represents any substituents indicated in Table 7 to Table 15 (hereinafter, referred to as Compound Class SX165).

a compound represented by formula (L-28) wherein $Z^1$ represents CH, $Z^2$ represents a nitrogen atom, and $R^{3b}$ represents any substituents indicated in Table 7 to Table 15 (hereinafter, referred to as Compound Class SX166).

a compound represented by formula (L-28) wherein $Z^1$ represents a nitrogen atom, $Z^2$ represents CH, and $R^{3b}$ represents any substituents indicated in Table 7 to Table 15 (hereinafter, referred to as Compound Class SX167).

a compound represented by formula (L-28) wherein $Z^1$ and $Z^2$ each represents a nitrogen atom, and $R^{3b}$ represents any substituents indicated in Table 7 to Table 15 (hereinafter, referred to as Compound Class SX168).

a compound represented by formula (L-29):

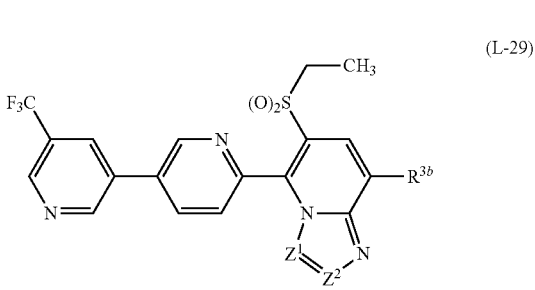

(L-29)

wherein $Z^1$ and $Z^2$ each represents CH, and $R^{3b}$ represents any substituents indicated in Table 7 to Table 15 (hereinafter, referred to as Compound Class SX16S).

a compound represented by formula (L-29) wherein $Z^1$ represents CH, $Z^2$ represents a nitrogen atom, and $R^{3b}$ represents any substituents indicated in Table 7 to Table 15 (hereinafter, referred to as Compound Class SX170).

a compound represented by formula (L-29) wherein $Z^1$ represents a nitrogen atom, $Z^2$ represents CH, and $R^{3b}$ represents any substituents indicated in Table 7 to Table 15 (hereinafter, referred to as Compound Class SX171).

a compound represented by formula (L-29) wherein $Z^1$ and $Z^2$ each represents a nitrogen atom, and $R^{3b}$ represents any substituents indicated in Table 7 to Table 15 (hereinafter, referred to as Compound Class SX172).

a compound represented by formula (L-30):

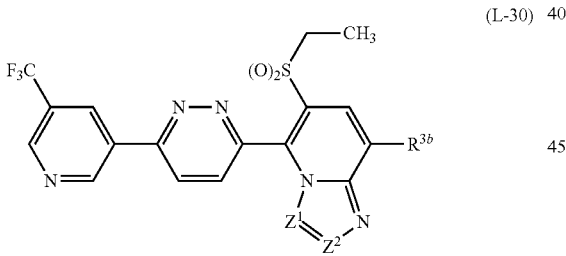

(L-30)

wherein $Z^1$ and $Z^2$ each represents CH, and $R^{3b}$ represents any substituents indicated in Table 7 to Table 15 (hereinafter, referred to as Compound Class SX173).

a compound represented by formula (L-30) wherein $Z^1$ represents CH, $Z^2$ represents a nitrogen atom, and $R^{3b}$ represents any substituents indicated in Table 7 to Table 15 (hereinafter, referred to as Compound Class SX174).

a compound represented by formula (L-30) wherein $Z^1$ represents a nitrogen atom, $Z^2$ represents CH, and $R^{3b}$ represents any substituents indicated in Table 7 to Table 15 (hereinafter, referred to as Compound Class SX175).

a compound represented by formula (L-30) wherein $Z^1$ and $Z^2$ each represents a nitrogen atom, and $R^{3b}$ represents any substituents indicated in Table 7 to Table 15 (hereinafter, referred to as Compound Class SX176).

a compound represented by formula (L-31):

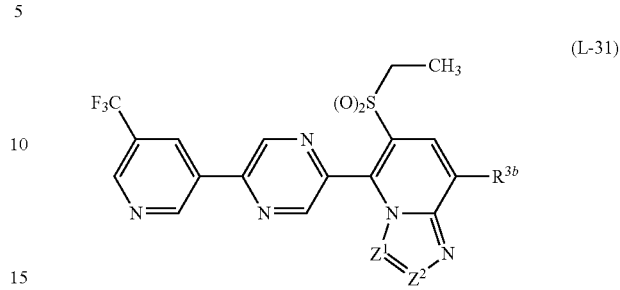

(L-31)

wherein $Z^1$ and $Z^2$ each represents CH, and $R^{3b}$ represents any substituents indicated in Table 7 to Table 15 (hereinafter, referred to as Compound Class SX177).

a compound represented by formula (L-31) wherein $Z^1$ represents CH, $Z^2$ represents a nitrogen atom, and $R^{3b}$ represents any substituents indicated in Table 7 to Table 15 (hereinafter, referred to as Compound Class SX178).

a compound represented by formula (L-31) wherein $Z^1$ represents a nitrogen atom, $Z^2$ represents CH, and $R^{3b}$ represents any substituents indicated in Table 7 to Table 15 (hereinafter, referred to as Compound Class SX179).

a compound represented by formula (L-31) wherein $Z^1$ and $Z^2$ each represents a nitrogen atom, and $R^{3b}$ represents any substituents indicated in Table 7 to Table 15 (hereinafter, referred to as Compound Class SX180).

a compound represented by formula (L-32):

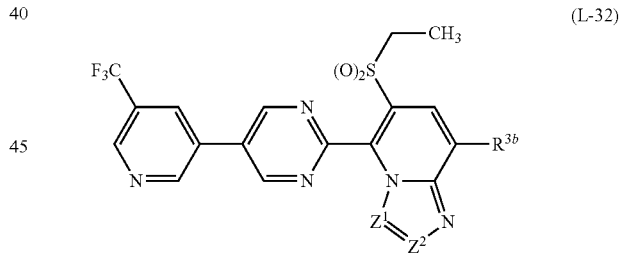

(L-32)

wherein $Z^1$ and $Z^2$ each represents CH, and $R^{3b}$ represents any substituents indicated in Table 7 to Table 15 (hereinafter, referred to as Compound Class SX181).

a compound represented by formula (L-32) wherein $Z^1$ represents CH, $Z^2$ represents a nitrogen atom, and $R^{3b}$ represents any substituents indicated in Table 7 to Table 15 (hereinafter, referred to as Compound Class SX182).

a compound represented by formula (L-32) wherein $Z^1$ represents a nitrogen atom, $Z^2$ represents CH, and $R^{3b}$ represents any substituents indicated in Table 7 to Table 15 (hereinafter, referred to as Compound Class SX183).

a compound represented by formula (L-32) wherein $Z^1$ and $Z^2$ each represents a nitrogen atom, and $R^{3b}$ represents any substituents indicated in Table 7 to Table 15 (hereinafter, referred to as Compound Class SX184).

a compound represented by formula (L-33):

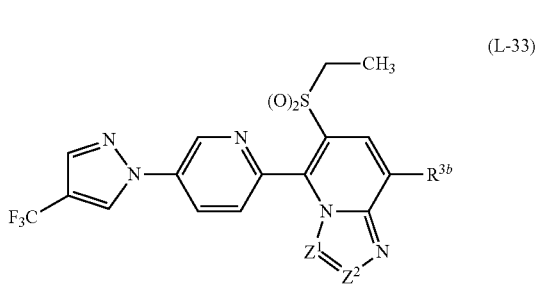

(L-33)

wherein $Z^1$ and $Z^2$ each represents CH, and $R^{3b}$ represents any substituents indicated in Table 7 to Table 15 (hereinafter, referred to as Compound Class SX185).

a compound represented by formula (L-33) wherein $Z^1$ represents CH, $Z^2$ represents a nitrogen atom, and $R^{3b}$ represents any substituents indicated in Table 7 to Table 15 (hereinafter, referred to as Compound Class SX186).

a compound represented by formula (L-33) wherein $Z^1$ represents a nitrogen atom, $Z^2$ represents CH, and $R^{3b}$ represents any substituents indicated in Table 7 to Table 15 (hereinafter, referred to as Compound Class SX187).

a compound represented by formula (L-33) wherein $Z^1$ and $Z^2$ each represents a nitrogen atom, and $R^{3b}$ represents any substituents indicated in Table 7 to Table 15 (hereinafter, referred to as Compound Class SX188).

a compound represented by formula (L-34):

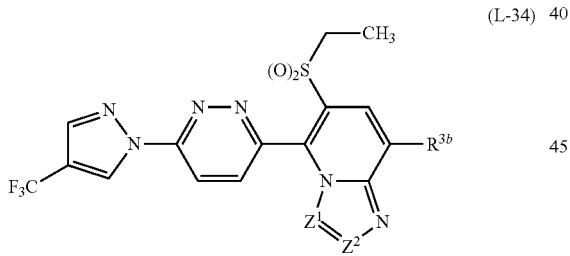

(L-34)

wherein $Z^1$ and $Z^2$ each represents CH, and $R^{3b}$ represents any substituents indicated in Table 7 to Table 15 (hereinafter, referred to as Compound Class SX189).

a compound represented by formula (L-34) wherein $Z^1$ represents CH, $Z^2$ represents a nitrogen atom, and $R^{3b}$ represents any substituents indicated in Table 7 to Table 15 (hereinafter, referred to as Compound Class SX190).

a compound represented by formula (L-34) wherein $Z^1$ represents a nitrogen atom, $Z^2$ represents CH, and $R^{3b}$ represents any substituents indicated in Table 7 to Table 15 (hereinafter, referred to as Compound Class SX191).

a compound represented by formula (L-34) wherein $Z^1$ and $Z^2$ each represents a nitrogen atom, and $R^{3b}$ represents any substituents indicated in Table 7 to Table 15 (hereinafter, referred to as Compound Class SX192).

a compound represented by formula (L-35):

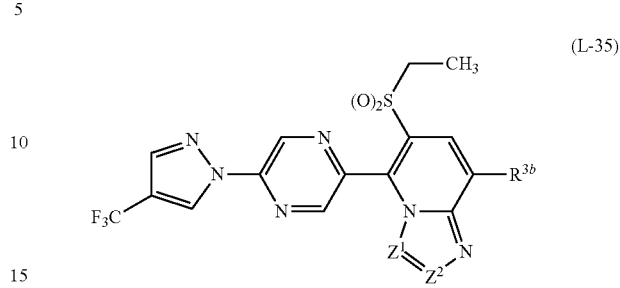

(L-35)

wherein $Z^1$ and $Z^2$ each represents CH, and $R^{3b}$ represents any substituents indicated in Table 7 to Table 15 (hereinafter, referred to as Compound Class SX193).

a compound represented by formula (L-35) wherein $Z^1$ represents CH, $Z^2$ represents a nitrogen atom, and $R^{3b}$ represents any substituents indicated in Table 7 to Table 15 (hereinafter, referred to as Compound Class SX194).

a compound represented by formula (L-35) wherein $Z^1$ represents a nitrogen atom, $Z^2$ represents CH, and $R^{3b}$ represents any substituents indicated in Table 7 to Table 15 (hereinafter, referred to as Compound Class SX195).

a compound represented by formula (L-35) wherein $Z^1$ and $Z^2$ each represents a nitrogen atom, and $R^{3b}$ represents any substituents indicated in Table 7 to Table 15 (hereinafter, referred to as Compound Class SX196).

a compound represented by formula (L-36):

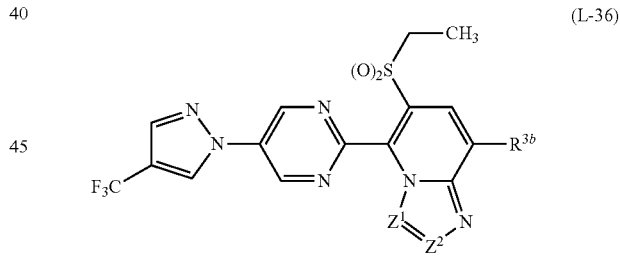

(L-36)

wherein $Z^1$ and $Z^2$ each represents CH, and $R^{3b}$ represents any substituents indicated in Table 7 to Table 15 (hereinafter, referred to as Compound Class SX197).

a compound represented by formula (L-36) wherein $Z^1$ represents CH, $Z^2$ represents a nitrogen atom, and $R^{3b}$ represents any substituents indicated in Table 7 to Table 15 (hereinafter, referred to as Compound Class SX198).

a compound represented by formula (L-36) wherein $Z^1$ represents a nitrogen atom, $Z^2$ represents CH, and $R^{3b}$ represents any substituents indicated in Table 7 to Table 15 (hereinafter, referred to as Compound Class SX199).

a compound represented by formula (L-36) wherein $Z^1$ and $Z^2$ each represents a nitrogen atom, and $R^{3b}$ represents any substituents indicated in Table 7 to Table 15 (hereinafter, referred to as Compound Class SX200).

a compound represented by formula (L-37):

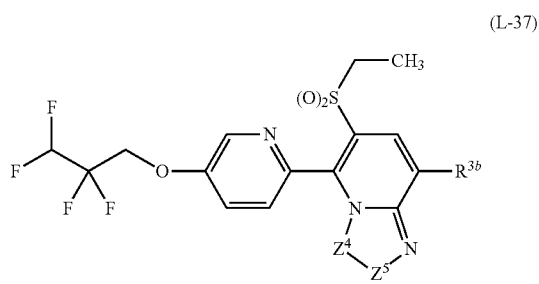

(L-37)

wherein $Z^4$ and Z each represents $CH_2$, and $R^{3b}$ represents any substituents indicated in Table 7 to Table 15 (hereinafter, referred to as Compound Class SX201).

a compound represented by formula (L-37) wherein $Z^4$ represents $CH_2$, $Z^5$ represents C(O), and $R^{3b}$ represents any substituents indicated in Table 7 to Table 15 (hereinafter, referred to as Compound Class SX202).

a compound represented by formula (L-37) wherein $Z^4$ represents C(O), $Z^5$ represents $CH_2$, and $R^{3b}$ represents any substituents indicated in Table 7 to Table 15 (hereinafter, referred to as Compound Class SX203).

a compound represented by formula (L-37) wherein $Z^4$ represents NH, $Z^5$ represents C(O), and $R^{3b}$ represents any substituents indicated in Table 7 to Table 15 (hereinafter, referred to as Compound Class SX204).

a compound represented by formula (L-37) wherein $Z^4$ represents C(O), $Z^5$ represents NH, and $R^{3b}$ represents any substituents indicated in Table 7 to Table 15 (hereinafter, referred to as Compound Class SX205).

a compound represented by formula (L-37) wherein $Z^4$ represents NMe, $Z^5$ represents C(O), and $R^{3b}$ represents any substituents indicated in Table 7 to Table 15 (hereinafter, referred to as Compound Class SX206).

a compound represented by formula (L-37) wherein $Z^4$ represents C(O), $Z^5$ represents NMe, and $R^{5b}$ represents any substituents indicated in Table 7 to Table 15 (hereinafter, referred to as Compound Class SX207).

a compound represented by formula (L-38):

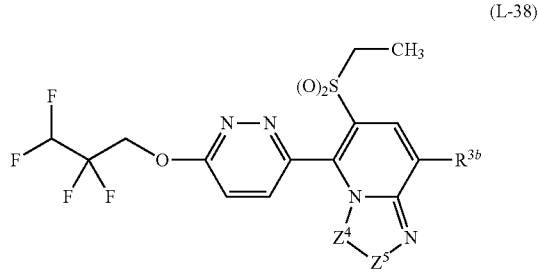

(L-38)

wherein $Z^4$ and Z each represents $CH_2$ and $R^{3b}$ represents any substituents indicated in Table 7 to Table 15 (hereinafter, referred to as Compound Class SX208).

a compound represented by formula (L-38) wherein $Z^4$ represents $CH_2$, $Z^5$ represents C(O), and $R^{3b}$ represents any substituents indicated in Table 7 to Table 15 (hereinafter, referred to as Compound Class SX209).

a compound represented by formula (L-38) wherein $Z^4$ represents C(O), $Z^5$ represents $CH_2$, and $R^{3b}$ represents any substituents indicated in Table 7 to Table 15 (hereinafter, referred to as Compound Class SX210).

a compound represented by formula (L-38) wherein $Z^4$ represents NH, $Z^5$ represents C(O), and $R^{3b}$ represents any substituents indicated in Table 7 to Table 15 (hereinafter, referred to as Compound Class SX211).

a compound represented by formula (L-38) wherein $Z^4$ represents C(O), $Z^5$ represents NH, and $R^{3b}$ represents any substituents indicated in Table 7 to Table 15 (hereinafter, referred to as Compound Class SX212).

a compound represented by formula (L-38) wherein $Z^4$ represents NMe, $Z^5$ represents C(O), and $R^{3b}$ represents any substituents indicated in Table 7 to Table 15 (hereinafter, referred to as Compound Class SX213).

a compound represented by formula (L-38) wherein $Z^4$ represents C(O), $Z^5$ represents NMe, and $R^{5b}$ represents any substituents indicated in Table 7 to Table 15 (hereinafter, referred to as Compound Class SX214).

a compound represented by formula (L-39):

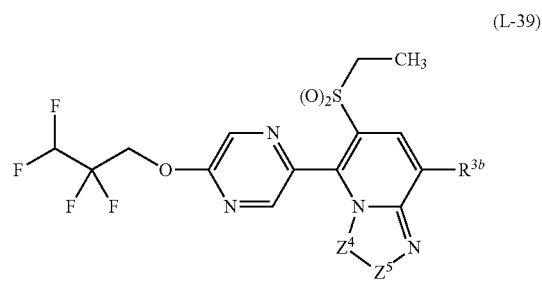

(L-39)

wherein $Z^4$ and $Z^5$ each represents $CH_2$, and $R^{3b}$ represents any substituents indicated in Table 7 to Table 15 (hereinafter, referred to as Compound Class SX215).

a compound represented by formula (L-39) wherein $Z^4$ represents $CH_2$, $Z^5$ represents C(O), and $R^{3b}$ represents any substituents indicated in Table 7 to Table 15 (hereinafter, referred to as Compound Class SX216).

a compound represented by formula (L-39) wherein $Z^4$ represents C(O), $Z^5$ represents $CH_2$, and $R^{3b}$ represents any substituents indicated in Table 7 to Table 15 (hereinafter, referred to as Compound Class SX217).

a compound represented by formula (L-39) wherein $Z^4$ represents NH, $Z^5$ represents C(O), and $R^{3b}$ represents any substituents indicated in Table 7 to Table 15 (hereinafter, referred to as Compound Class SX218).

a compound represented by formula (L-39) wherein $Z^4$ represents C(O), $Z^5$ represents NH, and $R^{3b}$ represents any substituents indicated in Table 7 to Table 15 (hereinafter, referred to as Compound Class SX219).

a compound represented by formula (L-39) wherein $Z^4$ represents NMe, $Z^5$ represents C(O), and $R^{3b}$ represents any substituents indicated in Table 7 to Table 15 (hereinafter, referred to as Compound Class SX220).

a compound represented by formula (L-39) wherein $Z^4$ represents C(O), $Z^5$ represents NMe, and $R^{3b}$ represents any substituents indicated in Table 7 to Table 15 (hereinafter, referred to as Compound Class SX221).

a compound represented by formula (L-40):

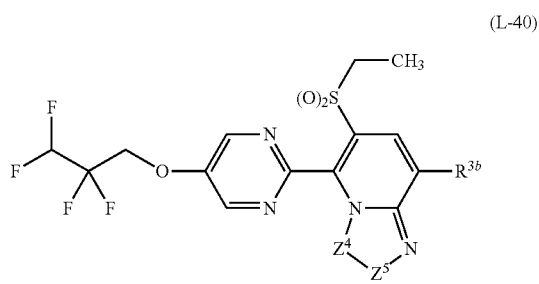

(L-40)

wherein $Z^4$ and $Z^5$ each represents $CH_2$, and $R^{3b}$ represents any substituents indicated in Table 7 to Table 15 (hereinafter, referred to as Compound Class SX222).

a compound represented by formula (L-40) wherein $Z^4$ represents $CH_2$, $Z^5$ represents C(O), and $R^{3b}$ represents any substituents indicated in Table 7 to Table 15 (hereinafter, referred to as Compound Class SX223).

a compound represented by formula (L-40) wherein $Z^4$ represents C(O), $Z^5$ represents $CH_2$, and $R^{3b}$ represents any substituents indicated in Table 7 to Table 15 (hereinafter, referred to as Compound Class SX224).

a compound represented by formula (L-40) wherein $Z^4$ represents NH, $Z^5$ represents C(O), and $R^{3b}$ represents any substituents indicated in Table 7 to Table 15 (hereinafter, referred to as Compound Class SX225).

a compound represented by formula (L-40) wherein $Z^4$ represents C(O), $Z^5$ represents NH, and $R^{3b}$ represents any substituents indicated in Table 7 to Table 15 (hereinafter, referred to as Compound Class SX226).

a compound represented by formula (L-40) wherein $Z^4$ represents NMe, $Z^5$ represents C(O), and $R^{3b}$ represents any substituents indicated in Table 7 to Table 15 (hereinafter, referred to as Compound Class SX227).

a compound represented by formula (L-40) wherein $Z^4$ represents C(O), $Z^5$ represents NMe, and $R^{3b}$ represents any substituents indicated in Table 7 to Table 15 (hereinafter, referred to as Compound Class SX228).

a compound represented by formula (L-41):

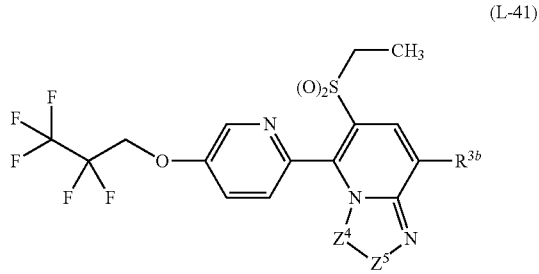

(L-41)

wherein $Z^4$ and $Z^5$ each represents $CH_2$, and $R^{3b}$ represents any substituents indicated in Table 7 to Table 15 (hereinafter, referred to as Compound Class SX229).

a compound represented by formula (L-41) wherein $Z^4$ represents $CH_2$, $Z^5$ represents C(O), and $R^{3b}$ represents any substituents indicated in Table 7 to Table 15 (hereinafter, referred to as Compound Class SX230).

a compound represented by formula (L-41) wherein $Z^4$ represents C(O), $Z^5$ represents $CH_2$, and $R^{3b}$ represents any substituents indicated in Table 7 to Table 15 (hereinafter, referred to as Compound Class SX231).

a compound represented by formula (L-41) wherein $Z^4$ represents NH, $Z^5$ represents C(O), and $R^{3b}$ represents any substituents indicated in Table 7 to Table 15 (hereinafter, referred to as Compound Class SX232).

a compound represented by formula (L-41) wherein $Z^4$ represents C(O), $Z^5$ represents NH, and $R^{3b}$ represents any substituents indicated in Table 7 to Table 15 (hereinafter, referred to as Compound Class SX233).

a compound represented by formula (L-41) wherein $Z^4$ represents NMe, $Z^5$ represents C(O), and $R^{3b}$ represents any substituents indicated in Table 7 to Table 15 (hereinafter, referred to as Compound Class SX234).

a compound represented by formula (L-41) wherein $Z^4$ represents C(O), $Z^5$ represents NMe, and $R^{5b}$ represents any substituents indicated in Table 7 to Table 15 (hereinafter, referred to as Compound Class SX235).

a compound represented by formula (L-42):

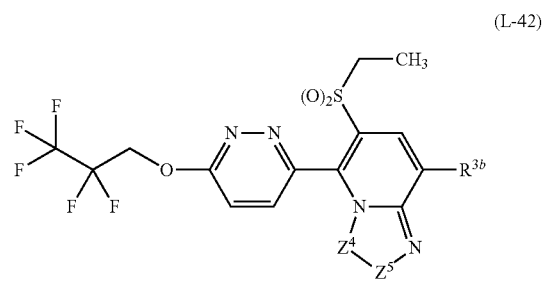

(L-42)

wherein $Z^4$ and $Z^5$ each represents $CH_2$, and $R^{3b}$ represents any substituents indicated in Table 7 to Table 15 (hereinafter, referred to as Compound Class SX236).

a compound represented by formula (L-42) wherein $Z^4$ represents $CH_2$, $Z^5$ represents C(O), and $R^{3b}$ represents any substituents indicated in Table 7 to Table 15 (hereinafter, referred to as Compound Class SX237).

a compound represented by formula (L-42) wherein $Z^4$ represents C(O), $Z^5$ represents $CH_2$, and $R^{3b}$ represents any substituents indicated in Table 7 to Table 15 (hereinafter, referred to as Compound Class SX238).

a compound represented by formula (L-42) wherein $Z^4$ represents NH, $Z^5$ represents C(O), and $R^{3b}$ represents any substituents indicated in Table 7 to Table 15 (hereinafter, referred to as Compound Class SX239).

a compound represented by formula (L-42) wherein $Z^4$ represents C(O), $Z^5$ represents NH, and $R^{3b}$ represents any substituents indicated in Table 7 to Table 15 (hereinafter, referred to as Compound Class SX240).

a compound represented by formula (L-42) wherein $Z^4$ represents NMe, $Z^5$ represents C(O), and $R^{3b}$ represents any substituents indicated in Table 7 to Table 15 (hereinafter, referred to as Compound Class SX241).

a compound represented by formula (L-42) wherein $Z^4$ represents C(O), $Z^5$ represents NMe, and $R^{3b}$ represents any substituents indicated in Table 7 to Table 15 (hereinafter, referred to as Compound Class SX242).

a compound represented by formula (L-43):

(L-43)

wherein $Z^4$ and $Z^5$ each represents $CH_2$, and $R^{3b}$ represents any substituents indicated in Table 7 to Table 15 (hereinafter, referred to as Compound Class SX243).

a compound represented by formula (L-43) wherein $Z^4$ represents $CH_2$, $Z^5$ represents C(O), and $R^{3b}$ represents any substituents indicated in Table 7 to Table 15 (hereinafter, referred to as Compound Class SX244).

a compound represented by formula (L-43) wherein $Z^4$ represents C(O), $Z^5$ represents $CH_2$, and $R^{3b}$ represents any substituents indicated in Table 7 to Table 15 (hereinafter, referred to as Compound Class SX245).

a compound represented by formula (L-43) wherein $Z^4$ represents NH, $Z^5$ represents C(O), and $R^{3b}$ represents any substituents indicated in Table 7 to Table 15 (hereinafter, referred to as Compound Class SX246).

a compound represented by formula (L-43) wherein $Z^4$ represents C(O), $Z^5$ represents NH, and $R^{3b}$ represents any substituents indicated in Table 7 to Table 15 (hereinafter, referred to as Compound Class SX247).

a compound represented by formula (L-43) wherein $Z^4$ represents NMe, $Z^5$ represents C(O), and $R^{3b}$ represents any substituents indicated in Table 7 to Table 15 (hereinafter, referred to as Compound Class SX248).

a compound represented by formula (L-43) wherein $Z^4$ represents C(O), $Z^5$ represents NMe, and $R^{3b}$ represents any substituents indicated in Table 7 to Table 15 (hereinafter, referred to as Compound Class SX249).

a compound represented by formula (L-44):

(L-44)

wherein $Z^4$ and $Z^5$ each represents $CH_2$, and $R^{3b}$ represents any substituents indicated in Table 7 to Table 15 (hereinafter, referred to as Compound Class SX250).

a compound represented by formula (L-44) wherein $Z^4$ represents $CH_2$, $Z^5$ represents C(O), and $R^{3b}$ represents any substituents indicated in Table 7 to Table 15 (hereinafter, referred to as Compound Class SX251).

a compound represented by formula (L-44) wherein $Z^4$ represents C(O), $Z^5$ represents $CH_2$, and $R^{3b}$ represents any substituents indicated in Table 7 to Table 15 (hereinafter, referred to as Compound Class SX252).

a compound represented by formula (L-44) wherein $Z^4$ represents NH, $Z^5$ represents C(O), and $R^{3b}$ represents any substituents indicated in Table 7 to Table 15 (hereinafter, referred to as Compound Class SX253).

a compound represented by formula (L-44) wherein $Z^4$ represents C(O), $Z^5$ represents NH, and $R^{3b}$ represents any substituents indicated in Table 7 to Table 15 (hereinafter, referred to as Compound Class SX254).

a compound represented by formula (L-44) wherein $Z^4$ represents NMe, $Z^5$ represents C(O), and $R^{3b}$ represents any substituents indicated in Table 7 to Table 15 (hereinafter, referred to as Compound Class SX255).

a compound represented by formula (L-44) wherein $Z^4$ represents C(O), $Z^5$ represents NMe, and $R^{5b}$ represents any substituents indicated in Table 7 to Table 15 (hereinafter, referred to as Compound Class SX256).

a compound represented by formula (L-45):

(L-45)

wherein $Z^4$ and $Z^5$ each represents $CH_2$, and $R^{3b}$ represents any substituents indicated in Table 7 to Table 15 (hereinafter, referred to as Compound Class SX257).

a compound represented by formula (L-45) wherein $Z^4$ represents $CH_2$, $Z^5$ represents C(O), and $R^{3b}$ represents any substituents indicated in Table 7 to Table 15 (hereinafter, referred to as Compound Class SX258).

a compound represented by formula (L-45) wherein $Z^4$ represents C(O), $Z^5$ represents $CH_2$, and $R^{3b}$ represents any substituents indicated in Table 7 to Table 15 (hereinafter, referred to as Compound Class SX259).

a compound represented by formula (L-45) wherein $Z^4$ represents NH, $Z^5$ represents C(O), and $R^{3b}$ represents any substituents indicated in Table 7 to Table 15 (hereinafter, referred to as Compound Class SX260).

a compound represented by formula (L-45) wherein $Z^4$ represents C(O), $Z^5$ represents NH, and $R^{3b}$ represents any substituents indicated in Table 7 to Table 15 (hereinafter, referred to as Compound Class SX261).

a compound represented by formula (L-45) wherein $Z^4$ represents NMe, $Z^5$ represents C(O), and $R^{3b}$ represents any substituents indicated in Table 7 to Table 15 (hereinafter, referred to as Compound Class SX262).

a compound represented by formula (L-45) wherein $Z^4$ represents C(O), $Z^5$ represents NMe, and $R^{3b}$ represents any substituents indicated in Table 7 to Table 15 (hereinafter, referred to as Compound Class SX263).

a compound represented by formula (L-46):

(L-46)

wherein $Z^4$ and $Z^5$ each represents $CH_2$, and $R^{3b}$ represents any substituents indicated in Table 7 to Table 15 (hereinafter, referred to as Compound Class SX264).

a compound represented by formula (L-46) wherein $Z^4$ represents $CH_2$, $Z^5$ represents C(O), and $R^{3b}$ represents any substituents indicated in Table 7 to Table 15 (hereinafter, referred to as Compound Class SX265).

a compound represented by formula (L-46) wherein $Z^4$ represents C(O), $Z^5$ represents $CH_2$, and $R^{3b}$ represents any substituents indicated in Table 7 to Table 15 (hereinafter, referred to as Compound Class SX266).

a compound represented by formula (L-46) wherein $Z^4$ represents NH, $Z^5$ represents C(O), and $R^{3b}$ represents any substituents indicated in Table 7 to Table 15 (hereinafter, referred to as Compound Class SX267).

a compound represented by formula (L-46) wherein $Z^4$ represents C(O), $Z^5$ represents NH, and $R^{3b}$ represents any substituents indicated in Table 7 to Table 15 (hereinafter, referred to as Compound Class SX268).

a compound represented by formula (L-46) wherein $Z^4$ represents NMe, $Z^5$ represents C(O), and $R^{3b}$ represents any substituents indicated in Table 7 to Table 15 (hereinafter, referred to as Compound Class SX269).

a compound represented by formula (L-46) wherein $Z^4$ represents C(O), $Z^5$ represents NMe, and $R^{3b}$ represents any substituents indicated in Table 7 to Table 15 (hereinafter, referred to as Compound Class SX270).

a compound represented by formula (L-47):

(L-47)

wherein $Z^4$ and $Z^5$ each represents $CH_2$, and $R^{3b}$ represents any substituents indicated in Table 7 to Table 15 (hereinafter, referred to as Compound Class SX271).

a compound represented by formula (L-47) wherein $Z^4$ represents $CH_2$, $Z^5$ represents C(O), and $R^{3b}$ represents any substituents indicated in Table 7 to Table 15 (hereinafter, referred to as Compound Class SX272).

a compound represented by formula (L-47) wherein $Z^4$ represents C(O), $Z^5$ represents $CH_2$, and $R^{3b}$ represents any substituents indicated in Table 7 to Table 15 (hereinafter, referred to as Compound Class SX273).

a compound represented by formula (L-47) wherein $Z^4$ represents NH, $Z^5$ represents C(O), and $R^{3b}$ represents any substituents indicated in Table 7 to Table 15 (hereinafter, referred to as Compound Class SX274).

a compound represented by formula (L-47) wherein $Z^4$ represents C(O), $Z^5$ represents NH, and $R^{3b}$ represents any substituents indicated in Table 7 to Table 15 (hereinafter, referred to as Compound Class SX275).

a compound represented by formula (L-47) wherein $Z^4$ represents NMe, $Z^5$ represents C(O), and $R^{3b}$ represents any referred to as Compound Class SX276).

a compound represented by formula (L-47) wherein $Z^4$ represents C(O), $Z^5$ represents NMe, and $R^{5b}$ represents any substituents indicated in Table 7 to Table 15 (hereinafter, referred to as Compound Class SX277).

a compound represented by formula (L-48):

(L-48)

wherein $Z^4$ and $Z^5$ each represents $CH_2$, and $R^{3b}$ represents any substituents indicated in Table 7 to Table 15 (hereinafter, referred to as Compound Class SX278).

a compound represented by formula (L-48) wherein $Z^4$ represents $CH_2$, $Z^5$ represents C(O), and $R^{3b}$ represents any substituents indicated in Table 7 to Table 15 (hereinafter, referred to as Compound Class SX279).

a compound represented by formula (L-48) wherein $Z^4$ represents C(O), $Z^5$ represents $CH_2$, and $R^{3b}$ represents any substituents indicated in Table 7 to Table 15 (hereinafter, referred to as Compound Class SX280).

a compound represented by formula (L-48) wherein $Z^4$ represents NH, $Z^5$ represents C(O), and $R^{3b}$ represents any substituents indicated in Table 7 to Table 15 (hereinafter, referred to as Compound Class SX281).

a compound represented by formula (L-48) wherein $Z^4$ represents C(O), $Z^5$ represents NH, and $R^{3b}$ represents any substituents indicated in Table 7 to Table 15 (hereinafter, referred to as Compound Class SX282).

a compound represented by formula (L-48) wherein $Z^4$ represents NMe, $Z^5$ represents C(O), and $R^{3b}$ represents any substituents indicated in Table 7 to Table 15 (hereinafter, referred to as Compound Class SX283).

a compound represented by formula (L-48) wherein $Z^4$ represents C(O), $Z^5$ represents NMe, and $R^{3b}$ represents any substituents indicated in Table 7 to Table 15 (hereinafter, referred to as Compound Class SX284).

a compound represented by formula (L-49):

(L-49)

wherein $Z^4$ and $Z^5$ each represents $CH_2$, and $R^{3b}$ represents any substituents indicated in Table 7 to Table 15 (hereinafter, referred to as Compound Class SX285).

a compound represented by formula (L-49) wherein $Z^4$ represents $CH_2$, $Z^5$ represents C(O), and $R^{3b}$ represents any substituents indicated in Table 7 to Table 15 (hereinafter, referred to as Compound Class SX286).

a compound represented by formula (L-49) wherein $Z^4$ represents C(O), $Z^5$ represents $CH_2$, and $R^{3b}$ represents any substituents indicated in Table 7 to Table 15 (hereinafter, referred to as Compound Class SX287).

a compound represented by formula (L-49) wherein $Z^4$ represents NH, $Z^5$ represents C(O), and $R^{3b}$ represents any substituents indicated in Table 7 to Table 15 (hereinafter, referred to as Compound Class SX288).

a compound represented by formula (L-49) wherein $Z^4$ represents C(O), $Z^5$ represents NH, and $R^{3b}$ represents any substituents indicated in Table 7 to Table 15 (hereinafter, referred to as Compound Class SX289).

a compound represented by formula (L-49) wherein $Z^4$ represents NMe, $Z^5$ represents C(O), and $R^{3b}$ represents any substituents indicated in Table 7 to Table 15 (hereinafter, referred to as Compound Class SX290).

a compound represented by formula (L-49) wherein $Z^4$ represents C(O), $Z^5$ represents NMe, and $R^{3b}$ represents any substituents indicated in Table 7 to Table 15 (hereinafter, referred to as Compound Class SX291).

a compound represented by formula (L-50):

(L-50)

wherein $Z^4$ and $Z^5$ each represents $CH_2$, and $R^{3b}$ represents any substituents indicated in Table 7 to Table 15 (hereinafter, referred to as Compound Class SX292).

a compound represented by formula (L-50) wherein $Z^4$ represents $CH_2$, $Z^5$ represents C(O), and $R^{3b}$ represents any substituents indicated in Table 7 to Table 15 (hereinafter, referred to as Compound Class SX293).

a compound represented by formula (L-50) wherein $Z^4$ represents C(O), $Z^5$ represents $CH_2$, and $R^{3b}$ represents any substituents indicated in Table 7 to Table 15 (hereinafter, referred to as Compound Class SX294).

a compound represented by formula (L-50) wherein $Z^4$ represents NH, $Z^5$ represents C(O), and $R^{3b}$ represents any substituents indicated in Table 7 to Table 15 (hereinafter, referred to as Compound Class SX295).

a compound represented by formula (L-50) wherein $Z^4$ represents C(O), $Z^5$ represents NH, and $R^{3b}$ represents any substituents indicated in Table 7 to Table 15 (hereinafter, referred to as Compound Class SX296).

a compound represented by formula (L-50) wherein $Z^4$ represents NMe, $Z^5$ represents C(O), and $R^{3b}$ represents any substituents indicated in Table 7 to Table 15 (hereinafter, referred to as Compound Class SX297).

a compound represented by formula (L-50) wherein $Z^4$ represents C(O), $Z^5$ represents NMe, and $R^{5b}$ represents any substituents indicated in Table 7 to Table 15 (hereinafter, referred to as Compound Class SX298).

a compound represented by formula (L-51):

(L-51)

wherein $Z^4$ and $Z^5$ each represents $CH_2$, and $R^{3b}$ represents any substituents indicated in Table 7 to Table 15 (hereinafter, referred to as Compound Class SX299).

a compound represented by formula (L-51) wherein $Z^4$ represents $CH_2$, $Z^5$ represents C(O), and $R^{3b}$ represents any substituents indicated in Table 7 to Table 15 (hereinafter, referred to as Compound Class SX300).

a compound represented by formula (L-51) wherein $Z^4$ represents C(O), $Z^5$ represents $CH_2$, and $R^{3b}$ represents any substituents indicated in Table 7 to Table 15 (hereinafter, referred to as Compound Class SX301).

a compound represented by formula (L-51) wherein $Z^4$ represents NH, $Z^5$ represents C(O), and $R^{3b}$ represents any substituents indicated in Table 7 to Table 15 (hereinafter, referred to as Compound Class SX302).

a compound represented by formula (L-51) wherein $Z^4$ represents C(O), $Z^5$ represents NH, and $R^{3b}$ represents any substituents indicated in Table 7 to Table 15 (hereinafter, referred to as Compound Class SX303).

a compound represented by formula (L-51) wherein $Z^4$ represents NMe, $Z^5$ represents C(O), and $R^{3b}$ represents any substituents indicated in Table 7 to Table 15 (hereinafter, referred to as Compound Class SX304).

a compound represented by formula (L-51) wherein $Z^4$ represents C(O), $Z^5$ represents NMe, and $R^{3b}$ represents any substituents indicated in Table 7 to Table 15 (hereinafter, referred to as Compound Class SX305).

a compound represented by formula (L-52):

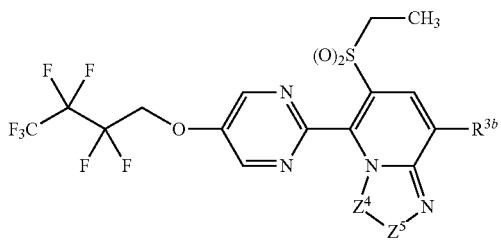

wherein $Z^4$ and $Z^5$ each represents $CH_2$, and $R^{3b}$ represents any substituents indicated in Table 7 to Table 15 (hereinafter, referred to as Compound Class SX306).

a compound represented by formula (L-52) wherein $Z^4$ represents $CH_2$, $Z^5$ represents C(O), and $R^{3b}$ represents any substituents indicated in Table 7 to Table 15 (hereinafter, referred to as Compound Class SX307).

a compound represented by formula (L-52) wherein $Z^4$ represents C(O), $Z^5$ represents $CH_2$, and $R^{3b}$ represents any substituents indicated in Table 7 to Table 15 (hereinafter, referred to as Compound Class SX308).

a compound represented by formula (L-51) wherein $Z^4$ represents NH, $Z^5$ represents C(O), and $R^{3b}$ represents any substituents indicated in Table 7 to Table 15 (hereinafter, referred to as Compound Class SX309).

a compound represented by formula (L-51) wherein $Z^4$ represents C(O), $Z^5$ represents NH, and $R^{3b}$ represents any substituents indicated in Table 7 to Table 15 (hereinafter, referred to as Compound Class SX310).

a compound represented by formula (L-52) wherein $Z^4$ represents NMe, $Z^5$ represents C(O), and $R^{3b}$ represents any substituents indicated in Table 7 to Table 15 (hereinafter, referred to as Compound Class SX311).

a compound represented by formula (L-52) wherein $Z^4$ represents C(O), $Z^5$ represents NMe, and $R^{3b}$ represents any substituents indicated in Table 7 to Table 15 (hereinafter, referred to as Compound Class SX312).

a compound represented by formula (L-53):

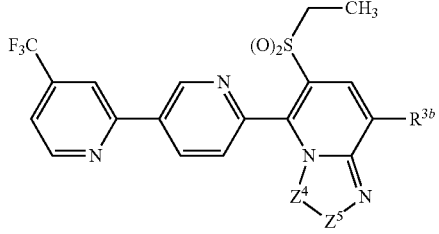

wherein $Z^4$ and $Z^5$ each represents $CH_2$, and $R^{3b}$ represents any substituents indicated in Table 7 to Table 15 (hereinafter, referred to as Compound Class SX313).

a compound represented by formula (L-53) wherein $Z^4$ represents $CH_2$, $Z^5$ represents C(O), and $R^{3b}$ represents any substituents indicated in Table 7 to Table 15 (hereinafter, referred to as Compound Class SX314).

a compound represented by formula (L-53) wherein $Z^4$ represents C(O), $Z^5$ represents $CH_2$, and $R^{3b}$ represents any substituents indicated in Table 7 to Table 15 (hereinafter, referred to as Compound Class SX315).

a compound represented by formula (L-53) wherein $Z^4$ represents NH, $Z^5$ represents C(O), and $R^{3b}$ represents any substituents indicated in Table 7 to Table 15 (hereinafter, referred to as Compound Class SX316).

a compound represented by formula (L-53) wherein $Z^4$ represents C(O), $Z^5$ represents NH, and $R^{3b}$ represents any substituents indicated in Table 7 to Table 15 (hereinafter, referred to as Compound Class SX317).

a compound represented by formula (L-53) wherein $Z^4$ represents NMe, $Z^5$ represents C(O), and $R^{3b}$ represents any substituents indicated in Table 7 to Table 15 (hereinafter, referred to as Compound Class SX318).

a compound represented by formula (L-53) wherein $Z^4$ represents C(O), $Z^5$ represents NMe, and $R^{5b}$ represents any substituents indicated in Table 7 to Table 15 (hereinafter, referred to as Compound Class SX319).

a compound represented by formula (L-54):

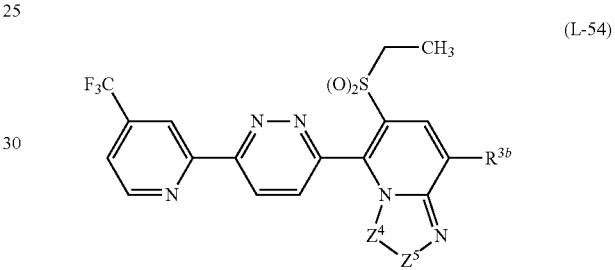

wherein $Z^4$ and $Z^5$ each represents $CH_2$, and $R^{3b}$ represents any substituents indicated in Table 7 to Table 15 (hereinafter, referred to as Compound Class SX320).

a compound represented by formula (L-54) wherein $Z^4$ represents $CH_2$, $Z^5$ represents C(O), and $R^{3b}$ represents any substituents indicated in Table 7 to Table 15 (hereinafter, referred to as Compound Class SX321).

a compound represented by formula (L-54) wherein $Z^4$ represents C(O), $Z^5$ represents $CH_2$, and $R^{3b}$ represents any substituents indicated in Table 7 to Table 15 (hereinafter, referred to as Compound Class SX322).

a compound represented by formula (L-54) wherein $Z^4$ represents NH, $Z^5$ represents C(O), and $R^{3b}$ represents any substituents indicated in Table 7 to Table 15 (hereinafter, referred to as Compound Class SX323).

a compound represented by formula (L-54) wherein $Z^4$ represents C(O), $Z^5$ represents NH, and $R^{3b}$ represents any substituents indicated in Table 7 to Table 15 (hereinafter, referred to as Compound Class SX324).

a compound represented by formula (L-54) wherein $Z^4$ represents NMe, $Z^5$ represents C(O), and $R^{3b}$ represents any substituents indicated in Table 7 to Table 15 (hereinafter, referred to as Compound Class SX325).

a compound represented by formula (L-54) wherein $Z^4$ represents C(O), $Z^5$ represents NMe, and $R^{3b}$ represents any substituents indicated in Table 7 to Table 15 (hereinafter, referred to as Compound Class SX326).

a compound represented by formula (L-55):

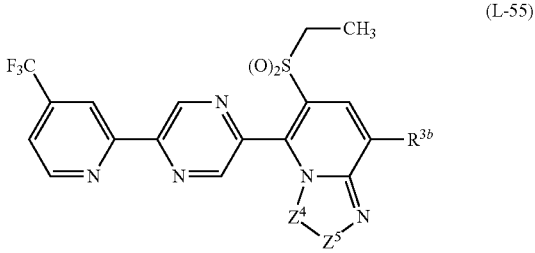

wherein $Z^4$ and $Z^5$ each represents $CH_2$, and $R^{3b}$ represents any substituents indicated in Table 7 to Table 15 (hereinafter, referred to as Compound Class SX327).

a compound represented by formula (L-55) wherein $Z^4$ represents $CH_2$, $Z^5$ represents C(O), and $R^{3b}$ represents any substituents indicated in Table 7 to Table 15 (hereinafter, referred to as Compound Class SX328).

a compound represented by formula (L-55) wherein $Z^4$ represents C(O), $Z^5$ represents $CH_2$, and $R^{3b}$ represents any substituents indicated in Table 7 to Table 15 (hereinafter, referred to as Compound Class SX329).

a compound represented by formula (L-55) wherein $Z^4$ represents NH, $Z^5$ represents C(O), and $R^{3b}$ represents any substituents indicated in Table 7 to Table 15 (hereinafter, referred to as Compound Class SX330).

a compound represented by formula (L-55) wherein $Z^4$ represents C(O), $Z^5$ represents NH, and $R^{3b}$ represents any substituents indicated in Table 7 to Table 15 (hereinafter, referred to as Compound Class SX331).

a compound represented by formula (L-55) wherein $Z^4$ represents NMe, $Z^5$ represents C(O), and $R^{3b}$ represents any substituents indicated in Table 7 to Table 15 (hereinafter, referred to as Compound Class SX332).

a compound represented by formula (L-55) wherein $Z^4$ represents C(O), $Z^5$ represents NMe, and $R^{3b}$ represents any substituents indicated in Table 7 to Table 15 (hereinafter, referred to as Compound Class SX333).

a compound represented by formula (L-56):

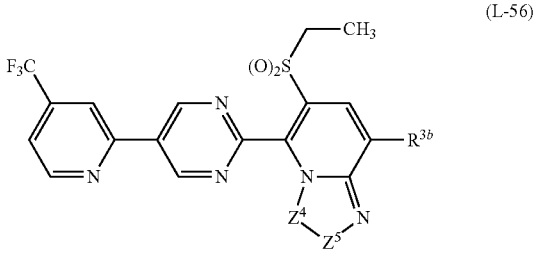

wherein $Z^4$ and $Z^5$ each represents $CH_2$, and $R^{3b}$ represents any substituents indicated in Table 7 to Table 15 (hereinafter, referred to as Compound Class SX334).

a compound represented by formula (L-56) wherein $Z^4$ represents $CH_2$, $Z^5$ represents C(O), and $R^{3b}$ represents any substituents indicated in Table 7 to Table 15 (hereinafter, referred to as Compound Class SX335).

a compound represented by formula (L-56) wherein $Z^4$ represents C(O), $Z^5$ represents $CH_2$, and $R^{3b}$ represents any substituents indicated in Table 7 to Table 15 (hereinafter, referred to as Compound Class SX336).

a compound represented by formula (L-56) wherein $Z^4$ represents NH, $Z^5$ represents C(O), and $R^{3b}$ represents any substituents indicated in Table 7 to Table 15 (hereinafter, referred to as Compound Class SX337).

a compound represented by formula (L-56) wherein $Z^4$ represents C(O), $Z^5$ represents NH, and $R^{3b}$ represents any substituents indicated in Table 7 to Table 15 (hereinafter, referred to as Compound Class SX338).

a compound represented by formula (L-56) wherein $Z^4$ represents NMe, $Z^5$ represents C(O), and $R^{3b}$ represents any substituents indicated in Table 7 to Table 15 (hereinafter, referred to as Compound Class SX339).

a compound represented by formula (L-56) wherein $Z^4$ represents C(O), $Z^5$ represents NMe, and $R^{5b}$ represents any substituents indicated in Table 7 to Table 15 (hereinafter, referred to as Compound Class SX340).

a compound represented by formula (L-57):

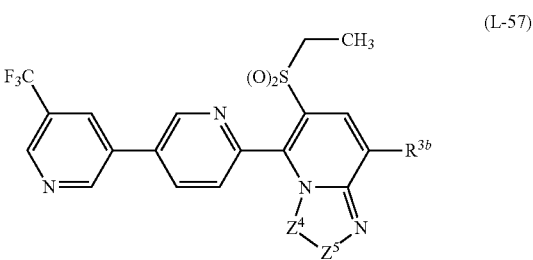

wherein $Z^4$ and $Z^5$ each represents $CH_2$, and $R^{3b}$ represents any substituents indicated in Table 7 to Table 15 (hereinafter, referred to as Compound Class SX341).

a compound represented by formula (L-57) wherein $Z^4$ represents $CH_2$, $Z^5$ represents C(O), and $R^{3b}$ represents any substituents indicated in Table 7 to Table 15 (hereinafter, referred to as Compound Class SX342).

a compound represented by formula (L-57) wherein $Z^4$ represents C(O), $Z^5$ represents $CH_2$, and $R^{3b}$ represents any substituents indicated in Table 7 to Table 15 (hereinafter, referred to as Compound Class SX343).

a compound represented by formula (L-57) wherein $Z^4$ represents NH, $Z^5$ represents C(O), and $R^{3b}$ represents any substituents indicated in Table 7 to Table 15 (hereinafter, referred to as Compound Class SX344).

a compound represented by formula (L-57) wherein $Z^4$ represents C(O), $Z^5$ represents NH, and $R^{3b}$ represents any substituents indicated in Table 7 to Table 15 (hereinafter, referred to as Compound Class SX345).

a compound represented by formula (L-57) wherein $Z^4$ represents NMe, $Z^5$ represents C(O), and $R^{3b}$ represents any substituents indicated in Table 7 to Table 15 (hereinafter, referred to as Compound Class SX346).

a compound represented by formula (L-57) wherein $Z^4$ represents C(O), $Z^5$ represents NMe, and $R^{3b}$ represents any substituents indicated in Table 7 to Table 15 (hereinafter, referred to as Compound Class SX347).

a compound represented by formula (L-58):

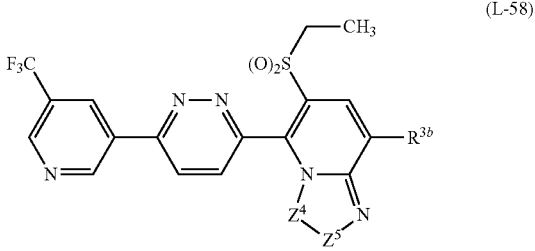

wherein $Z^4$ and $Z^5$ each represents $CH_2$, and $R^{3b}$ represents any substituents indicated in Table 7 to Table 15 (hereinafter, referred to as Compound Class SX348).

a compound represented by formula (L-58) wherein $Z^4$ represents $CH_2$, $Z^5$ represents C(O), and $R^{3b}$ represents any substituents indicated in Table 7 to Table 15 (hereinafter, referred to as Compound Class SX349).

a compound represented by formula (L-58) wherein $Z^4$ represents C(O), $Z^5$ represents $CH_2$, and $R^{3b}$ represents any substituents indicated in Table 7 to Table 15 (hereinafter, referred to as Compound Class SX350).

a compound represented by formula (L-58) wherein $Z^4$ represents NH, $Z^5$ represents C(O), and $R^{3b}$ represents any substituents indicated in Table 7 to Table 15 (hereinafter, referred to as Compound Class SX351).

a compound represented by formula (L-58) wherein $Z^4$ represents C(O), $Z^5$ represents NH, and $R^{3b}$ represents any substituents indicated in Table 7 to Table 15 (hereinafter, referred to as Compound Class SX352).

a compound represented by formula (L-58) wherein $Z^4$ represents NMe, $Z^5$ represents C(O), and $R^{3b}$ represents any substituents indicated in Table 7 to Table 15 (hereinafter, referred to as Compound Class SX353).

a compound represented by formula (L-58) wherein $Z^4$ represents C(O), $Z^5$ represents NMe, and $R^{3b}$ represents any substituents indicated in Table 7 to Table 15 (hereinafter, referred to as Compound Class SX354).

a compound represented by formula (L-59):

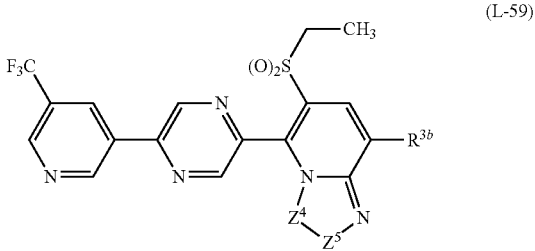

wherein $Z^4$ and $Z^5$ each represents $CH_2$, and $R^{3b}$ represents any substituents indicated in Table 7 to Table 15 (hereinafter, referred to as Compound Class SX355).

a compound represented by formula (L-59) wherein $Z^4$ represents $CH_2$, $Z^5$ represents C(O), and $R^{3b}$ represents any substituents indicated in Table 7 to Table 15 (hereinafter, referred to as Compound Class SX356).

a compound represented by formula (L-59) wherein $Z^4$ represents C(O), $Z^5$ represents $CH_2$, and $R^{3b}$ represents any substituents indicated in Table 7 to Table 15 (hereinafter, referred to as Compound Class SX357).

a compound represented by formula (L-59) wherein $Z^4$ represents NH, $Z^5$ represents C(O), and $R^{3b}$ represents any substituents indicated in Table 7 to Table 15 (hereinafter, referred to as Compound Class SX358).

a compound represented by formula (L-59) wherein $Z^4$ represents C(O), $Z^5$ represents NH, and $R^{3b}$ represents any substituents indicated in Table 7 to Table 15 (hereinafter, referred to as Compound Class SX359).

a compound represented by formula (L-59) wherein $Z^4$ represents NMe, $Z^5$ represents C(O), and $R^{3b}$ represents any substituents indicated in Table 7 to Table 15 (hereinafter, referred to as Compound Class SX360).

a compound represented by formula (L-59) wherein $Z^4$ represents C(O), $Z^5$ represents NMe, and $R^{5b}$ represents any substituents indicated in Table 7 to Table 15 (hereinafter, referred to as Compound Class SX361).

a compound represented by formula (L-60):

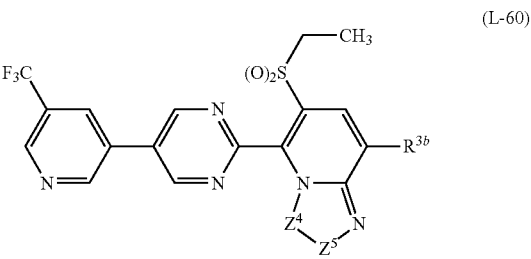

wherein $Z^4$ and $Z^5$ each represents $CH_2$, and $R^{3b}$ represents any substituents indicated in Table 7 to Table 15 (hereinafter, referred to as Compound Class SX362).

a compound represented by formula (L-60) wherein $Z^4$ represents $CH_2$, $Z^5$ represents C(O), and $R^{3b}$ represents any substituents indicated in Table 7 to Table 15 (hereinafter, referred to as Compound Class SX363).

a compound represented by formula (L-60) wherein $Z^4$ represents C(O), $Z^5$ represents $CH_2$, and $R^{3b}$ represents any substituents indicated in Table 7 to Table 15 (hereinafter, referred to as Compound Class SX364).

a compound represented by formula (L-60) wherein $Z^4$ represents NH, $Z^5$ represents C(O), and $R^{3b}$ represents any substituents indicated in Table 7 to Table 15 (hereinafter, referred to as Compound Class SX365).

a compound represented by formula (L-60) wherein $Z^4$ represents C(O), $Z^5$ represents NH, and $R^{3b}$ represents any substituents indicated in Table 7 to Table 15 (hereinafter, referred to as Compound Class SX366).

a compound represented by formula (L-60) wherein $Z^4$ represents NMe, $Z^5$ represents C(O), and $R^{3b}$ represents any substituents indicated in Table 7 to Table 15 (hereinafter, referred to as Compound Class SX367).

a compound represented by formula (L-60) wherein $Z^4$ represents C(O), $Z^5$ represents NMe, and $R^{3b}$ represents any substituents indicated in Table 7 to Table 15 (hereinafter, referred to as Compound Class SX368).

a compound represented by formula (L-61):

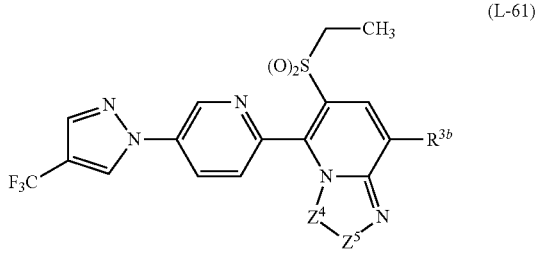

(L-61)

wherein $Z^4$ and $Z^5$ each represents $CH_2$, and $R^{3b}$ represents any substituents indicated in Table 7 to Table 15 (hereinafter, referred to as Compound Class SX369).

a compound represented by formula (L-61) wherein $Z^4$ represents $CH_2$, $Z^5$ represents C(O), and $R^{3b}$ represents any substituents indicated in Table 7 to Table 15 (hereinafter, referred to as Compound Class SX370).

a compound represented by formula (L-61) wherein $Z^4$ represents C(O), $Z^5$ represents $CH_2$, and $R^{3b}$ represents any substituents indicated in Table 7 to Table 15 (hereinafter, referred to as Compound Class SX371).

a compound represented by formula (L-61) wherein $Z^4$ represents NH, $Z^5$ represents C(O), and $R^{3b}$ represents any substituents indicated in Table 7 to Table 15 (hereinafter, referred to as Compound Class SX372).

a compound represented by formula (L-61) wherein $Z^4$ represents C(O), $Z^5$ represents NH, and $R^{3b}$ represents any substituents indicated in Table 7 to Table 15 (hereinafter, referred to as Compound Class SX373).

a compound represented by formula (L-61) wherein $Z^4$ represents NMe, $Z^5$ represents C(O), and $R^{3b}$ represents any substituents indicated in Table 7 to Table 15 (hereinafter, referred to as Compound Class SX374).

a compound represented by formula (L-61) wherein $Z^4$ represents C(O), $Z^5$ represents NMe, and $R^{3b}$ represents any substituents indicated in Table 7 to Table 15 (hereinafter, referred to as Compound Class SX375).

a compound represented by formula (L-62):

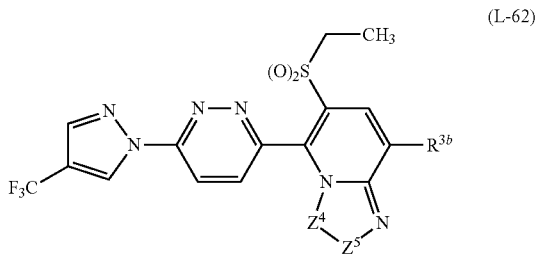

(L-62)

wherein $Z^4$ and $Z^5$ each represents $CH_2$, and $R^{3b}$ represents any substituents indicated in Table 7 to Table 15 (hereinafter, referred to as Compound Class SX376).

a compound represented by formula (L-62) wherein $Z^4$ represents $CH_2$, $Z^5$ represents C(O), and $R^{3b}$ represents any substituents indicated in Table 7 to Table 15 (hereinafter, referred to as Compound Class SX377).

a compound represented by formula (L-62) wherein $Z^4$ represents C(O), $Z^5$ represents $CH_2$, and $R^{3b}$ represents any substituents indicated in Table 7 to Table 15 (hereinafter, referred to as Compound Class SX378).

a compound represented by formula (L-62) wherein $Z^4$ represents NH, $Z^5$ represents C(O), and $R^{3b}$ represents any substituents indicated in Table 7 to Table 15 (hereinafter, referred to as Compound Class SX379).

a compound represented by formula (L-62) wherein $Z^4$ represents C(O), $Z^5$ represents NH, and $R^{3b}$ represents any substituents indicated in Table 7 to Table 15 (hereinafter, referred to as Compound Class SX380).

a compound represented by formula (L-62) wherein $Z^4$ represents NMe, $Z^5$ represents C(O), and $R^{3b}$ represents any referred to as Compound Class SX381).

a compound represented by formula (L-62) wherein $Z^4$ represents C(O), $Z^5$ represents NMe, and $R^{5b}$ represents any substituents indicated in Table 7 to Table 15 (hereinafter, referred to as Compound Class SX382).

a compound represented by formula (L-63):

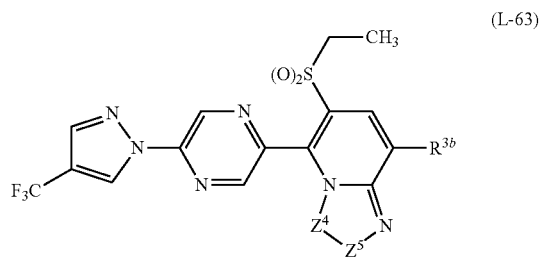

(L-63)

wherein $Z^4$ and $Z^5$ each represents $CH_2$, and $R^{3b}$ represents any substituents indicated in Table 7 to Table 15 (hereinafter, referred to as Compound Class SX383).

a compound represented by formula (L-63) wherein $Z^4$ represents $CH_2$, $Z^5$ represents C(O), and $R^{3b}$ represents any substituents indicated in Table 7 to Table 15 (hereinafter, referred to as Compound Class SX384).

a compound represented by formula (L-63) wherein $Z^4$ represents C(O), $Z^5$ represents $CH_2$, and $R^{3b}$ represents any substituents indicated in Table 7 to Table 15 (hereinafter, referred to as Compound Class SX385).

a compound represented by formula (L-63) wherein $Z^4$ represents NH, $Z^5$ represents C(O), and $R^{3b}$ represents any substituents indicated in Table 7 to Table 15 (hereinafter, referred to as Compound Class SX386).

a compound represented by formula (L-63) wherein $Z^4$ represents C(O), $Z^5$ represents NH, and $R^{3b}$ represents any substituents indicated in Table 7 to Table 15 (hereinafter, referred to as Compound Class SX387).

a compound represented by formula (L-63) wherein $Z^4$ represents NMe, $Z^5$ represents C(O), and $R^{3b}$ represents any substituents indicated in Table 7 to Table 15 (hereinafter, referred to as Compound Class SX388).

a compound represented by formula (L-63) wherein $Z^4$ represents C(O), $Z^5$ represents NMe, and $R^{3b}$ represents any substituents indicated in Table 7 to Table 15 (hereinafter, referred to as Compound Class SX389).

a compound represented by formula (L-64):

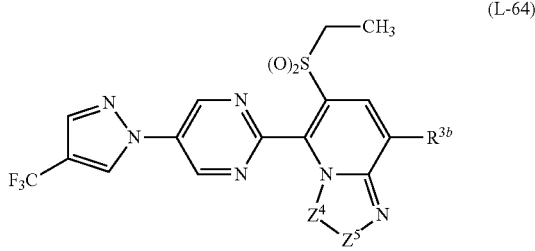

(L-64)

wherein $Z^4$ and $Z^5$ each represents $CH_2$, and $R^{3b}$ represents any substituents indicated in Table 7 to Table 15 (hereinafter, referred to as Compound Class SX390).

a compound represented by formula (L-64) wherein $Z^4$ represents $CH_2$, $Z^5$ represents $C(O)$, and $R^{3b}$ represents any substituents indicated in Table 7 to Table 15 (hereinafter, referred to as Compound Class SX391).

a compound represented by formula (L-64) wherein $Z^4$ represents $C(O)$, $Z^5$ represents $CH_2$, and $R^{3b}$ represents any substituents indicated in Table 7 to Table 15 (hereinafter, referred to as Compound Class SX392).

a compound represented by formula (L-64) wherein $Z^4$ represents NH, $Z^5$ represents $C(O)$, and $R^{3b}$ represents any substituents indicated in Table 7 to Table 15 (hereinafter, referred to as Compound Class SX393).

a compound represented by formula (L-64) wherein $Z^4$ represents $C(O)$, $Z^5$ represents NH, and $R^{3b}$ represents any substituents indicated in Table 7 to Table 15 (hereinafter, referred to as Compound Class SX394).

a compound represented by formula (L-64) wherein $Z^4$ represents NMe, $Z^5$ represents $C(O)$, and $R^{3b}$ represents any substituents indicated in Table 7 to Table 15 (hereinafter, referred to as Compound Class SX395).

a compound represented by formula (L-64) wherein $Z^4$ represents $C(O)$, $Z^5$ represents NMe, and $R^{3b}$ represents any substituents indicated in Table 7 to Table 15 (hereinafter, referred to as Compound Class SX396).

a compound represented by formula (L-65):

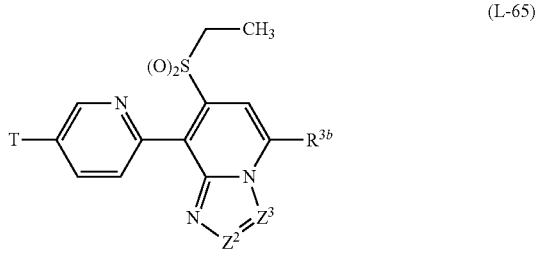

(L-65)

wherein $Z^2$ and $Z^3$ each represents CH, $R^{3b}$ represents a hydrogen atom, and T represents any substituents indicated in Table 1 to Table 6 (hereinafter, referred to as Compound Class SX397).

a compound represented by formula (L-65) wherein $Z^2$ and $R^3$ each represents CH, $R^{3b}$ represents a trifluoromethyl group, and T represents any substituents indicated in Table 1 to Table 6 (hereinafter, referred to as Compound Class SX398).

a compound represented by formula (L-65) wherein $Z^2$ represents CH, $Z^3$ represents a nitrogen atom, $R^{3b}$ represents a hydrogen atom, and T represents any substituents indicated in Table 1 to Table 6 (hereinafter, referred to as Compound Class SX399).

a compound represented by formula (L-65) wherein $Z^2$ represents CH, $Z^3$ represents a nitrogen atom, $R^{3b}$ represents a trifluoromethyl group, and T represents any substituents indicated in Table 1 to Table 6 (hereinafter, referred to as Compound Class SX400).

a compound represented by formula (L-65) wherein $Z^2$ represents a nitrogen atom, $Z^3$ represents CH, $R^{3b}$ represents a hydrogen atom, and T represents any substituents indicated in Table 1 to Table 6 (hereinafter, referred to as Compound Class SX401).

a compound represented by formula (L-65) wherein $Z^2$ represents a nitrogen atom, $Z^3$ represents CH, $R^{3b}$ represents a trifluoromethyl group, and T represents any substituents indicated in Table 1 to Table 6 (hereinafter, referred to as Compound Class SX402).

a compound represented by formula (L-65) wherein $Z^2$ and $Z^3$ each represents a nitrogen atom, $R^{3b}$ represents a hydrogen atom, and T represents any substituents indicated in Table 1 to Table 6 (hereinafter, referred to as Compound Class SX403).

a compound represented by formula (L-65) wherein $Z^2$ and $Z^3$ each represents a nitrogen atom, $R^{3b}$ represents a trifluoromethyl group, and T represents any substituents indicated in Table 1 to Table 6 (hereinafter, referred to as Compound Class SX404).

a compound represented by formula (L-66):

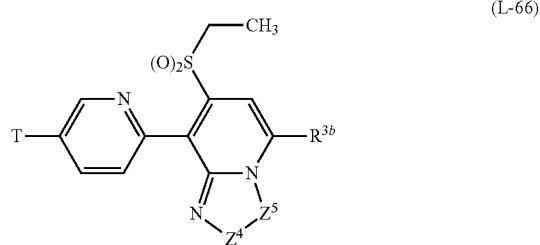

(L-66)

wherein $Z^4$ and $Z^5$ each represents $CH_2$, $R^{3b}$ represents a hydrogen atom, and T represents any substituents indicated in Table 1 to Table 6 (hereinafter, referred to as Compound Class SX405).

a compound represented by formula (L-66) wherein $Z^4$ and $Z^5$ each represents $CH_2$, $R^{3b}$ represents a trifluoromethyl group, and T represents any substituents indicated in Table 1 to Table 6 (hereinafter, referred to as Compound Class SX406).

a compound represented by formula (L-66) wherein $Z^4$ represents $CH_2$, $Z^5$ represents $C(O)$, $R^{5b}$ represents a hydrogen atom, and T represents any substituents indicated in Table 1 to Table 6 (hereinafter, referred to as Compound Class SX407).

a compound represented by formula (L-66) wherein $Z^4$ represents $CH_2$, $Z^5$ represents $C(O)$, $R^{3b}$ represents a trifluoromethyl group, and T represents any substituents indicated in Table 1 to Table 6 (hereinafter, referred to as Compound Class SX408).

a compound represented by formula (L-66) wherein $Z^4$ represents $C(O)$, $Z^5$ represents $CH_2$, $R^{3b}$ represents a hydrogen atom, and T represents any substituents indicated in Table 1 to Table 6 (hereinafter, referred to as Compound Class SX409).

a compound represented by formula (L-66) wherein $Z^4$ represents C(O), $7Z^J$ represents $CH_2$, $R^{3b}$ represents a trifluoromethyl group, and T represents any substituents indicated in Table 1 to Table 6 (hereinafter, referred to as Compound Class SX410).

a compound represented by formula (L-66) wherein $Z^4$ represents NH, $Z^5$ represents C(O), $R^{3b}$ represents a hydrogen atom, and T represents any substituents indicated in Table 1 to Table 6 (hereinafter, referred to as Compound Class SX411).

a compound represented by formula (L-66) wherein $Z^4$ represents NH, $Z^5$ represents C(O), $R^{3b}$ represents a trifluoromethyl group, and T represents any substituents indicated in Table 1 to Table 6 (hereinafter, referred to as Compound Class SX412).

a compound represented by formula (L-66) wherein $Z^4$ represents C(O), $Z^5$ represents NH, $R^{3b}$ represents a hydrogen atom, and T represents any substituents indicated in Table 1 to Table 6 (hereinafter, referred to as Compound Class SX413).

a compound represented by formula (L-66) wherein $Z^4$ represents C(O), $Z^5$ represents NH, $R^{3b}$ represents a trifluoromethyl group, and T represents any substituents indicated in Table 1 to Table 6 (hereinafter, referred to as Compound Class SX414).

a compound represented by formula (L-66) wherein $Z^4$ represents NMe, $Z^5$ represents C(O), $R^{3b}$ represents a hydrogen atom, and T represents any substituents indicated in Table 1 to Table 6 (hereinafter, referred to as Compound Class SX415).

a compound represented by formula (L-66) wherein $Z^4$ represents NMe, $Z^5$ represents C(O), $R^{3b}$ represents a trifluoromethyl group, and T represents any substituents indicated in Table 1 to Table 6 (hereinafter, referred to as Compound Class SX416).

a compound represented by formula (L-66) wherein $Z^4$ represents C(O), $Z^5$ represents NMe, $R^{3b}$ represents a hydrogen atom, and T represents any substituents indicated in Table 1 to Table 6 (hereinafter, referred to as Compound Class SX417).

a compound represented by formula (L-66) wherein $Z^4$ represents C(O), $Z^5$ represents NMe, $R^{3b}$ represents a trifluoromethyl group, and T represents any substituents indicated in Table 1 to Table 6 (hereinafter, referred to as Compound Class SX417).

a compound represented by formula (L-67):

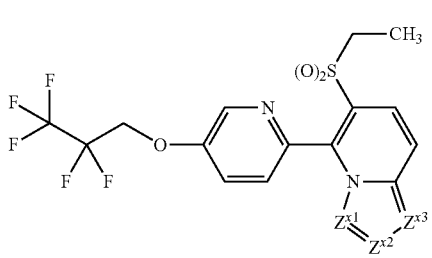

(L-67)

wherein $Z^{x1}$, $Z^{x2}$ and $Z^{x3}$ each represents any combinations of the substituents indicated in Table 16 and Table 17 (hereinafter, referred to as Compound Class SX419).

TABLE 16

| $Z^{X1}$ | $Z^{X2}$ | $Z^{X3}$ |
|---|---|---|
| CH | CH | CH |
| CH | CH | CMe |
| CH | CH | CPh |
| N | CF | N |
| N | CCl | N |
| N | CMe | N |
| N | C(OMe) | N |
| N | C(CF$_3$) | N |
| N | C(NH$_2$) | N |
| N | C(NO$_2$) | N |
| N | C(CN) | N |
| N | C(COOMe) | N |
| N | C(CONHMe) | N |
| N | CPh | N |
| N | C(Py2) | N |
| N | C(Py3) | N |
| N | C(Py4) | N |
| N | C(c-Pr) | N |
| CH | CF | N |
| CH | CCl | N |
| CH | CMe | N |
| CH | C(OMe) | N |
| CH | C(CF$_3$) | N |
| CH | C(NH$_2$) | N |
| CH | C(NO$_2$) | N |
| CH | C(CN) | N |
| CH | C(COOMe) | N |
| CH | C(CONHMe) | N |
| CH | CPh | N |
| CH | C(Py2) | N |
| CH | C(Py3) | N |
| CH | C(Py4) | N |
| CH | C(c-Pr) | N |

TABLE 17

| $Z^{X1}$ | $Z^{X2}$ | $Z^{X3}$ |
|---|---|---|
| CF | CH | N |
| CCl | CH | N |
| CMe | CH | N |
| C(OMe) | CH | N |
| C(CF$_3$) | CH | N |
| C(NH$_2$) | CH | N |
| C(NO$_2$) | CH | N |
| C(CN) | CH | N |
| C(COOMe) | CH | N |
| C(CONHMe) | CH | N |
| CPh | CH | N |
| C(Py2) | CH | N |
| C(Py3) | CH | N |
| C(Py4) | CH | N |
| C(c-Pr) | CH | N |
| CCl | CCl | N |
| CMe | CMe | N |
| CMe | CCl | N |
| CF | N | N |
| CCl | N | N |
| CMe | N | N |
| C(OMe) | N | N |
| C(CF$_3$) | N | N |
| C(NH$_2$) | N | N |
| C(NO$_2$) | N | N |
| C(CN) | N | N |
| C(COOMe) | N | N |
| C(CONHMe) | N | N |
| CPh | N | N |
| C(Py2) | N | N |
| C(Py3) | N | N |
| C(Py4) | N | N |
| C(c-Pr) | N | N | a compound represented by formula (L-68):

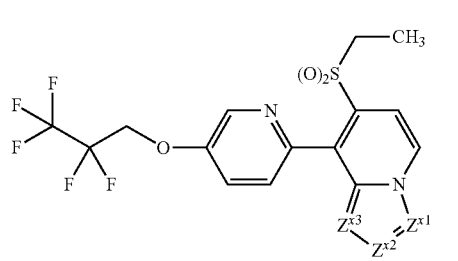

wherein $Z^{x1}$, $Z^{x2}$ and $Z^{x3}$ each represents any combinations of the substituents indicated in Table 16 and Table 17 (hereinafter, referred to as Compound Class SX420).

a compound represented by formula (L-69):

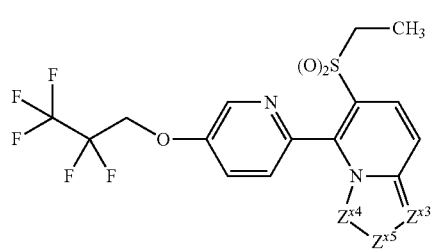

wherein $Z^{x5}$, $Z^{x4}$ and $Z^{x5}$ each represents any combinations of the substituents indicated in Table 18 (hereinafter, referred to as Compound Class SX421).

a compound represented by formula (L-70):

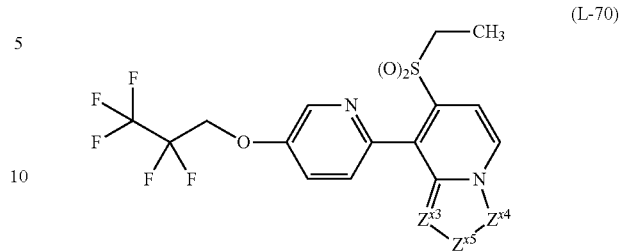

wherein $Z^{x3}$, $Z^{x4}$ and $Z^{x5}$ each represents any combinations of the substituents indicated in Table 18 (hereinafter, referred to as Compound Class SX422).

The compound of the present invention may be mixed or combined with one or more ingredients selected from a group consisting of the following Group (a), Group (b), Group (c), Group (d), and Group (e) (hereinafter, referred to as "Present ingredient").

The above-mentioned mixing or combining represents a use of the Present compound and the Present ingredient at same time, separately or at certain intervals.

When the Present compound and the present ingredient are used at the same time, the Present compound and the Present ingredient may be contained in separate formulations respectively, or may be contained in the same one formulation.

One aspect of the present invention is a composition comprising one or more ingredients selected from Group (a), Group (b), Group (c), Group (d) and Group (e) (that is, Present ingredient) as well as the Present compound.

Group (a) represents an insecticidal ingredient group, a miticidal ingredient group, or a nematicidal ingredient group, which is selected from the group consisting of the following sub group a-1 to sub group a-10.

Sub group a-1: Carbamate acetylcholinesterase (AChE) inhibitors
Sub group a-2: Organophosphorus acetylcholinesterase (AChE) inhibitors
Sub group a-3: GABA-gated chloride channel blockers
Sub group a-4: GABA-gated chloride channel allosteric modulators
Sub group a-5: Sodium channel modulators
Sub group a-6: Nicotinic acetylcholine receptor (nAChR) competitive modulators
Sub group a-7: Ryanodine receptor modulators
Sub group a-8: Microbial materials
Sub group a-9: Nematicidal ingredients
Sub group a-10: The other group as insecticidal active ingredients and miticidal active ingredients Group (b) represents a fungicidal active ingredient group selected from the group consisting of the following sub group b-1 to sub group b-18.

Sub group b-1: PA fungicides (Phenyl amide)
Sub group b-2: MBC fungicides (methyl benzimidazole carbamate)
Sub group b-3: Thiazole carboxamides
Sub group b-4: SDHI (Succinate dehydrogenase inhibitors)
Sub group b-5: QoI fungicides (Qo Inhibitors)
Sub group b-6: QiI fungicides (Qi Inhibitors)
Sub group b-7: Thiophene carboxamides
Sub group b-8: AP fungicides (Anilinopyrimidine)
Sub group b-9: PP fungicides (Phenylpyrrole)
Sub group b-10: AH fungicides (Aromatic hydrocarbons)
Sub group b-11: DMI fungicides (Demethylation inhibitors)

TABLE 18

| $Z^{x3}$ | $Z^{x4}$ | $Z^{x5}$ |
|---|---|---|
| CH | $CH_2$ | $CH_2$ |
| N | CHMe | $CH_2$ |
| N | $CH_2$ | CHMe |
| N | CHMe | CHMe |
| N | $CH_2$ | $CH(CF_3)$ |
| N | $CH_2$ | CHPh |
| N | $CH_2$ | CH(c-Pr) |
| N | CHMe | C(O) |
| N | $CH(CF_3)$ | C(O) |
| N | CHPh | C(O) |
| N | CH(c-Pr) | C(O) |
| N | C(O) | CHMe |
| N | C(O) | $CH(CF_3)$ |
| N | C(O) | CHPh |
| N | C(O) | CH(c-Pr) |
| N | C(O) | $N(CH_2CF_3)$ |
| N | C(O) | NPh |
| N | C(O) | NPy2 |
| N | C(O) | N(c-Pr) |
| N | C(O) | N(COMe) |
| N | C(O) | N(COOMe) |
| N | C(O) | N(CONHMe) |
| N | C(O) | N($SO_2$Me) |
| N | $N(CH_2CF_3)$ | C(O) |
| N | NPh | C(O) |
| N | NPy2 | C(O) |
| N | N(c-Pr) | C(O) |
| N | N(COMe) | C(O) |
| N | N(COOMe) | C(O) |
| N | N(CONHMe) | C(O) |
| N | N($SO_2$Me) | C(O) |

Sub group b-12: CCA fungicides (Carboxylic acid amide)
Sub group b-13: Piperidinyl thiazole isoxazoline
Sub group b-14: Tetrazolyl oxime
Sub group b-15: Dithiocarbamate
Sub group b-16: Phthalimide
Sub group b-17: Microbial fungicides
Sub group b-18: Other fungicides Group (c) represents a plant growth modulating ingredients group selected from the group consisting of the following sub group c-1, sub group c-2, and sub group c-3.
Sub group c-1: Plant growth modulating compounds
Sub group c-2: Mycorrhizal fungi group
Sub group c-3: Root nodule bacteria group Group (d) represents a phytotoxicity-reducing ingredient group.

Group (e) represents a synergist group.

The composition comprising the above-mentioned present ingredient and the present compound can exert an effect of the composition depending on the content (s) or the content ratio of the above-mentioned present ingredient(s) or the above-mentioned present compound in the above-mentioned composition. Accordingly, the use of the above-mentioned composition may be decided depending on the effect that is produced by the above-mentioned composition. The above-mentioned composition may have one or two or more applied use.

One embodiment of the above-mentioned composition is an agrochemical composition.

Also, another embodiment of the above-mentioned composition is an insecticidal, miticidal or nematicidal composition.

Also, another embodiment of the above-mentioned composition is a fungicidal composition.

Also, another embodiment of the above-mentioned composition is a plant growth modulating composition.

Also, another embodiment of the above-mentioned composition is a phytotoxicity-reducing composition.

Examples of the combination of the Present ingredient and the Present compound are described below. For example, alanycarb+SX means a combination of alanycarb and SX.

The symbol of "SX" represents any one of the present compound selected from the Compound Class $SX_1$ to the Compound Class $SX_{422}$. Also, all of the below-mentioned present ingredient are known ingredients, and are commercially available or can be produced by a known method. If the present ingredient is a bacteria, it is available from the bacterial authority depository. The numerical number in bracket represents a CAS register number.

Examples of the combination of the Present ingredient of the above sub group a-1 and the Present compound:
alanycarb+SX, aldicarb+SX, bendiocarb+SX, benfuracarb+SX, butocarboxim+SX, butoxycarboxim+SX, carbaryl: NAC+SX, carbofuran+SX, carbosulfan+SX, ethiofencarb+SX, fenobucarb: BPMC+SX, formetanate+SX, furathiocarb+SX, isoprocarb: MI PC+SX, methiocarb+SX, methomyl+SX, metolcarb+SX, oxamyl+SX, pirimicarb+SX, propoxur: PHC+SX, thiodicarb+SX, thiofanox+SX, triazamate+SX, trimethacarb+SX, XMC+SX, xylylcarb+SX.

Examples of the combination of the Present ingredient of the above sub group a-2 and the Present compound:
acephate+SX, azamethiphos+SX, azinphos-ethyl+SX, azinphos-methyl+SX, cadusafos+SX, chlorethoxyfos+SX, chlorfenvinphos+SX, chlormephos+SX, chlorpyrifos+SX, chlorpyrifos-methyl+SX, coumaphos+SX, cyanophos: CYAP+SX, demeton-S-methyl+SX, diazinon+SX, dichlorvos: DDVP+SX, dicrotophos+SX, dimethoate+SX, dimethyl vinphos+SX, disulfoton+SX, EPN+SX, ethion+SX, ethoprophos+SX, famphur+SX, fenamiphos+SX, fenitrothion: MEP+SX, fenthion: MPP+SX, fosthiazate+SX, heptenophos+SX, imicyafos+SX, isofenphos+SX, isopropyl-O-(methoxyaminothiophosphoryl)salicylate+SX, isoxathion+SX, malathion+SX, mecarbam+SX, methamidophos+SX, methidathion: DMTP+SX, mevinphos+SX, monocrotophos+SX, naled: BRP+SX, omethoate+SX, oxydemeton-methyl+SX, parathion+SX, parathion-methyl+SX, phenthoate: PAP+SX, phorate+SX, phosalone+SX, phosmet: PMP+SX, phosphamidon+SX, phoxim+SX, pirimiphos-methyl+SX, profenofos+SX, propetamphos+SX, prothiofos+SX, pyraclofos+SX, pyridaphenthion+SX, quinalphos+SX, sulfotep+SX, tebupirimfos+SX, temephos+SX, terbufos+SX, tetrachlorvinphos+SX, thiometon+SX, triazophos+SX, trichlorfon: DEP+SX, vamidothion+SX.

Examples of the combination of the Present ingredient of the above sub group a-3 and the Present compound:
ethiprole+SX, fipronil+SX, flufiprole+SX, chlordane+SX, endosulfan+SX, alpha-endosulfan+SX.

Examples of the combination of the Present ingredient of the above sub group a-4 and the Present compound:
afoxolaner+SX, fluralaner+SX, broflanilide+SX, fluxametamide+SX.

Examples of the combination of the Present ingredient of the above sub group a-5 and the Present compound:
acrinathrin+SX, allethrin+SX, bifenthrin+SX, kappa-bi fenthrin+SX, bioallethrin+SX, bioresmethrin+SX, cyclopro-thrin+SX, cyfluthrin+SX, beta-cyfluthrin+SX, cyhalothrin+SX, gamma-cyhalothrin+SX, lambda-cyhalothrin+SX, cypermethrin+SX, alpha-cypermethrin+SX, beta-cypermethrin+SX, theta-cypermethrin+SX, zeta-cypermethrin+SX, cyphenothrin+SX, deltamethrin+SX, empenthrin+SX, esfenvalerate+SX, etofenprox+SX, fenpropathrin+SX, fenvalerate+SX, flucythrinate+SX, flumethrin+SX, f luvalinate+SX, tau-f luvalinate+SX, halfenprox+SX, heptaflu-thrin+SX, imiprothrin+SX, kadethrin+SX, meperfluthrin+SX, momfluorothrin+SX, permethrin+SX, phenothrin+SX, prallethrin+SX, pyrethrins+SX, resmethrin+SX, silaflu-ofen+SX, tefluthrin+SX, kappa-tefluthrin+SX, tetramethrin+SX, tetramethylfluthrin+SX, tralomethrin+SX, transfluthrin+SX, benfluthrin+SX, flufenoprox+SX, flumethrin+SX, sigma-cypermethrin+SX, furamethrin+SX, metofluthrin+SX, profluthrin+SX, dimefluthrin+SX, epsilon-metofluthrin+SX, epsilon-momfluorothrin+SX, methoxychlor+SX.

Examples of the combination of the Present ingredient of the above sub group a-6 and the Present compound:
acetamiprid+SX, clothianidin+SX, dinotefuran+SX, imidacloprid+SX, nitenpyram+SX, thiacloprid+SX, thiamethoxam+SX, sulfoxaflor+SX, flupyradifurone+SX, triflumezopyrim+SX, dicloromezotiaz+SX, cycloxaprid+SX, (E)-N-{1-[(6-chloropyridin-3-yl)methyl]pyridine-2(1H)-ylidene}-2,2,2-trifluoroacetamide (1689566-03-7)+SX.

Examples of the combination of the Present ingredient of the above sub group a-7 and the Present compound:
chlorantraniliprole+SX, cyantraniliprole+SX, cyclonilip-role+SX, flubendiamide+SX, tetraniliprole+SX, cyhalodi-amide+SX, 3-bromo-N-[2,4-dichloro-6-(methylcarbamoyl) phenyl]-1-(3,5-dichloropyridin-2-yl)-1H-pyrazole-5-carboxamide (1104384-14-6)+SX.

Examples of the combination of the Present ingredient of the above sub group a-8 and the Present compound:
*Beauveria bassiana*+SX, *Beauveria brongniartii*+SX, *Paecilomyces* fumosoroseus+SX, *Paecilomyces lilacinus*+SX, *Paecilomyces tenuipes*+SX, *Verticillium* lecani+SX, *Arthrobotrys dactyloides*+SX, *Bacillus thuringiensis*+SX,

*Bacillus firmus*+SX, *Bacillus megaterium*+SX, *Hirsutella rhossiliensis*+SX, *Hirsutella minnesotensis*+SX, *Monacrosporiuin phymatopagus*+SX, *Pasteuria nishizawae*+SX, *Pasteuria penetrans*+SX, *Pasteuria usgae*+SX, *Verticillium chlamydosporium*+SX.

Examples of the combination of the Present ingredient of the above sub group a-9 and the Present compound:
abamectin+SX, fluazaindolizine+SX, fluensulfone+SX, fluopyram+SX, tioxazafen+SX.

Examples of the combination of the Present ingredient of the above sub group a-10 and the Present compound:
spinetoram+SX, spinosad+SX, emamectin-benzoate+SX, lepimectin+SX, milbemectin+SX, hydroprene+SX, kinoprene+SX, methoprene+SX, fenoxycarb+SX, pyriproxyfen+SX, methyl bromide+SX, chloropicrin+SX, sulfuryl fluoride+SX, sodium aluminium fluoride or chiolite+SX, borax+SX, boric acid+SX, disodium octaborate+SX, sodium borate+SX, sodium metaborate+SX, tartar emetic+SX, dazomet+SX, metam+SX, pymetrozine+SX, pyrifluquinazone+SX, clofentezine+SX, hexythiazox+SX, diflovidazin+SX, etoxazole+SX, diafenthiuron+SX, azocyclotin+SX, cyhexatin+SX, fenbutatin oxide+SX, propargite+SX, tetradifon+SX, chlorfenapyr+SX, DNOC+SX, sulfluramid+SX, bensultap+SX, cartap+SX, cartap hydrochloride+SX, thiocyclam+SX, thiosultap-disodium+SX, thiosultap-monosodium+SX, bistrifluron+SX, chlorfluazuron+SX, diflubenzuron+SX, fluazuron+SX, flucycloxuron+SX, flufenoxuron+SX, hexaflumuron+SX, lufenuron+SX, novaluron+SX, noviflumuron+SX, teflubenzuron+SX, triflumuron+SX, buprofezin+SX, cyromazine+SX, chromafenozide+SX, halofenozide+SX, methoxyfenoz ide+SX, tebufenozide+SX, amitraz+SX, hydramethylnon+SX, acequinocyl+SX, fluacrypyrim+SX, bifenazate+SX, fenazaquin+SX, fenpyroximate+SX, pyridaben+SX, pyrimidifen+SX, tebufenpyrad+SX, tolfenpyrad+SX, rotenone+SX, indoxacarb+SX, metaflumizone+SX, spirodiclofen+SX, spiromesifen+SX, spirotetramat+SX, aluminium phosphide+SX, calcium phosphide+SX, phosphine+SX, zinc phosphide+SX, calcium cyanide+SX, potassium cyanide+SX, sodium cyanide+SX, cyenopyrafen+SX, cyflumetofen+SX, pyflubumide+SX, flonicamid+SX, azadirachtin+SX, benzoximate+SX, bromopropylate+SX, chinomethionat+SX, dicofol+SX, pyridalyl+SX, lime sulfur+SX, sulfur+SX, machine oil+SX, nicotine+SX, nicotine-sulfate+SX, afidopyropen+SX, flometoquin+SX, metoxadiazone+SX, pyriminostrobin+SX,
N-[3-chloro-1-(pyridin-3-yl)-1H-pyrazol-4-yl]-N-ethyl-3-(3,3,3-trifluoropropylsulfanyl)propanamide (1477919-27-9)+SX,
N-[3-chloro-1-(pyridin-3-yl)-1H-pyrazol-4-yl]-N-ethyl-3-(3,3,3-trifluoropropanesulfinyl)propanamide (1477923-37-7)+SX,
5-(1,3-dioxan-2-yl)-4-[4-(trifluoromethyl)benzyloxy]pyrmidine (1449021-97-9)+SX,
2-[3-(ethanesulfonyl)pyridin-2-yl]-5-(trifluoromethanesulfonyl)benzoxazole (1616678-32-0)+SX,
4-[5-(3,5-dichlorophenyl)-5-(trifluorophenyl)-4,5-dihydro-1,2-oxazol-3-yl]-2-methyl-N-(1-oxothietan-3-yl)benzamide (1241050-20-3)+SX,
3-methoxy-N-(5-{5-(trifluorophenyl)-5-[3-(trifluorophenyl)phenyl]-4,5-dihydro-1,2-oxazol-3-yl}indan-1-yl)propanamide (1118626-57-5)+SX,
3-(4-chloro-2,6-dimethylphenyl)-4-[(ethoxycarbonyl)oxy]-8-methoxy-1-methyl-1,8-diazaspiro[4.5]deca-3-ene-2-one (1229023-00-0)+SX,
N-[2-bromo-6-chloro-4-(1,1,1,2,3,3,3-heptafluropropan-2-yl)phenyl]-3-[ethyl-[(pyridin-4-yl)carbonyl]amino}-2-methoxybenzamide (1429513-53-0)+SX,
N-[2-bromo-6-chloro-4-(1,1,1,2,3,3,3-heptafluropropan-2-yl)phenyl]-3-[ethyl-(4-cyanobenzoyl)amino]-2-methoxybenzamide (1609007-65-9)+SX,
N-[2-bromo-6-difluoromethoxy-4-(1,1,1,2,3,3,3-heptafluropropan-2-yl)phenyl]-3-{methyl[pyridin-4-yl)carbonyl]amino}-2-methoxybenzamide (1630969-78-6)+SX,
1-{2-fluroro-4-methyl-5-[(2,2,2-trifluoroethyl)sulfinyl]phenyl}-3-(trifluorophenyl)-1H-1,2,4-triazole-5-amine (885026-50-6)+SX, and
3-endo-[2-propoxy-4-(trifluorophenyl)phenoxy]-9-{[5-(trifluorophenyl)pyridin-2-yl]oxy}-9-azacyclo[3.3.1]nonane the (1332838-17-1)+SX.

Examples of the combination of the Present active ingredient of the above sub group b-1 and the Present compound:
benalaxyl+SX, benalaxyl-M+SX, f uralaxyl+SX, metalaxyl+SX, metalaxyl-M+SX, oxadixyl+SX, ofurace+SX.

Examples of the combination of the Present active ingredient of the above sub group b-2 and the Present compound:
benomyl+SX, carbendazim+SX, fuberidazole+SX, thiabendazole+SX, thiophanate+SX, thiophanate-methyl+SX.

Examples of the combination of the Present active ingredient of the above sub group b-3 and the Present compound:
ethaboxam+SX.

Examples of the combination of the Present active ingredient of the above sub group b-4 and the Present compound:
benodanil+SX, flutolanil+SX, mepronil+SX, isofetamid+SX, fenfuram+SX, carboxin+SX, oxycarboxin+SX, thifluzamide+SX, benzovindiflupyr+SX, bixafen+SX, f luxapyroxad+SX, furametpyr+SX, isopyrazam+SX, penflufen+SX, penthiopyrad+SX, sedaxane+SX, pydiflumetofen+SX, boscalid+SX, pyraziflumid+SX,
3-difluoromethyl-N-methoxy-1-methyl-N-[(1R)-1-methyl-2-(2,4,6-trichlorophenyl)ethyl]pyrazol-4-carboxamide (1639015-48-7)+SX,
3-difluoromethyl-N-methoxy-1-methyl-N-[(1S)-1-methyl-2-(2,4,6-trichlorophenyl)ethyl]pyrazol-4-carboxamide (1639015-49-8)+SX,
N-cyclopropyl-3-(difluoromethyl)-5-fluoro-N-(5-chloro-2-isopropylbenzyl)-1-methyl-1H-pyrazole-4-carboxamide (1255734-28-1)+SX,
3-difluoromethyl-1-methyl-N-(1,1,3-trimethylindan-4-yl)pyrazole-4-carboxamide (141573-94-6)+SX,
3-difluoromethyl-1-methyl-N-[(3R)-1,1,3-trimethylindan-4-yl]pyrazole-4-carboxamide (1352994-67-2)+SX,
3-difluoromethyl-N-(7-fluoro-1,1,3-trimethylindan-4-yl)-1-methylpyazole-4-carboxamide (1383809-87-7)+SX,
3-difluoromethyl-N-[(3R)-7-fluoro-1,1,3-trimethylindan-4-yl]-1-methylpyrazole-4-carboxamide (1513466-73-3)+SX.

Examples of the combination of the Present active ingredient of the above sub group b-5 and the Present compound:
azoxystrobin+SX, coumoxystrobin+SX, enoxastrobin+SX, flufenoxystrobin+SX, picoxystrobin+SX, pyraoxystrobin+SX, mandestrobin+SX, pyraclostrobin+SX, pyrametostrobin+SX, triclopyricarb+SX, kresoxim-methyl+SX, trifloxystrobin+SX, dimoxyst robin+SX, fenaminstrobin+SX, metominostrobin+SX, orysastrobin+SX, famoxadone+SX, fluoxast robin+SX, fenamidone+SX, pyribencarb+SX.

Examples of the combination of the Present active ingredient of the above sub group b-6 and the Present compound:
cyazofamid+SX, amisulbrom+SX, binapacryl+SX, meptyldinocap+SX, dinocap+SX, fluazinam+SX.

Examples of the combination of the Present active ingredient of the above sub group b-7 and the Present compound:

silthiofam+SX.

Examples of the combination of the Present active ingredient of the above sub group b-8 and the Present compound:
cyprodinil+SX, mepanipyrim+SX, pyrimethanil+SX.

Examples of the combination of the Present active ingredient of the above sub group b-9 and the Present compound:
fenpiclonil+SX, fludioxonil+SX.

Examples of the combination of the Present active ingredient of the above sub group b-10 and the Present compound:
biphenyl+SX, chloroneb+SX, dicloran+SX, quintozene+SX, tecnazene+SX, tolclofos-methyl+SX.

Examples of the combination of the Present active ingredient of the above sub group b-11 and the Present compound:
azaconazole+SX, bitertanol+SX, bromuconazole+SX, cyproconazole+SX, difenoconazole+SX, diniconazole+SX, diniconazole-M+SX, epoxiconazole+SX, etaconazole+SX, fenbuconazole+SX, fluquinconazole+SX, flusilazole+SX, flutriafol+SX, hexaconazole+SX, imibenconazole+SX, ipconazole+SX, ipfentrifluconazole+SX, mefentrifluconazole+SX, metconazole+SX, myclobutanil+SX, penconazole+SX, propiconazole+SX, simeconazole+SX, tebuconazole+SX, tetraconazole+SX, triadimefon+SX, triadimenol+SX, triticonazole+SX, prothioconazole+SX, triforine+SX, pyrifenox+SX, pyrisoxazole+SX, fenarimol+SX, nuarimol+SX, imazalil+SX, oxpoconazole+SX, oxpoconazole fumarate+SX, pefurazoate+SX, prochloraz+SX, triflumizole+SX.

Examples of the combination of the Present active ingredient of the above sub group b-12 and the Present compound:
dimethomorph+SX, flumorph+SX, pyrimorph+SX, benthiavalicarb+SX, benthivalicarb-isopropyl+SX, iprovalicarb+SX, valifenalate+SX, mandipropamid+SX.

Examples of the combination of the Present active ingredient of the above sub group b-13 and the Present compound:
oxathiapiprolin+SX.

Examples of the combination of the Present active ingredient of the above sub group b-14 and the Present compound:
picarbutrazox+SX.

Examples of the combination of the Present active ingredient of the above sub group b-15 and the Present compound:
ferbam+SX, mancozeb+SX, maneb+SX, metiram+SX, propineb+SX, thiram+SX, zineb+SX, ziram+SX.

Examples of the combination of the Present active ingredient of the above sub group b-16 and the Present compound:
captan+SX, captafol+SX, folpet+SX.

Examples of the combination of the Present active ingredient of the above sub group b-17 and the Present compound:
*Agrobacterium radiobactor* strains (such as its 84 strain)+SX, *Bacillus amyloliquefaciens*+SX, *Bacillus amyloliquefaciens* strain QST713+SX, *Bacillus amyloliquefaciens* strain FZB24+SX, *Bacillus amyloliquefaciens* strain MBI600+SX, *Bacillus amyloliquefaciens* strain D747+SX, *Bacillus amyloliquefaciens* strain AT332+SX, *Bacillus amyloliquefaciens* strain PTA4838+SX, *Bacillus pumilus*+SX, *Bacillus simplex* CGF2856 strains (such as its CGF2856 strain)+SX, *Bacillus subtilis*+SX, *Bacillus subtilis* strain QST713+SX, *Bacillus subtilis* strain HAI0404+SX, *Bacillus subtilis* strain Y1336+SX, *Variovorax paradoxus* strains (such as its CGF4526 strain)+SX, *Erwinia carotovora* strains (such as its CGE234M403 strain)+SX, *Pseudomonas fluorescens* strains (such as its G7090 strain)+SX, *Talaromyces flavus* strains (such as its SAY-Y-94-01 strain)+SX, *Trichoderma atroviride* strains (such as its SKT-1 strain), *Trichoderma harzianum* strains+SX, Harpin protein+SX.

Examples of the combination of the Present active ingredient of the above sub group b-18 and the Present compound:
bupirimate+SX, dimethirimol+SX, ethirimol+SX, hymexazole+SX, octhilinone+SX, oxolinic acid+SX, diethofencarb+SX, zoxamide+SX, pencycuron+SX, fluopicolide+SX, phenamacril+SX, diflumetorim+SX, tolfenpyrad+SX, fentin acetate+SX, fentin chloride+SX, fentin hydroxide+SX, ametoctradin+SX, blasticidin-S+SX, kasugamycin+SX, streptomycin+SX, oxytetracycline+SX, quinoxyfen+SX, proquinazid+SX, chlozolinate+SX, dimethachlone+SX, iprodione+SX, procymidone+SX, vinclozolin+SX, edifenphos+SX, iprobenfos+SX, pyrazophos+SX, isoprothiolane+SX, etridiazole+SX, iodocarb+SX, propamocarb+SX, prothiocarb+SX, aldimorph+SX, dodemorph+SX, fenpropidin+SX, fenpropimorph+SX, piperalin+SX, spiroxamine+SX, tridemorph+SX, fenhexamid+SX, fenpyrazamine+SX, pyributicarb+SX, naftifine+SX, terbinafine+SX, polyoxins+SX, phthalide+SX, pyroquilon+SX, tricyclazole+SX, carpropamid+SX, diclocymet+SX, fenoxanil+SX, tolprocarb+SX, acibenzolar-S-methyl+SX, probenazole+SX, tiadinil+SX, isotianil+SX, laminarin+SX, cymoxanil+SX, fosetyl+SX, teclof thalam+SX, triazoxide+SX, flusulfamide+SX, diclomezine+SX, methasulfocarb+SX, cyflufenamid+SX, metrafenone+SX, pyriofenone+SX, dodine+SX, flutianil+SX, ferimzone+SX, tebufloquin+SX, validamycin+SX, basic copper chloride+SX, copper(II) hydroxide+SX, basic copper sulphate+SX, Dodecylbenzenesulphonic acid bisethylenediamine copper [II] salt (DBEDC)+SX, organocopper+SX, sulfur+SX, chlorothalonil+SX, dichlofluanid+SX, tolylfluanid+SX, guazatine+SX, iminoctadine+SX, anilazine+SX, dithianon+SX, chinomethionat+SX, fluoroimide+SX, dipymetitrone+SX, quinofumelin+SX, dichlobentiazox+SX, 3-chloro-5-phenyl-6-methyl-4-(2,6-difluorophenyl)pyridazine (1358061-55-8)+SX, fenpicoxamid+SX, N'-[4-({3-[(4-chlorophenyl)methyl]-1,2,4-thiadiazol-5-yl}oxy-2,5-dimethylphenyl]-N-ethyl-N-methylmethaneimidamide (1202781-91-6)+SX, 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl=methanesulfonate (1360819-11-9)+SX, 4-(2-bromo-4-fluorophenyl)-N-(2-chloro-6-fluorophenyl)-1,3-dimethyl-1H-pyrazole-5-amine (1362477-26-6)+SX, 2,2-dimethyl-9-fluoro-5-(quinolin-3-yl)-2,3-dihydrobenzo[f][1,4]oxazepine (1207749-50-5)+SX, 2-[6-(3-fluoro-4-methoxyphenyl)-5-methylpyridin-2-yl]quinazoline (1257056-97-5)+SX, 5-fluoro-2-[(4-methylphenyl)methoxy]-4-pyrimidineamine (1174376-25-0)+SX, 5-fluoro-4-imino-3-methyl-1-tosyl-3,4-dihydropyrimidine-2 (1H)-one (1616664-98-2)+SX, N'-(2,5-dimethyl-4-phenoxyphenyl)-N-ethyl-N-methyl-methaneimidamide (1052688-31-9)+SX, N'-{4-[(4,5-dichlorothiazol-2-yl)oxy]-2,5-dimethylphenyl}-N-ethyl-N-methyl-methaneimidamide (929908-57-6)+SX, ethyl (2Z)-3-amino-2-cyano-3-phenylacrylate (39491-78-6)+SX, N-{(2-chlorothiazol-5-yl)methyl}-N-ethyl-6-methoxy-3-nitropyridine-2-amine (1446247-98-8)+SX, 1-[2-({[1-(4-chlorophenyl)-1H-pyrazol-3-yl]oxy}methyl)-3-methylphenyl]-4-methyl-5-oxo-4,5-dihydro-1H-tetrazole (1472649-01-6)+SX.

Examples of the combination of the Present active ingredient of the above sub group c-1 and the Present compound:
ethephon+SX, chlormequat+SX, chlormequat-chloride+SX, mepiquat+SX, mepiquat-chloride+SX, Gibberellin A3+SX, abscisic acid+SX, Kinetin+SX, benzyladenine+SX, forchlorfenuron+SX, thidiazuron+SX.

Examples of the combination of the Present active ingredient of the above sub group c-2 and the Present compound:
*Glomus* spp.+SX, *Glomus intraradices*+SX, *Glomus mosseae*+SX, *Glomus aggregatum*+SX, *Glomus etunicatum*+SX.

Examples of the combination of the Present active ingredient of the above sub group c-3 and the Present compound:
*Bradyrhizobium elkani*+SX, *Bradyrhizobium japonicum*+SX, *Bradyrhizobium lupini*+SX, *Rhizobium leguminosarum* bv. *trifolii*+SX, *Rhizobium leguminosarum* bv. *phaseoli*+SX, *Rhizobium leguminosarum* bv. *viciae*+SX, *Sinorhizobium meliloti*+SX, *Rhizobium* spp.+SX.

Examples of the combination of the Present active ingredient of the above sub group d and the Present compound:
benoxacor+SX, cloquintocet-mexyl+SX, cyometrinil+SX, dichlormid+SX, fenchlorazole-ethyl+SX, fenclorim+SX, flurazole+SX, furilazole+SX, mefenpyr-diethyl+SX, MG191 (2-(dichloromethyl)-2-methyl-1,3-dioxolane)+SX, oxabetrinil+SX, allidochlor+SX, isoxadifen-ethyl+SX, cyprosulfamide+SX, fluxofenim+SX, 1,8-naphthalic anhydride+SX, AD-67 (4-(dichloroacetyl)-1-oxa-4-azaspiro [4.5] decane)+SX.

Examples of the combination of the Present active ingredient of the above sub group e and the Present compound:
DMC (1,1-bis(4-chlorophenyl)ethanol)+SX, FDMC (1,1-bis(4-chlorophenyl)-2,2,2-trifluoroethanol)+SX, bucarpolate+SX, N, N-dibutyl-4-chlorobenzenesulfonamide+SX, dietholate+SX, diethylmaleate+SX, 1-dodecyl-1H-imidazole+SX, N-(2-ethylhexyl)-8,9,10-trinorborn-5-ene-2,3-dicarboximide+SX, PSCP (phenylsaligenin cyclic phosphate)+SX, piperonyl butoxide+SX, piperonyl cyclonene+SX, piprotal+SX, propyl isome+S, safroxan+SX, sesamex+SX, sesamolin+SX, sulfoxide+SX, tribufos+SX, TBPT (S, S, S-tributyl phosphorotrithioate)+SX, ETP (1,1,1-trichloro-2,3-expoxypropane)+SX, ETN (1,2-epoxy-1,2,3,4-tetrahydronaphthalene)+SX, TPP (triphenyl phosphate)+SX, Verbutin+SX.

Examples of the harmful arthropods on which the compound of the present invention has efficacies include harmful insects and harmful mites. Specific examples of harmful arthropods include the followings.

Hemiptera Pests:

Delphacidae (for example, *Laodelphax striatellus, Nilaparvata lugens, Sogatella furcifera, Peregrinus maidis, Javesella pellucida, Perkinsiella saccharicida*, or *Tagosodes orizicolus*);

Cicadellidae (for example, *Nephotettix cincticeps, Nephotettix virescens, Nephotettix nigropictus, Recilia dorsalis, Empoasca onukii, Empoasca fabae, Dalbulus maidis*, or *Cofana spectra*);

Cercopidae (for example, *Mahanarva posticata*, or *Mahanarva fimbriolata*);

Aphididae (for example, *Aphis fabae, Aphis glycines, Aphis gossypii, Aphis pomi, Aphis spiraecola, Myzus persicae, Brachycaudus helichrysi, Brevicoryne brassicae*, Rosy apple aphid (*Dysaphis plantaginea*), *Lipaphis erysimi, Macrosiphum euphorbiae, Aulacorthum solani, Nasonovia ribisnigri, Rhopalosiphum padi, Rhopalosiphum maidis, Toxoptera citricidus, Hyalopterus pruni, Melanaphis sacchari, Tetraneura nigriabdominalis, Ceratovacuna lanigera*, or *Eriosoma lanigerum*);

Phylloxeridae (for example, *Daktulosphaira vitifoliae*, Pecan phylloxera (*Phylloxera devastatrix*), Pecan leaf phylloxera (*Phylloxera notabilis*), or Southern pecan leaf phylloxera (*Phylloxera russellae*));

Adelgidae (for example, *Adelges tsugae, Adelges piceae*, or *Aphrastasia pectinatae*);

Pentatomidae (for example, *Scotinophara lurida*, Malayan rice black bug (*Scotinophara coarctata*), *Nezara antennata, Eysarcoris aeneus, Eysarcoris lewisi, Eysarcoris ventralis, Eysarcoris annamita, Halyomorpha halys, Nezara viridula*, Brown stink bug (*Euschistus heros*), Red banded stink bug (*Piezodorus guildinii*), *Oebalus pugnax, Dichelops melacanthus*);

Cydnidae (for example, Borrower brown bug (*Scaptocoris castanea*));

Alydidae (for example, *Riptortus pedestris, Leptocorisa chinensis*, or *Leptocorisa acuta*);

Coreidae (for example, *Cletus punctiger*, or *Leptoglossus australis*);

Lygaeidae (for example, *Caverelius saccharivorus, Togo hemipterus*, or *Blissus leucopterus*);

Miridae (for example, *Trigonotylus caelestialium, Stenotus rubrovittatus, Stenodema calcarata*, or *Lygus lineolaris*);

Aleyrodidae (for example, *Trialeurodes vaporariorum, Bemisia tabaci, Dialeurodes citri, Aleurocanthus spiniferus, Aleurocanthus camelliae*, or *Pealius euryae*);

Diaspididae (for example, *Abgrallaspis cyanophylli, Aonidiella aurantii, Diaspidiotus perniciosus, Pseudaulacaspis pentagona, Unaspis yanonensis*, or *Unaspis citri*);

Coccidae (for example, *Ceroplastes rubens*);

Margarodidae (for example, *Icerya purchasi*, or *Icerya seychellarum*);

Pseudococcidae (for example, *Phenacoccus solani, Phenacoccus solenopsis, Planococcus kraunhiae, Planococcus comstocki, Planococcus citri, Pseudococcus calceolariae, Pseudococcus longispinus*, or *Brevennia rehi*);

Psyllidae (for example, *Diaphorina citri, Trioza erytreae, Cacopsylla pyrisuga, Cacopsylla chinensis, Bactericera cockerelli*, or Pear psylla (*Cacopsylla pyricola*));

Tingidae (for example, *Corythucha ciliata, Corythucha marmorata, Stephanitis nashi*, or *Stephanitis pyrioides*); Cimicidae (for example, *Cimex lectularius*); and Cicadidae (for example, Giant Cicada (*Quesada gigas*)).

Lepidoptera

Crambidae (for example, *Chilo suppressalis*, Darkheaded stem borer (*Chilo polychrysus*), White stem borer (*Scirpophaga innotata*), *Scirpophaga incertulas, Rupela albina, Cnaphalocrocis medinalis, Marasmia patnalis, Marasmia exigua, Notarcha derogata, Ostrinia furnacalis*, European corn borer (*Ostrinia nubilalis*), *Hellula undalis, Herpetograwma luctuosale, Pediasia teterrellus, Nymphula depunctalis*, Sugarcane borer (*Diatraea saccharalis*));

Pyralidae (for example, *Elasmopalpus lignosellus* or *Plodia interpunctella*);

Noctuidae (for example, *Spodoptera litura, Spodoptera exigua, Mythimna separata, Mamestra brassicae, Sesamia inferens, Spodoptera mauritia, Naranga aenescens, Spodoptera frugiperda, Spodoptera exempta, Agrotis ipsilon, Autographa nigrisigna, Plusia festucae*, Soybean looper (*Chrysodeixis includens*), *Trichoplusia* spp., *Heliothis* spp. (for example, *Heliothis virescens*), *Helicoverpa armigera, Helicoverpa* spp. (for example, *Helicoverpa zea*), Velvetbean caterpillar (*Anticarsia gemmatalis*), Cotton leafworm (*Alabama argillacea*), Hop vine borer (*Hydraecia immanis*)), Pieridae (for example, *Pieris rapae*);

Tortricidae (for example, *Grapholita molesta, Grapholita dimorpha, Leguminivora glycinivorella, Matsumuraeses azukivora, Adoxophyes orana fasciata, Adoxophyes honmai, Homona magnanima, Archips fuscocupreanus, Cydia pomonella, Tetramoera schistaceana*, Bean Shoot Borer (*Epinotia aporema*), or Citrus fruit borer (*Ecdytolopha aurantiana*));

Gracillariidae (for example, *Caloptilia theivora*, or *Phyllonorycter ringoniella*);

Carposinidae (for example, *Carposina sasakii*);

Lyonetiidae (for example, Coffee Leaf miner (*Leucoptera coffeela*), *Lyonetia clerkella*, or *Lyonetia prunifoliella*);

Lymantriidae (for example, *Lymantria* spp. (for example, *Lymantria dispar*), or *Euproctis* spp. (for example, *Euproctis pseudoconspersa*));

Pluteliidae (for example, *Plutella xylostella*);

Gelechiidae (for example, *Anarsia lineatella, Helcystogranuna triannulellum, Pectinophora gossypiella, Phthorimaea operculella*, or *Tuta absolut*);

Arctiidae (for example, *Hyphantria cunea*);

Castniidae (for example, Giant Sugarcane borer (*Telchin licus*));

Cossidae (for example, *Cosus insularis*);

Geometridae (for example, *Ascotis selenaria*);

Limacodidae (for example, *Parasa lepida*);

Stathmopodidae (for example, *Stathmopoda masinissa*);

Sphingidae (for example, *Acherontia lachesis*);

Sesiidae (for example, *Nokona feralis*);

Hesperiidae (for example, *Parnara guttata*).

Thysanoptera

Thripidae (for example, *Frankliniella occidentalis, Thrips palmi, Scirtothrips dorsalis, Thrips tabaci, Frankliniella intonsa, Stenchaetothrips biformis*, or *Echinothrips americanus*);

Phlaeothripidae (for example, *Haplothrips aculeatus*).

Diptera

Anthomyiidae (for example, *Delia platura* or *Delia antiqua*);

Ulidiidae (for example, *Tetanops myopaeformis*);

Agromyzidae (for example, *Agromyza oryzae, Liriomyza sativae, Liriomyza trifolii*, or *Chromatomyia horticola*);

Chloropidae (for example, *Chlorops oryzae*);

Tephritidae (for example, *Bactrocera cucurbitae, Bactrocera dorsalis, Bactrocera latifrons, Bactrocera oleae, Bactrocera tryoni*, or *Ceratitis capitata*);

Ephydridae (for example, *Hydrellia griseola, Hydrellia philippina*, or *Hydrellia sasakii*);

Drosophilidae (for example, *Drosophila suzukii*);

Phoridae (for example, *Megaselia spiracularis*);

Psychodidae (for example, *Clogmia albipunctata*);

Sciaridae (for example, *Bradysia difformis*);

Cecidomyiidae (for example, *Mayetiola destructor*, or *Orseolia oryzae*);

Diopsidae (for example, *Diopsis macrophthalma*);

Tipulidae (for example, *Tipula aino*, Common cranefly (*Tipula oleracea*), or European cranefly (*Tipula paludosa*)).

Coleoptera

Chrysomelidae (for example, *Diabrotica virgifera virgifera, Diabrotica undecimpunctata howardi, Diabrotica barberi, Diabrotica virgifera zeae, Diabrotica balteata*, Cucurbit Beetle (*Diabrotica speciosa*), *Cerotoma trifurcata, Oulema melanopus, Aulacophora femoralis, Phyllotreta striolata*, Cabbage flea beetle (*Phyllotreta cruciferae*), Western black flea beetle (*Phyllotreta pusilla*), Cabbage stem flea beetle (*Psylliodes chrysocephala*), *Leptinotarsa decemlineata, Gulema oryzae, Colaspis brunnea, Chaetocnema pulicaria, Chaetocnema confinis, Epitrix cucumeris, Dicladispa armigera*, Grape *Colaspis* (*Colaspis brunnea*), southern corn leaf beetle (*Myochrous denticollis*), *Laccoptera quadrimacu*, or *Epitrix hirtipennis*);

Carabidae (for example, Seedcorn beetle (*Stenolophus lecontei*), or Slender seedcorn beetle (*Clivina impressifrons*));

Scarabaeidae (for example, *Anomala cuprea, Anomala rufocuprea, Anomala albopilosa, Popillia japonica, Heptophylla picea*, European Chafer (*Rhizotrogus majalis*), *Tomarus gibbosus, Holotrichia* spp., or *Phyllophaga* spp. (for example, *Phyllophaga crinita*)), *Diloboderus* spp. (for example, *Diloboderus abderus*));

Curculionidae (*Aracanthus* spp. (for example, *Araecerus coffeae, Cylas formicarius, Euscepes postfasciatus, Hypera postica, Sitophilus zeamais, Echinocnemus squameus, Lissorhoptrus oryzophilus, Rhabdoscelus lineatocollis, Anthonomus grandis, Sphenophorus venatus*, Southern Corn Billbug (*Sphenophorus callosus*), Soybean stalk weevil (*Sternechus subsignatus*), Sgarcane wiivil (*Sphenophorus levis*), *Scepticus griseus, Scepticus uniformis, Zabrotes subfasciatus, Tomicus piniperda*, Coffee Berry Borer (*Hypothenemus hampei*), or *Aracanthus mourei*) or cotton root borer (*Eutinobothrus brasiliensis*);

Tenebrionidae (for example, *Tribolium castaneum*, or *Tribolium confusum*);

Coccinellidae (for example, *Epilachna* vigintioctopunctata);

Bostrychidae (for example, *Lyctus brunneus*);

Ptinidae;

Cerambycidae (for example, *Anoplophora malasiaca*, or *Migdolus fryanus*);

Elateridae (for example, *Melanotus okinawensis, Agriotes fuscicollis, Melanotus legatus, Anchastus* spp., *Conoderus* spp., *Ctenicera* spp., *Limonius* spp., *Aeolus* spp.);

Staphylinidae (for example, *Paederus fuscipes*).

Orthoptera

Acrididae (for example, *Locusta migratoria, Dociostaurus maroccanus, Chortoicetes terminifera, Nomadacris septemfasciata*, Brown Locust (*Locustana pardalina*), Tree Locust (*Anacridium melanorhodon*), Italian Locust (*Calliptamus italicus*), Differential grasshopper (*Melanoplus differentialis*), Two striped grasshopper (*Melanoplus bivittatus*), Migratory grasshopper (*Melanoplus sanguinipes*), Red-Legged grasshopper (*Melanoplus femurrubrum*), Clearwinged grasshopper (*Camnula pellucida*), *Schistocerca gregaria*, Yellow-winged locust (*Gastrimargus musicus*), Spur-throated locust (*Austracris guttulosa*), *Oxya yezoensis, Oxya japonica*, or *Patanga succincta*);

Gryllotalpidae (for example, *Gryllotalpa orientalis*);

Gryllidae (for example, *Acheta domesticus*, or *Teleogryllus emma*);

Tettigoniidae (for example, Mormon cricket (*Anabrus simplex*).

Hymenoptera

Tenthredinidae (for example, *Athalia rosae*, or *Athalia japonica*);

*Solenopsis* spp.;

Formicidae (for example, Brown leaf-cutting ant (*Atta capiguara*)).

Blattodea

Blattellidae (for example, *Blattella germanica*);

Blattidae (for example, *Periplaneta fuliginosa, Periplaneta americana, Periplaneta brunnea*, or *Blatta orientalis*);

Termitidae (for example, *Reticulitermes speratus, Coptotermes formosanus, Incisitermes minor, Cryptoternes dornesticus, Odontotermes formosanus, Neotermes koshunensis, Glyptotermes satsumensis, Glyptotermes nakajimai, Glyptotermes fuscus, Hodotermopsis sjostedti, Coptotermes guangzhouensis, Reticulitermes amamianus, Reticulitermes miyatakei, Reticulitermes kanmonensis, Nasutitermes takasagoensis, Pericapritermes nitobei, Sinocapritermes mushae*, or *Cornitermes cumulans*).

Acari

Tetranychidae (for example, *Tetranychus urticae, Tetranychus kanzawai, Tetranychus evansi, Panonychus citri, Panonychus ulmi*, or *Oligonychus* spp.);

Eriophyidae (for example, *Aculops pelekassi, Phyllocoptruta citri, Aculops lycopersici, Calacarus carinatus, Acaphylla theavagrans, Eriophyes chibaensis, Aculus schlechtendali, Aceria diospyri, Aceria tosichella*, or *Shevtchenkella* sp.);

Tarsonemidae (for example, *Polyphagotarsonemus latus*);

Tenuipalpidae (for example, *Brevipalpus phoenicis*);

Tuckerellidae;

Ixodidae (for example, *Haemaphysalis longicornis, Haemaphysalis flava, Dermacentor taiwanensis, Dermacentor variabilis, Ixodes ovatus, Ixodes persulcatus, Ixodes scapularis, Amblyomma americanum, Boophilus microplus*, or *Rhipicephalus sanguineus*);

Acaridae (for example, *Tyrophagus putrescentiae*, or *Tyrophagus similis*);

Pyroglyphidae (for example, *Dermatophagoides farinae*, or *Dermatophagoides pteronyssinus*);

Cheyletidae (for example, *Cheyletus eruditus, Cheyletus malaccensis, Cheyletus moorei*, or *Cheyletiella yasguri*);

Sarcoptidae (for example, *Otodectes cynotis*, or *Sarcoptes scabiei*);

Demodicidae (for example, *Demodex canis*);

Listrophoridae;

Haplochthoniidae;

Macronyssidae (for example, *Ornithonyssus bacoti*, or *Ornithonyssus sylviarum*);

Dermanyssidae (for example, *Dermanyssus gallinae*);

Trombiculidae (for example, *Leptotrombidium akamushi*).

The composition for controlling harmful arthropods of the present invention comprises the compound of the present invention and an inert active carrier. The composition for controlling harmful arthropods of the present invention is usually prepared by mixing the compound of the present invention with an inert active carrier such as solid carrier, liquid carrier or gaseous carrier, and if necessary, adding surfactants and the other auxiliary agents for formulation, to formulate into emulsifiable concentrates, oil solutions, dust formulations, granules, wettable powders, flowables, microcapsules, aerosols, smoking agents, poison baits, resin formulations, shampoo formulations, paste-like formulations, foams, carbon dioxide formulations and tablets and the others. Such formulations may be processed into mosquito repellent coils, electric mosquito repellent mats, liquid mosquito formulations, smoking agents, fumigants, sheet formulations, spot-on formulations or formulations for oral treatment.

The composition for controlling harmful arthropods of the present invention comprises usually 0.01 to 95% by weight of the compound of the present invention based on the total weights of the composition for controlling harmful arthropods.

Examples of the solid carrier to be used in the formulation include fine powders or granules of clays (for example, kaolin clay, diatomaceous earth, bentonite, Fubasami clay, or acid white clay), dry silica, wet silica, talcs, ceramics, other inorganic minerals (for example, sericite, quartz, sulfur, active carbon, or calcium carbonate) or chemical fertilizers (for example, ammonium sulfate, ammonium phosphate, ammonium nitrate, urea or ammonium chloride) and the others; as well as synthetic resins (for example, polyester resins such as polypropylene, polyacrylonitrile, polymethylmethacrylate and polyethylene terephthalate; nylon resins (for example, nylon-6, nylon-11 and nylon-66); polyamide resins; polyvinyl chloride, polyvinylidene chloride, vinyl chloride-propylene copolymers, and the others).

Examples of the above-mentioned liquid carriers include water; alcohols (for example, methanol, ethanol, isopropyl alcohol, butanol, hexanol, benzyl alcohol, ethylene glycol, propylene glycol or phenoxy ethanol); ketones (for example, acetone, methyl ethyl ketone or cyclohexanone); aromatic hydrocarbons (for example, toluene, xylene, ethyl benzene, dodecyl benzene, phenyl xylyl ethane or methylnaphthalene); aliphatic hydrocarbons (for example, hexane, cyclohexane, kerosene or light oil); esters (for example, ethyl acetate, butyl acetate, isopropyl myristate, ethyl oleate, diisopropyl adipate, diisobutyl adipate or propylene glycol monomethyl ether acetate); nitriles (for example, acetonitrile or isobutyronitrile); ethers (for example, diisopropyl ether, 1,4-dioxane, 1,2-dimethoxyethane, diethyleneglycol dimethyl ether, diethylene glycol monomethyl ether, propylene glycol monomethyl ether, dipropylene glycol monomethyl ether, or 3-methoxy-3-methyl-1-butanol); amides (for example, dimethylformamide (hereinafter, referred to as DMF), dimethylacetamide); sulfoxides (for example, DMSO); propylene carbonate; and vegetable oils (for example, soybean oil or cottonseed oil).

Examples of the above-mentioned gaseous carrier include fluorocarbon, butane gas, liquefied petroleum gas (LPG), dimethyl ether, and carbon dioxide gas.

Examples of the surfactants include nonionic surfactants such as polyoxyethylenated alkyl ethers, polyoxyethylenated alkyl aryl ethers and polyethylene glycol fatty acid esters; and anionic surfactants such as alkyl sulfonates, alkylbenzene sulfonates and alkyl sulfates.

Examples of the other auxiliary agents for formulation include a binder, a dispersant, a colorant and a stabilizer. Specific examples include casein, gelatin, polysaccharides (for example, starch, gum arable, cellulose derivatives and alginic acid), lignin derivatives, bentonite, water-soluble synthetic polymers (for example, polyvinyl alcohol, polyvinyl pyrrolidone and polyacrylic acids), acidic isopropyl phosphate, 2,6-di-tert-butyl-4-methylphenol, and a mixture of 2-tert-butyl-4-methoxyphenol and 3-tert-butyl-4-methoxyphenol.

Examples of base material of the resin formulation include polyvinyl chloride polymers, polyurethane and the others, and a plasticizer such as phthalate esters (for example, dimethyl phthalate, dioctyl phthalate), adipic acid esters and stearic acid may be added to these base materials, if necessary. The resin formulation can be prepared by mixing the compound of the present invention with the above-mentioned base material, kneading the mixture with a usually kneader, followed by molding it by injection molding, extrusion molding or pressure molding and the like. The resultant resin formulation can be subjected to further molding or cutting procedure and the like, if necessary, to be processed into shapes such as a plate, film, tape, net or string shape. These resin formulations can be processed into animal collars, animal ear tags, sheet products, trap strings, gardening supports and other products.

Examples of a base material for the poison baits include bait ingredients such as grain powder, vegetable oil, saccharide and crystalline cellulose, and if necessary, with addition of antioxidants such as dibutylhydroxytoluene and nordihydroguaiaretic acid, preservatives such as dehydroacetic acid, accidental ingestion inhibitors for children and pets such as a chili powder, and insect attraction fragrances such as cheese flavor, onion flavor and peanut oil.

The method for controlling harmful arthropods of the present invention is conducted by applying an effective amount of the compound of the present invention to a harmful arthropod directly and/or a habitat thereof (for example, plant bodies, soil, an interior of a house, animal bodies). In the method for controlling harmful arthropods of the present invention, the Present compound is usually used in the form of a harmful arthropod controlling composition.

When a composition for controlling harmful arthropods of the present invention is used for controlling harmful arthropods in an agricultural field, the application dose as an amount of the compound of the present invention is usually within a range from 1 to 10,000 g per 10,000 m$^2$. When a composition for controlling harmful arthropods of the present invention is formulated into an emulsifiable concentrate, a wettable powder, or a flowable formulation etc., the composition is usually applied by diluting it with water in such a way that a concentration of the compound of the present invention is within a range from 0.01 to 10,000 pm. The granular formulation, or the dust formulation etc., is usually applied as itself without diluting it.

These formulations or an aqueous dilution thereof can be spared directly to harmful arthropods or plants (such as crops) to be protected from harmful arthropods, and also may be applied to the soil of crop land in order to control harmful arthropods which live there.

Also, the resin preparation which is processed into a sheet or a string may be applied by winding a plant with a sheet or a string of the resin preparation, putting a string of the resin preparation around a crop so that the plant is surrounded by the string, or laying a sheet of the resin preparation on the soil surface near the root of a plant.

When the composition for controlling harmful arthropods of the present invention is used to control harmful arthropods that live inside a house, the application dose as an amount of the present compound is usually within a range from 0.01 to 1,000 mg per 1 m$^2$ of an area to be treated, in the case of using it on a planar area. In the case of using it spatially, the application dose as an amount of the present compound is usually within a range from 0.01 to 500 mg per 1 m$^3$ of the space to be treated. When the composition for controlling harmful arthropods of the present invention is formulated into emulsifiable concentrates, wettable powders, flowables or the others, such formulations are usually applied after diluting it with water in such a way that a concentration of the active ingredient is within a range from 0.1 to 10,000 ppm, and then sparging it. In the case of being formulated into oil solutions, aerosols, smoking agents, poison baits and the others, such formulations are used as itself without diluting it.

When the composition for controlling harmful arthropods of the present invention is used for controlling external parasites of livestock such as cows, horses, pigs, sheep, goats and chickens and small animals such as dogs, cats, rats and mice, the composition of the present invention can be applied to the animals by a known method in the veterinary field. Specifically, when systemic control is intended, the control composition of the present invention is administered to the animals as a tablet, a mixture with feed or a suppository, or by injection (including intramuscular, subcutaneous, intravenous and intraperitoneal injections). On the other hand, when non-systemic control is intended, the composition of the present invention is applied to the animals by means of spraying of the oil solution or aqueous solution, pour-on or spot-on treatment, or washing the animal with a shampoo formulation, or by putting a collar or ear tag made of the resin formulations to the animal. In the case of administering to an animal body, the dose of the Present compound is usually within a range from 0.1 to 1,000 mg per 1 kg of an animal body weight.

EXAMPLES

Hereinafter, the present invention is explained in more detail by using Preparation example, Formulation example, and Test example, however, the present invention should not be limited to these examples.

Firstly, the preparation example of the compound of the present invention is shown.

Reference Preparation Example 1

A mixture of 6-chloro-3-(ethanesulfonyl)-5-(trifluorophenyl)-5'-(2,2,3,3,3-pentafluoropropoxy)-2,2'-bipyirine 500 mg and 28% ammonia water 3 mL was stirred at 100° C. for 5 hours. To the resulting mixture was added water at room temperature, and the mixture was extracted with ethyl acetate. The resulting organic layers were washed with saturated brine, dried over anhydrous sodium sulfate, and concentrated under reduced pressure. The resulting residue was subjected to a silica gel column chromatography to obtain the intermediate compound (1) represented by the following formula 401 mg.

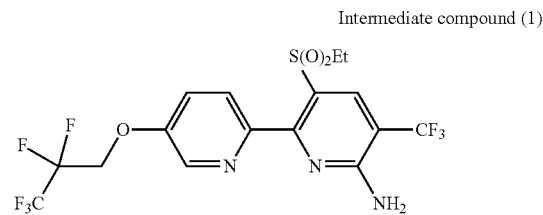

Intermediate compound (1)

$^1$H-NMR (CDCl$_3$) δ: 8.44 (1H, s), 8.35 (1H, s), 7.78 (1H, d), 7.39 (1H, d), 5.52 (2H, s), 4.53 (2H, t), 3.79 (2H, q), 1.37 (3H, t).

Reference Preparation Example 2-1

A mixture of 6-chloro-3-(ethanesulfonyl)-5'-(2,2,3,3,3-pentafluoropropoxy)-2,2'-bipyirine 600 mg, 20 hydrazine monohydrate 219 mg, diethylisopropylamine 180 mg, and THF 2 mL was stirred under reflux for 10 hours. To the resulting mixture was added water at room temperature, and the mixture was extracted with ethyl acetate. The resulting organic layers were washed with saturated brine, dried over anhydrous sodium sulfate, and concentrated under reduced pressure. The resulting residue was recrystallized from ethyl acetate and hexane to obtain the intermediate compound (2) represented by the following formula 465 mg.

Intermediate compound (2)

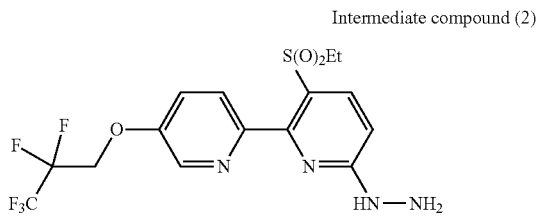

¹H-NMR (CDCl₃) δ: 8.34 (1H, d), 8.17 (1H, d), 7.70 (1H, d), 7.37 (1H, dd), 6.89 (1H, d), 6.40 (1H, s), 4.52 (2H, t), 3.93 (2H, s), 3.66 (2H, q), 1.32 (3H, t).

Reference Preparation Example 2-2

The compound which was prepared according to the method described in the Reference Preparation Example 2-1, and its physical property values are shown below.

Intermediate compound (3)

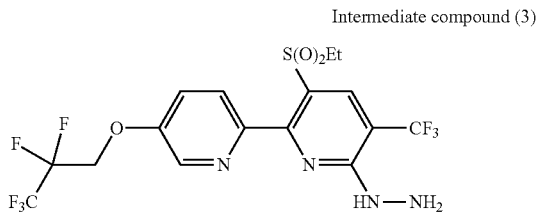

¹H-NMR (CDCl₃) δ: 8.40 (1H, s), 8.37 (1H, d), 7.82 (1H, d), 7.41 (1H, dd), 6.74 (1H, s), 4.55 (2H, t), 4.19 (2H, d), 3.80 (2H, q), 1.37 (3H, t).

Preparation Example 1

A mixture of the intermediate compound (2) 185 mg, 1,1'-carbonyldiimidazole 81 mg and NMP 2 mL was stirred at room temperature for 2 hours. To the resulting mixture was added water at room temperature, and the mixture was extracted with ethyl acetate. The resulting organic layers were washed with saturated brine, dried over anhydrous sodium sulfate, and concentrated under reduced pressure. The resulting residue was subjected to a silica gel column chromatography to obtain the present compound 1 represented by the following formula 171 mg.

Present compound 1

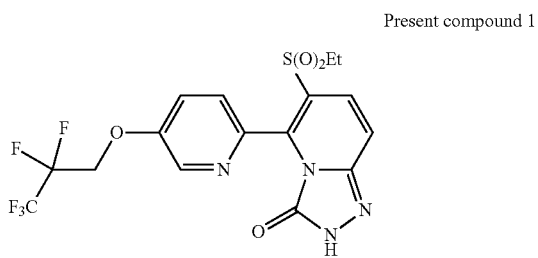

¹H-NMR (CDCl₃) δ: 10.17 (1H, s), 8.38 (1H, d), 7.59 (1H, d), 7.56 (1H, d), 7.36 (1H, dd), 7.22 (1H, d), 4.55 (2H, t), 3.15 (2H, q), 1.28 (3H, t).

Preparation Example 2

The compound which was prepared according to the method described in the Preparation Example 1, and its physical property values are shown below.

Present compound 2

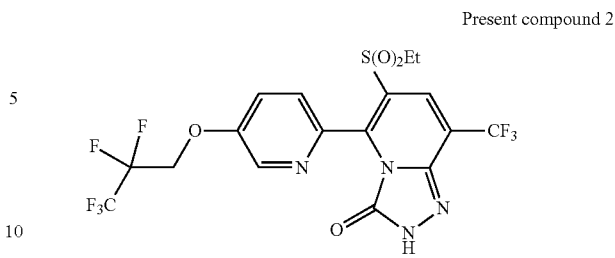

¹H-NMR (CDCl₃) δ: 10.59 (1H, s), 8.40 (1H, d), 7.95 (1H, s), 7.57 (1H, d), 7.38 (1H, dd), 4.57 (2H, t), 3.22-3.17 (2H, m), 1.29 (3H, t).

Preparation Example 3

A mixture of the intermediate compound (3) 247 mg, trimethyl orthoformate 5 mL and trifluoroacetic acid 57 µL was stirred at 110° C. for 3 hours. To the resulting mixture was added water at room temperature, and the mixture was exacted with ethyl acetate. The resulting organic layers were washed with saturated brine, dried over anhydrous sodium sulfate, and concentrated under reduced pressure. The resulting residue was subjected to a silica gel column chromatography (hexane:ethyl acetate=1:1) to obtain the present compound 3 represented by the following formula 249 mg.

Present compound 3

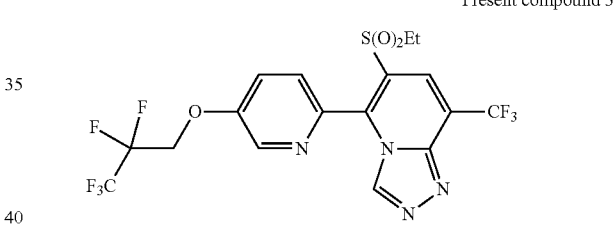

¹H-NMR (CDCl₃) δ: 8.59 (1H, dd), 8.49 (1H, s), 8.26 (1H, d), 7.76 (1H, dd), 7.56 (1H, dd), 4.63 (2H, t), 3.23 (2H, q), 1.31 (3H, t).

Preparation Example 4

The compound which was prepared according to the method described in the Preparation Example 3, and its physical property values are shown below.

Present compound 4

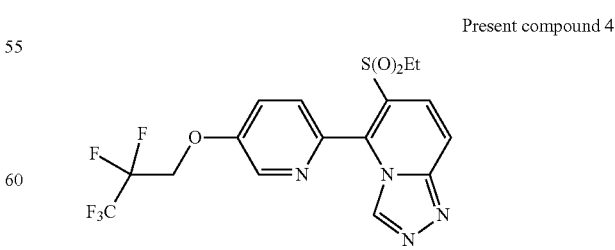

¹H-NMR (CDCl₃) δ: 8.57 (1H, dd), 8.39 (1H, d), 7.98 (1H, dd), 7.90 (1H, d), 7.73 (1H, dd), 7.54 (1H, dd), 4.62 (2H, td), 3.19 (2H, q), 1.28 (3H, t).

Preparation Example 5

A mixture of the intermediate compound (1) 300 mg, 2-chloroethylamine hydrochloride salt 105 mg, diethylisopropylamine 310 μL and NMP 2 mL was stirred at 120° C. for 7 hours. To the resulting mixture was added water at room temperature, and the mixture was extracted with ethyl acetate. The resulting organic layers were washed with saturated brine, dried over anhydrous sodium sulfate, and concentrated under reduced pressure. The resulting residue was subjected to a silica gel column chromatography (hexane:ethyl acetate=1:1) to obtain the present compound 5 represented by the following formula 138 mg.

Present compound 5

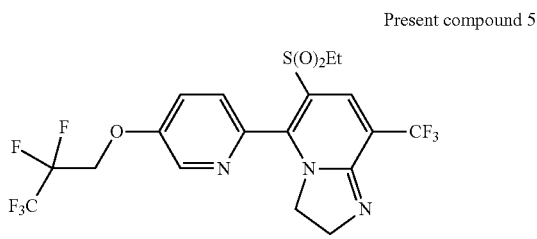

$^1$H-NMR (CDCl$_3$) δ: 8.43 (1H, d), 7.74 (1H, d), 7.53 (1H, d), 7.41 (1H, dd), 4.54 (2H, t), 4.08-4.03 (2H, m), 3.61 (2H, d), 2.93 (2H, q), 1.25 (3H, t).

Preparation Example 6

A mixture of the intermediate compound (1) 300 mg, 2-chloroacetaldehyde 1.05 g, and NMP 2 mL was stirred at 120° C. for 7 hours. To the resulting mixture was added water at room temperature, and the mixture was extracted with ethyl acetate. The resulting organic layers were washed with saturated brine, dried over anhydrous sodium sulfate, and concentrated under reduced pressure. The resulting residue was subjected to a silica gel column chromatography (hexane:ethyl acetate=2:1) to obtain the present compound 6 represented by the following formula 200 mg.

Present compound 6

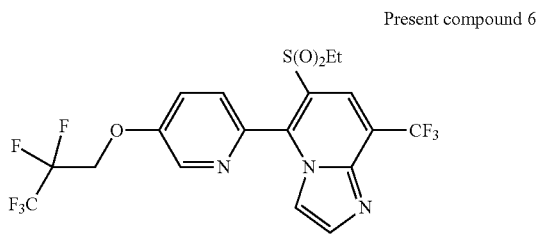

$^1$H-NMR (CDCl$_3$) δ: 8.56 (1H, d), 8.20 (1H, s), 7.84 (1H, d), 7.67 (1H, d), 7.53 (1H, dd), 7.20 (1H, d), 4.61 (2H, t), 3.25-3.21 (2H, m), 1.29 (3H, t).

Next, the formulation examples of the Present compound are shown below. The "parts" represents "part by weight" unless otherwise specified.

Formulation Example 1

Into a mixture of 35 parts of xylene and 35 parts of DMF, 10 parts of any one of the Present compounds 1 to 6 is dissolved, and then 14 parts of polyoxyethylene styryl phenyl ether and 6 parts of calcium dodecylbenzene sulfonate are added, followed by mixing them to obtain each formulation.

Formulation Example 2

Four(4) parts of sodium lauryl sulfate, 2 parts of calcium lignin sulfonate, 20 parts of synthetic hydrated silicon oxide fine powder and 54 parts of diatomaceous earth are mixed, and further 20 parts of any one of the Present compounds 1 to 6 is added, followed by mixing them to obtain each wettable powders.

Formulation Example 3

To 2 parts of any one of the Present compounds 1 to 6, 1 part of synthetic hydrated silicon oxide fine powder, 2 parts of calcium lignin sulfonate, 30 parts of bentonite and 65 parts of kaolin clay are added, followed by mixing, granulation with a granulator and forced-air drying to obtain each granular formulation.

Formulation Example 4

Into an appropriate amount of acetone, 1 part of any one of the Present compounds 1 to 6 is mixed, and then 5 parts of synthetic hydrous silicon oxide fine powder, 0.3 parts of isopropyl acid phosphate and 93.7 parts of kaolin clay are added, followed by mixing with stirring thoroughly and removal of acetone from the mixture by evaporation to obtain each of powder formulation.

Formulation Example 5

A mixture of 35 parts of polyoxyethylene alkyl ether sulfate ammonium salt and white carbon (weight ratio of 1:1), 20 parts of any one of the Present compounds 1 to 6, and 45 parts of water are mixed, followed by finely grounding by a wet grinding method to obtain each flowable formulation.

Formulation Example 6

Into a mixture of 5 parts of xylene and 5 parts of trichloroethane, 0.1 parts of any one of the Present compounds 1 to 6 is dissolved, and the resulting mixture is then mixed with 89.9 parts of kerosene to obtain each oil solution.

Formulation Example 7

Into 0.5 mL of acetone, 10 mg of any one of the Present compounds 1 to 6 is dissolved and the solution is added dropwise to 5 g of a solid feed powder for an animal (solid feed powder for rearing and breeding CE-2, manufactured by CLEA Japan, Inc.), followed by mixing the resulting mixture uniformly, and then by drying them by evaporation of acetone to obtain each poison bait.

Formulation Example 8

Into an aerosol can, 0.1 part of any one of the Present compounds 1 to 6 and 49.9 parts of Neothiozole (Chuo Kasei Co., Ltd.) are placed. After mounting an aerosol valve, 25 parts of dime thy lether and 25 parts of LPG are filled, followed by shaking and further mounting an actuator to obtain an oily aerosol.

Formulation Example 9

A mixture of 0.6 part of any one of the Present compounds 1 to 6, 0.01 part of BBT (2,6-di-tert-butyl-4-methylphenol), 5 parts of xylene, 3.39 parts of deodorized kerosine and 1 part of an emulsifier {Rheodol MO-60 (registered trademark of Kao Corporation)} and 50 parts of distilled water are filled into an aerosol container, and a valve part is attached. Then, 40 parts of a propellant (LPG) is filled therein through the valve under pressure to obtain an aqueous aerosol.

Formulation Example 10

Zero point one (0.1) parts of any one of the Present compounds 1 to 6 are mixed into 2 mL of propylene glycol, and the resulting solution is impregnated into a ceramic plate having a size of 4.0 cm×4.0 cm and a thickness of 1.2 cm, to obtain thermal fumigants.

Formulation Example 11

Five(5) parts of any one of the Present compounds 1 to 6, and 95 parts of ethylene-methyl methacrylate copolymer (the ratio of the methyl methacrylate in the copolymer: 10 weight %), Acryft (registered by trademark) WD 301, manufactured by Sumitomo Chemical Co. Ltd.) are melted and kneaded with a closed type pressure kneader (manufactured by Moriyama Manufacturing Co. Ltd.), and the resulting kneaded product is extruded from an extrusion molding machine through a molding die to obtain a rod-shaped molded product having a length of 15 cm and a diameter of 3 mm.

Formulation Example 12

Five(5) parts of any one of the Present compounds 1 to 6, and 95 parts of plasticized polyvinyl chloride resin are melted and kneaded with a closed type pressure kneader (manufactured by Moriyama Manufacturing Co. Ltd.), and the resulting kneaded product is extruded from an extrusion molding machine through a molding die to obtain a rod-shaped molded product having a length of 15 cm and a diameter of 3 mm.

Formulation Example 13

One hundred(100) mg of any one of the Present compounds 1 to 6, 68.75 mg of lactose, 237.5 mg of corn starch, 43.75 mg of microcrystalline cellulose, 18.75 mg of polyvinylpyrrolidone, 28.75 mg of sodium carbomethyl starch and 2.5 mg of magnesium stearate are mixed, and the resulting mixture was compressed to an appropriate size to obtain a tablet.

Formulation Example 14

Twenty-five(25) mg of any one of the Present compounds 1 to 6, 60 mg of lactose, 25 mg of corn starch, 6 mg of carmellose calcium and an appropriate amount of 5% of hydroxypropyl methylcellulose are mixed, and the resulting mixture are filled into a hard shell gelatin capsule or a hydroxypropyl methylcellulose capsule to obtain capsules.

Formulation Example 15

To 100 mg of any one of the Present compounds 1 to 6, 500 mg of fumaric acid, 2000 mg of sodium chloride, 150 mg of methyl paraben, 50 mg of propyl paraben, 25000 mg of granulated sugar, 13,000 mg of sorbitol (70% solution), 100 mg of Veegum K (manufactured by Vanderbilt Co.), 35 mg of perfume and 500 mg of coloring agent, a distilled water is added so that a final volume is set to be 100 mL, followed by mixing them to obtain a suspension for oral administration.

Formulation Example 16

Into a mixture of 5% by weight of an emulsifier, 3% by weight of benzyl alcohol and 30% by weight of propylene glycol, 5% by weight of any one of the Present compounds 1 to 6 is dissolved, and phosphate buffer is added thereto so that a pH of the solution is set to be 6.0 to 6.5, and water is added as the rest parts to obtain the solution for oral administration.

Formulation Example 17

To a mixture of 51% by weight of fractional distillated palm oil and 3% by weight of polysorbate 85, 5% by weight of aluminum distearate is added, and heated to disperse it. The resulting mixture is cooled to room temperature, and 25% by weight of saccharin is dispersed in an oil vehicle. 10% by weight of any one of the Present compounds 1 to 6 is divided thereto to obtain a paste for oral administration.

Formulation Example 18

Five(5) % by weight of any one of the Present compounds 1 to 6 is mixed with 95% by weight of limestone filler, followed by a wet granulation of the resulting mixture to obtain a granule for oral administration.

Formulation Example 19

Into 80 parts of diethylene glycol monomethyl ether, 5 parts of any one of the Present compounds 1 to 6 is dissolved, and 15 parts of propylene carbonate is added thereto, and the resulting mixture is mixed to obtain a spot-on solution.

Formulation Example 20

Into 70 parts of diethylene glycol monomethyl ether, 10 parts of any one of the Present compounds 1 to 6 is dissolved, and 20 parts of 2-octyldodecanol is added thereto, and the resulting mixture is mixed to obtain a pour-on solution.

Formulation Example 21

To 0.5 parts of any one of the Present compounds 1 to 6, 60 parts of Nikkol (registered by trademark) TEALS-42 (manufactured by Nikko Chemical Co. Ltd.: 42% of aqueous solution of lauryl sulfuric acid triethanol amine) and 20 parts of propylene glycol are added, and the resulting mixture is mixed with stirring thoroughly, and 19.5 parts of water is then added thereto and the resulting mixture is further mixed with stirring thoroughly to obtain a hydrogenous solution of shampoo formulation.

Formulation Example 22

Zero point one five(0.15)% by weight of any one of the Present compounds 1 to 6, 95% by weight of animal feed, as well as 4.85% by weight of a mixture of dibasic calcium phosphate, diatomaceous earth, aerosol and carbonate (or chalk) are mixed with stirring thoroughly to obtain a premix for animal feed.

Formulation Example 23

Seven point two (7.2) g of any one of the Present compounds 1 to 6, and 92.8 g of Hosco (registered trademark)S-55 (manufactured by Maruishi Pharmaceuticals) are melted and mixed at 100° C., and the resulting mixture was poured into a suppository mold, followed by performing a cooling solidification to obtain a suppository.

Next, Test Examples are used to show an efficacy of the present compound on controlling harmful arthropods.

The following test examples were carried out at 25° C.

Test Example 1

The test compounds was made to a formulation according to the method described in the Formulation Example 5, and thereto was added water containing 0.03 v/v % of a spreader to prepare a diluted solution containing a prescribed concentration of the test compound.

Cucumber (*Cucumis sativus*) seedling (on the developmental stage of the second true leaf) was planted in a container and approximately 30 of cotton aphid (*Aphis gossypii*) (all stages of life) were released onto the leaves of the cucumber. After 1 day, the diluted solutions were sprayed into the seedling in a ratio of 10 mL/seedling. After 5 days, the number of the surviving insects was examined and the controlling value was calculated by the following equation.

Controlling value (%)=$\{1-(Cb \times Tai)/(Cai \times Tb)\}*100$ wherein the symbols in the formula represent the following descriptions.

Cb: Number of the test insects in untreated group;
Cai: Number of the surviving insects at the time of the investigation in untreated group;
Tb: Number of the test insects in treated group;
Tai: Number of the surviving insects at the time of the investigation in treated group;

Here the "untreated group" represents a group where a similar treatment procedure to that of the treated group except not using the test compound is done.

The test was conducted by making the prescribed concentration 500 ppm and using the below-mentioned present compounds as a test compound according to the test example 1. As a result of the test, the below-mentioned present compounds showed 90% or greater as the controlling value.

Present compound(s); 1, 2, 3, 4, 5, and 6

The test was conducted by making the prescribed concentration 200 ppm and using the below-mentioned present compounds as a test compound according to the test example 1. As a result of the test, the below-mentioned present compounds showed 90% or greater as the controlling value.

Present compound(s): 1, 2, 3, 4, 5 and 6

Test Example 2

The test compounds were made to a formulation according to the method described in the Formulation Example 5, and thereto was added water to prepare a diluted solution containing a prescribed concentration of the test compound.

Cucumber seedling (on the developmental stage of the second true leaf) was planted in a container, and the diluted solutions in the ratio on 5 mL/seedling were irrigated into the plant foot. After 7 days, approximately 30 of cotton aphid (all stages of life) were inoculated onto the cucumber leaves. After additional 6 days, the number of the surviving insects was examined, and the controlling value was calculated by the following equation.

Controlling value (%)=$\{1-(Cb \times Tai)/(Cai \times Tb)\}*100$ wherein the symbols in the formula represent the following descriptions.

Cb: Number of the test insects in untreated group;
Cai: Number of the surviving insects at the time of the investigation in untreated group;
Tb: Number of the test insects in treated group;
Tai: Number of the surviving insects at the time of the investigation in treated group;

Here the "untreated group" represents a group where a similar treatment procedure to that of the treated group except not using the test compound is done.

The test was conducted by making the prescribed concentration 1,000 ppm and using the below-mentioned present compounds as a test compound according to the test example 2. As a result of the test, the below-mentioned present compound showed 90% or greater as the controlling value.

Present compound(s): 4

Test Example 3

The test compounds were made to a formulation according to the method described in the Formulation Example 5, and thereto was added water containing 0.03 v/v % of a spreader to prepare a diluted solution containing a prescribed concentration of the test compound.

Rice (*Oryza sativa*) seedling (on the developmental stage of the second true leaf) was planted in a container, and the diluted solutions were sprayed into the seedling in a ratio of 10 mL/seedling. Thereafter, 20 of 3rd instar larvae of brown planthopper (*Nilaparvata lugens*) were released onto the rice leaves. After 6 days, the number of the surviving insects was examined, and the mortality was calculated by the following equation.

Mortality (%)=$\{1-\text{the number of the surviving insects}/20\} \times 100$

The test was conducted by making the prescribed concentration 500 ppm and using the below-mentioned present compounds as a test compound according to the test example 3. As a result of the test, the below-mentioned present compound showed 90% or greater as the controlling value.

Present compound(s): 4

Test Example 4

The test compounds were made to a formulation according to the method described in the Formulation Example 5, and thereto was added water to prepare a diluted solution containing a prescribed concentration of the test compound.

Rice (*Oryza sativa*) seedling (on the developmental stage of the second true leaf) was planted in a container, and the diluted solutions were sprayed into the seedling in a ratio of 10 mL/seedling. To the container was added the diluted solution, and in the container, the rice seedling (on the developmental stage of the second true leaf) which was planted in a container with holes in a bottom face thereof was accommodated. After 7 days, 20 of 3rd instar larvae of brown planthopper (*Nilaparvata lugens*) were released onto the rice leaves. After 6 days, the number of the surviving insects was examined, and the mortality was calculated by the following equation.

Mortality (%)={1−the number of the surviving insects/20}×100

Test Example 5

The test compounds were made to a formulation according to the method described in the Formulation Example 5, and thereto was is water to prepare a diluted solution containing a prescribed concentration of the test compound.

In a container, 7.7 g of artificial diet (Insecta LF, manufactured by NOSAN CORPORATION) was placed, and 2 mL of the diluted solution was irrigated thereto. Five(5) fourth instar larvae of tobacco cutworm (*Spodoptera litura*) were released onto the artificial diet. After 5 days, the number of the surviving insects was examined, and the mortality of insects was calculated by the following equation.

Mortality (%)={1−the number of the surviving insects/5}×100

The test was conducted by making the prescribed concentration 500 ppm and using the below-mentioned present compounds as a test compound according to the test example 5. As a result of the test, the below-mentioned present compounds showed 80% or greater as the mortality.
Present compound(s): 3 and 6

Test Example 6

The test compounds was made to a formulation according to the method described in the Formulation Example 5, and thereto was added water containing 0.03 v/v % of a spreader to prepare a diluted solution containing a prescribed concentration of the test compound.

The diluted solutions were sprayed into the cabbage (*Brassicae oleracea*) seedling (on the developmental stage of the second to third true leaf) that was planted in a container in a ratio of 20 mL/seedling. Thereafter, the stem and leaf thereof was cut out and was then installed into the container that was covered with the filter paper. Five (5) cabbage moth (*Plutella xylostella*) at the second instar larval stages were released into the cup. After 5 days, the number of the surviving insects was counted, and the mortality of insects was calculated by the following equation.

Mortality (%)={1−the number of the surviving insects/5}×100

The test was conducted by making the prescribed concentration 500 ppm and using the below-mentioned present compounds as a test compound according to the test example 5. As a result of the test, the below-mentioned present compounds showed 80% or greater as the mortality.
Present compound(s): 1, 4 and 6

Test Example 7

The test compounds was made to a formulation according to the method described in the Formulation Example 5, and thereto was added water containing 0.03 v/v % of a spreader to prepare a diluted solution containing a prescribed concentration of the test compound.

The diluted solutions were sprayed into the cabbage seedling (on the developmental stage of the third to fourth true leaf) that was planted in a container in a ratio of 20 mL/seedling. Thereafter, ten(10) cabbage moth (*Plutella xylostella*) at the third instar larval stages were released into the cup. After 5 days, the number of the surviving insects was counted, and the mortality of insects was calculated by the following equation.

Mortality (%)={1−the number of the surviving insects/10}×100

The test was conducted by making the prescribed concentration 200 ppm and using the below-mentioned present compounds as a test compound according to the test example 7. As a result of the test, the below-mentioned present compounds showed 90% or greater as the mortality.
Present compound(s): 2, 3, 5 and 6

Test Example 8

The test compounds were dissolved into a mixed solution of polyoxyethylene sorbitan mono-cocoate and acetone (acetone and polyoxyethylene sorbitan mono-cocoate=5:95 (v/v ratio)) in a ratio of 50 µL of the mixed solution per 1 mg of the test compound. Thereto was added water containing 0.03% by volume of a spreader to prepare a diluted solution containing a prescribed concentration of the test compound.

Corns (*Zea mays*) were sown on a tray overlaid with damped KimWipes (Registered trademark). After corns were grown for 5 days, the entire seedling of the corn was immersed into the diluted solution for 30 seconds. Thereafter, each two grains of the seedling were installed in a plastic petri dish (90 mm radius), and 10 western corn rootworms (*Diabrotica virgifera virgifera*) at the second instar larval stages were released onto the cup. After 5 days, the number of the died insects was counted, and the mortality of insects was calculated by the following equation.

Mortality (%)={1−the number of the surviving insects/10}×100

The test was conducted by making the prescribed concentration 500 ppm and using the below-mentioned present compounds as a test compound according to the test example 8. As a result of the test, the below-mentioned present compounds showed 80% or greater as the mortality.
Present compound(s): 1, 3, 4, 5 and 6

INDUSTRIAL APPLICABILITY

The present compound shows an excellent control effect against a harmful arthropod.

The invention claimed is:
1. A compound represented by formula (I):

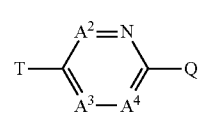

(I)

wherein:
Q represents a group represented by the following formula Q1, a group represented by the following formula Q2, a group represented by the following formula Q3, or a group represented by the following formula Q4:

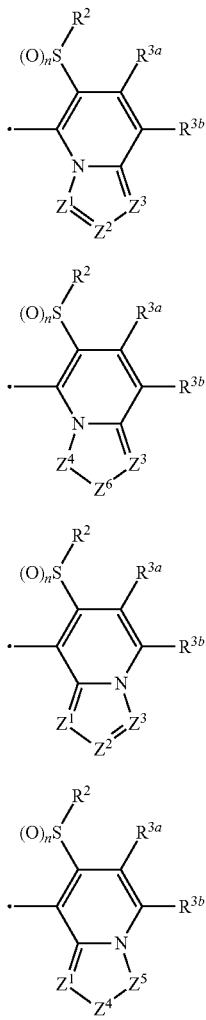

wherein: the dot in the Q group represents the point of attachment to formula (I), n is 0, 1 or 2, $R^2$ represents a cyclopropyl group, a cyclopropylmethyl group, or a C1-C6 alkyl group optionally having one or more halogen atoms, $Z^1$ represents a nitrogen atom or $CR^{3c}$, $Z^2$ represents a nitrogen atom or $CR^{3d}$, $Z^3$ represents a nitrogen atom or $CR^{3e}$, $Z^4$ represents $NR^{34}$, $CR^{36}R^{37}$ or $C(O)$, $Z^5$ represents $NR^{35}$, $CR^{38}R^{39}$ or $C(O)$, $R^{3a}$, $R^{3b}$, $R^{3c}$, $R^{3d}$ and $R^{3e}$ each independently represents a C1-C6 chain hydrocarbon group optionally having one or more substituents selected from Group B, a C3-C7 cycloalkyl group optionally having one or more substituents selected from Group E, a phenyl group optionally having one or more substituents selected from Group H, a five or six membered aromatic heterocyclic group optionally having one or more substituents selected from Group H, $OR^{12}$, $NR^{11}R^{12}$ $NR^{11a}R^{12a}$, $NR^{29}NR^{11}R^{12}$ $NR^{29}OR^{11}$, $NR^{11}c(O)R^{13}$, $NR^{29}NR^{11}C(O)R^{13}$, $NR^{11}C(O)OR^{14}$, $NR^{29}NR^{11}C(O)OR^{14}$, $NR^{11}C(O)NR^{15}R^{16}$, $NR^{29}NR^{11}C(O)NR^{15}R^{16}$, $N=CHNR^{15}R^{16}$, $N=S(O)_xR^{15}R^{16}$, $C(O)OR^{17}$, a cyano group, a nitro group, a halogen atom, or a hydrogen atom, x is 0 or 1, $R^{34}$ and $R^{35}$ each independently represents a C1-C6 chain hydrocarbon group optionally having one or more substituents selected from Group B, a phenyl group optionally having one or more substituents selected from Group C, a five or six membered aromatic heterocyclic group optionally having one or more substituents selected from Group C, a C3-C7 aliphatic hydrocarbon group optionally having one or more substituents selected from Group C, $C(O)OR^d$, $C(O)R^d$, $C(O)NR^eR^f$, $S(O)_2R^i$, or a hydrogen atom, $R^{36}$, $R^{37}$, $R^{38}$ and $R^{39}$ each independently represents a C1-C6 chain hydrocarbon group optionally having one or more substituents selected from Group B, a phenyl group optionally having one or more substituents selected from Group C, a C3-C7 aliphatic hydrocarbon group optionally having one or more substituents selected from Group C, or a hydrogen atom, $R^d$ represents a C1-C6 chain hydrocarbon group optionally having one or more halogen atoms, or a hydrogen atom, $R^e$ and $R^f$ each independently represents a C1-C6 chain hydrocarbon group optionally having one or more halogen atoms, a C3-C7 aliphatic hydrocarbon group optionally having one or more halogen atoms, or a hydrogen atom, $R^i$ represents a C1-C6 chain hydrocarbon group optionally having one or more halogen atoms, $A^2$ represents a nitrogen atom or $CR^{4a}$, $A^3$ represents a nitrogen atom or $CR^{4b}$, $A^4$ represents a nitrogen atom or $CR^{4c}$, $R^{4a}$, $R^{4b}$ and $R^{4c}$ each independently represents a C1-C6 chain hydrocarbon group optionally having one or more halogen atoms, a nitro group, $OR^{18}$, $NR^{18}R^{19}$, a cyano group, a halogen atom or a hydrogen atom, $R^{18}$ represents a C1-C6 chain hydrocarbon group optionally having one or more halogen atoms, $R^{19}$ represents a C1-C6 chain hydrocarbon group optionally having one or more halogen atoms or a hydrogen atom, T represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, a C3-C7 cycloalkyl group having one or more substituents selected from Group G, $OR^1$, $S(O)_mR^1$, $OS(O)_2R^1$, $CH_2OR^1$, $NR^1R^{24}$, $C(O)R^1$, $C(O)NR^1R^{24}$, $NR^{24}C(O)R^1$, $N=CR^1R^{30}$, a group represented by the following formula T-1, a group represented by the following formula T-2, a group represented by the following formula T-3, a group represented by the following formula T-4, a group represented by the following formula T-5, a group represented by the following formula T-6, a group represented by the following formula T-7, a group represented by the following formula T-8, a group represented by the following formula T-9, a group represented by the following formula T-10, a group represented by the following formula T-11, or a group represented by the following formula T-12:

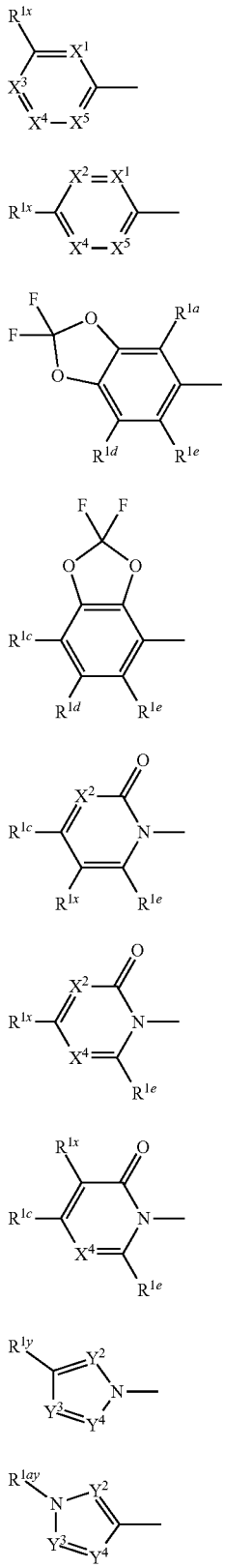

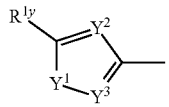

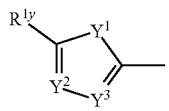

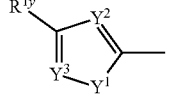

$X^1$ represents a nitrogen atom, or $CR^{1a}$,
$X^2$ represents a nitrogen atom, or $CR^{1b}$,
$X^3$ represents a nitrogen atom, or $CR^{1c}$,
$X^4$ represents a nitrogen atom, or $CR^{1d}$,
$X^5$ represents a nitrogen atom, or $CR^{1e}$,
$R^{1a}$, $R^{1b}$, $R^{1c}$, $R^{1d}$ and $R^{1e}$ each independently represents a C1-C6 chain hydrocarbon group optionally having one or more halogen atoms, a C3-C6 cycloalkyl group optionally having one or more halogen atoms, a halogen atom or a hydrogen atom,
$Y^1$ represents $NR^{25}$, an oxygen atom, or a sulfur atom,
$Y^2$ represents a nitrogen atom, or $CR^{26}$,
$Y^3$ represents a nitrogen atom, or $CR^{27}$,
$Y^4$ represents a nitrogen atom, or $CR^{28}$,
$R^{25}$ represents a C1-C6 chain hydrocarbon group optionally having one or more halogen atoms, a C1-C6 alkoxy group optionally having one or more halogen atoms, a C3-C7 cycloalkyl group optionally having one or more halogen atoms, or a (C3-C7 cycloalkyl)C1-C6 alkyl group optionally having one or more halogen atoms,
$R^{26}$, $R^{27}$, and $R^{28}$ each independently represents a C1-C6 chain hydrocarbon group optionally having one or more halogen atoms, a C3-C6 cycloalkyl group optionally having one or more halogen atoms, a halogen atom, or a hydrogen atom,
$R^{1x}$ represents $OR^7$, $OS(O)_2R^7$, $S(O)_mR^7$, $NR^8S(O)_2R^7$, a C1-C5 chain hydrocarbon group having one or more halogen atoms, a cyano group, or a halogen atom,
$R^{1y}$ represents $OR^7$, $OS(O)_2R^7$, $S(O)_mR^7$, $NR^8S(O)_2R^7$, a cyano group, a C1-C5 chain hydrocarbon group having one or more halogen atoms, or a halogen atom,
$R^{1ay}$ and $R^7$ each independently represents a C1-C6 chain hydrocarbon group having one or more halogen atoms,
$R^8$ represents a C1-C6 chain hydrocarbon group optionally having one or more halogen atoms, or a hydrogen atom,
m is 0, 1, or 2,
$R^1$ represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, or a C3-C7 cycloalkyl group having one or more substituents selected from Group G, $R^{11}$, $R^{17}$, $R^{24}$ and $R^{29}$ each independently represents a C1-C6 chain hydrocarbon group optionally having one or more halogen atoms, or a hydrogen atom, $R^{30}$ represents a C1-C6 chain hydrocarbon group optionally having one or more halogen atoms, or a hydrogen atom, $R^{12}$ represents a C1-C6 chain hydrocarbon group optionally having one or more halogen atoms, a C1-C6 alkyl group having one substituent selected from Group F, a phenyl group optionally having one or more substituents selected from Group H, a five or six membered aromatic heterocyclic group optionally having one or more substituents selected from Group H, $S(O)_2R^{23}$, or a hydrogen atom, $R^{23}$ represents a C1-C6 chain hydrocarbon group optionally having one or more halogen atoms, or a phenyl group optionally having one or more substituents selected from Group D, $R^{11a}$ and $R^{12a}$, and the nitrogen atom to which they are attached are taken together to form a three to seven membered nonaromatic heterocyclic group optionally having one or more substituents selected from Group E, $R^{13}$ represents a C1-C6 chain hydrocarbon group optionally having one or more halogen atoms, a C3-C7 cycloalkyl group optionally having one or more halogen atoms, a (C3-C6 cycloalkyl) C1-C3 alkyl group optionally having one or more halogen atoms, a phenyl group optionally having one or more substituents selected from Group D, a five or six membered aromatic heterocyclic group optionally having one or more substituents selected from Group D, or a hydrogen atom, $R^{14}$ represents a C1-C6 chain hydrocarbon group optionally having one or more halogen atoms, a C3-C7 cycloalkyl group optionally having one or more halogen atoms, a (C3-C6 cycloalkyl) C1-C3 alkyl group optionally having one or more halogen atoms, or a phenyl C1-C3 alkyl group, wherein the phenyl moiety in the phenyl C1-C3 alkyl group optionally has one or more substituents selected from Group D, $R^{15}$ and $R^{16}$ each independently represents a C1-C6 alkyl group optionally having one or more halogen atoms, Group B is a group selected from the group consisting of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen, atoms, a C3-C6 cycloalkyl group optionally having one or more halogen atoms, a cyano group, a hydroxy group, and a halogen atom;

Group C is a group selected from the group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, and a halogen atom;

Group D is a group selected from the group consisting of a C1-C6 chain hydrocarbon group optionally having one or more halogen atoms, a hydroxy group, a C1-C6 alkoxy group optionally having one or more halogen atoms, a C3-C6 alkenyloxy group optionally having one or more halogen atoms, a C3-C6 alkynyloxy group optionally having one or more halogen atoms, a sulfanyl group, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, an amino group, $NHR^{21}$, $NR^{21}R^{22}$, $C(O)R^{21}$, $OC(O)R^{21}$, $C(O)OR^{21}$, a cyano group, a nitro group, and a halogen atom, wherein $R^{21}$ and $R^{22}$ each independently represents a C1-C6 alkyl group optionally having one or more halogen atoms;

Group E is a group selected from the group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a halogen atom, an oxo group, a hydroxy group, a cyano group, and a nitro group;

Group F is a group selected from the group consisting of a C1-C6 alkoxy group optionally having one or more halogen atoms, a phenyl group optionally having one or more substituents selected from Group D, a five or six membered aromatic heterocyclic group optionally having one or more substituents selected from Group D, a C3-C7 cycloalkyl group optionally having one or more halogen atoms, a three to seven membered nonaromatic heterocyclic group optionally having one or more substituents selected from Group C, an amino group, $NHR^{21}$, $NR^{21}R^{22}$, and a cyano group;

Group G is a group selected from the group consisting of a C1-C6 alkyl group having one or more halogen atoms;

Group H is a group selected from the group consisting of a C1-C6 alkyl group optionally having one or more halogen atoms, $OR^{10}$, $NR^9R^{10}$, $C(O)R^{10}$, $C(O)NR^9R^{10}$, $OC(O)R^9$, $OC(O)OR^9$, $NR^{10}C(O)R^9$, $NR^{10}C(O)OR^9$, $C(O)OR^{10}$, a halogen atom, a nitro group, a cyano group, an amino group, and a five or six membered aromatic heterocyclic group, wherein $R^9$ represents a C1-C6 alkyl group optionally having one or more halogen atoms, or a C3-C6 cycloalkyl group optionally having one or more halogen atoms, and $R^{10}$ represents a C1-C6 alkyl group optionally having one or more halogen atoms, a C3-C6 cycloalkyl group optionally having one or more halogen atoms, or a hydrogen atom.

2. The compound according to claim 1 wherein $R^{4a}$, $R^{4b}$ and $R^{4c}$ each independently represents a hydrogen atom, or a halogen atom, T represents $OR^1$, $R^1$ represents a C1-05 chain hydrocarbon group having one or more halogen atoms, $R^2$ represents a C1-C6 alkyl group, Q represents a group represented by the above formula Q1 or a group represented by the above formula Q2, $R^{3a}$ and $R^{3b}$ each independently represents a C1-C6 alkyl group optionally having one or more halogen atoms, a phenyl group, a pyridyl group, a pyrimidinyl group, a pyrazolyl group, a triazolyl group $OR^{12}$, $NR^{11}R^{12}$, $NR^{11}C(O)R^{14}$, a halogen atom or a hydrogen atom, wherein the phenyl group, the pyridyl group, the pyrimidinyl group, the pyrazolyl group, and the triazolyl group each independently and optionally have one or more substituents selected from Group H, $R^{3c}$, $R^{3d}$ and $R^{3e}$ each independently represents a C1-C6 alkyl group optionally having one or more halogen atoms, $OR^{12}$, a halogen atom or a hydrogen atom, $Z^4$ represents $CR^{36}R^{37}$ or $C(O)$, $Z^5$ represents $NR^{35}$ or $CR^{38}R^{39}$, $R^{35}$ represents a C1-C6 alkyl group or a hydrogen atom, and $R^{36}$ and $R^{38}$ each independently represents a C1-C6 alkyl group optionally having one or more halogen atoms, or a hydrogen atom, and $R^{37}$ and $R^{39}$ each represents a hydrogen atom.

3. The compound according to claim 2 wherein $R^1$ represents a C1-C5 alkyl group having three or more fluorine atoms, $R^{3a}$ and $R^{3b}$ each independently represents a C1-C6 alkyl group optionally having one or more halogen atoms, $OR^{12}$, a halogen atom, or a hydrogen atom, and $R^{4a}$, $R^{4b}$ and $R^{4c}$ each represents a hydrogen atom.

4. The compound according to claim 3 wherein $R^2$ represents an ethyl group, and $R^{3c}$, $R^{3d}$, $R^{3e}$, $R^{35}$, $R^{36}$, $R^{37}$, $R^{38}$ and $R^{39}$ each represents a hydrogen atom.

5. The compound according to claim 1 wherein $A^2$ represents $CR^{4a}$ and $A^4$ represents $CR^{4c}$.

6. The compound according to claim 1 wherein $A^2$ represents $CR^{4a}$, $A^3$ represents $CR^{4b}$ and $A^4$ represents $CR^{4c}$.

7. The compound according to claim 1 wherein $A^2$ represents $CR^{4a}$, $A^3$ represents $CR^{4b}$, $A^4$ represents $CR^{4c}$, $R^{4a}$, $R^{4b}$ and $R^{4c}$ each independently represents a hydrogen atom or a halogen atom, T represents $OR^1$, $R^1$ represents a C1-C5 chain hydrocarbon group having one or more halogen atoms, $R^2$ represents a C1-C6 alkyl group, Q represents a group represented by the above formula Q1, $R^{3a}$ and $R^{3b}$ each independently represents a C1-C6 alkyl group optionally having one or more halogen atoms, a phenyl group, a pyridyl group, a pyrimidinyl group, a pyrazolyl group, a triazolyl group, $OR^{12}$, $NR^{11}R^{12}$, $NR^{11}C(O)OR^{14}$, a halogen atom or a hydrogen atom, wherein the phenyl group, the pyridyl group, the pyrimidinyl group, the pyrazolyl group, and the triazolyl group each independently and optionally have one or more substituents selected from Group H, and $R^{3c}$, $R^{3d}$ and $R^{3e}$ each independently represents a C1-C6 alkyl group optionally having one or more halogen atoms, $OR^{12}$, a halogen atom or a hydrogen atom.

8. The compound according to claim 7 wherein $R^1$ represents a C1-C5 alkyl group having three or more fluorine atoms, $R^{3a}$ and $R^{3b}$ each independently represents a C1-C6 alkyl group optionally having one or more halogen atoms, $OR^{12}$, a halogen atom, or a hydrogen atom, and $R^{4a}$, $R^{4b}$ and $R^{4c}$ each represents a hydrogen atom.

9. The compound according to claim 7 wherein $R^{3c}$, $R^{3d}$ and $R^{3e}$ each represents a hydrogen atom.

10. The compound according to claim 1 wherein $A^2$ represents $CR^{4a}$, $A^3$ represents $CR^{4b}$, $A^4$ represents $CR^{4c}$, $R^{4a}$, $R^{4b}$ and $R^{4c}$ each independently represents a hydrogen atom or a halogen atom, T represents $OR^1$, $R^1$ represents a C1-C5 chain hydrocarbon group having one or more halogen atoms, $R^2$ represents a C1-C6 alkyl group, Q represents a group represented by the above formula Q2, $R^{3a}$ and $R^{3b}$ each independently represents a C1-C6 alkyl group optionally having one or more halogen atoms, a phenyl group, a pyridyl group, a pyrimidinyl group, a pyrazolyl group, a triazolyl group, $OR^{12}$, $NR^{11}R^{12}$, $NR^{11}C(O)OR^{14}$, a halogen atom or a hydrogen atom, wherein the phenyl group, the pyridyl group, the pyrimidinyl group, the pyrazolyl group, and the triazolyl group each independently and optionally have one or more substituents selected from Group H, $Z^4$ represents $CR^{36}R^{37}$ or $C(O)$, $Z^5$ represents $NR^{35}$ or $CR^{38}R^{39}$, $R^{3e}$ represents a C1-C6 alkyl group optionally having one or more halogen atoms, $OR^{12}$, a halogen atom or a hydrogen atom, $R^{35}$ represents a C1-C6 alkyl group or a hydrogen atom, $R^{36}$ and $R^{38}$ each independently represents a C1-C6 alkyl group optionally having one or more halogen atoms, or a hydrogen atom, and $R^{37}$ and $R^{39}$ each represents a hydrogen atom.

11. The compound according to claim 10 wherein $R^1$ represents a C1-C5 alkyl group having three or more fluorine atoms, $R^{3a}$ and $R^{3b}$ each independently represents a C1-C6 alkyl group optionally having one or more halogen atoms, $OR^{12}$, a halogen atom, or a hydrogen atom, and $R^{4a}$, $R^{4b}$ and $R^{4c}$ each represents a hydrogen atom.

12. The compound according to claim 10 wherein $R^2$ represents an ethyl group, and $R^{35}$, $R^{36}$, $R^{37}$, $R^{38}$, and $R^{39}$ each represents a hydrogen atom.

13. A composition for controlling a harmful arthropod comprising the compound according to claim 1 and an inert carrier.

14. A composition comprising one or more ingredients selected from the group consisting of the following Group (a), Group (b), Group (c), Group (d) and Group (e), and the compound according to claim 1, Group (a): a group consisting of an insecticidal active ingredient, a miticidal active ingredient, and a nematicidal active ingredient;

Group (b): a fungicidal active ingredient; Group (c): a plant growth regulatory ingredient;

Group (d): a phytotoxicity-reducing ingredient; Group (e): a synergist.

15. A method for controlling a harmful arthropod which comprises applying an effective amount of the compound according to claim 1 to a harmful arthropod or a habitat where a harmful arthropod lives.

* * * * *